United States Patent
Pei et al.

(10) Patent No.: US 12,171,838 B2
(45) Date of Patent: Dec. 24, 2024

(54) POLYPEPTIDE CONJUGATES FOR INTRACELLULAR DELIVERY OF NUCLEIC ACIDS

(71) Applicant: Ohio State Innovation Foundation, Columbus, OH (US)

(72) Inventors: Dehua Pei, Columbus, OH (US); Marina Buyanova, Columbus, OH (US); Ziqing Qian, Wellesley, MA (US)

(73) Assignee: Ohio State Innovation Foundation, Columbus, OH (US)

( * ) Notice: Subject to any disclaimer, the term of this patent is extended or adjusted under 35 U.S.C. 154(b) by 936 days.

(21) Appl. No.: 17/257,224

(22) PCT Filed: Jul. 2, 2019

(86) PCT No.: PCT/US2019/040335
§ 371 (c)(1),
(2) Date: Dec. 30, 2020

(87) PCT Pub. No.: WO2020/010103
PCT Pub. Date: Jan. 9, 2020

(65) Prior Publication Data
US 2021/0244824 A1    Aug. 12, 2021

Related U.S. Application Data

(60) Provisional application No. 62/692,939, filed on Jul. 2, 2018.

(51) Int. Cl.
*A61K 47/00*    (2006.01)
*A61K 47/64*    (2017.01)
*C07K 7/64*    (2006.01)

(52) U.S. Cl.
CPC ............ *A61K 47/6455* (2017.08); *C07K 7/64* (2013.01)

(58) Field of Classification Search
CPC .............................. A61K 47/6455; C07K 7/64
See application file for complete search history.

(56) References Cited

U.S. PATENT DOCUMENTS

| | | |
|---|---|---|
| 5,523,308 A | 6/1996 | Costanzo et al. |
| 10,626,147 B2 | 4/2020 | Pei et al. |
| 10,815,276 B2 | 10/2020 | Pei et al. |
| 11,225,506 B2 | 1/2022 | Pei et al. |
| 2005/0107289 A1 | 5/2005 | Ghadiri et al. |
| 2008/0234183 A1 | 9/2008 | Hallbrink et al. |
| 2015/0297742 A1 | 10/2015 | Strieker et al. |
| 2016/0271216 A1 | 9/2016 | Kemper et al. |
| 2016/0317679 A1 | 11/2016 | Baumhof et al. |
| 2017/0355730 A1 | 12/2017 | Pei et al. |
| 2019/0282654 A1 | 9/2019 | Herad |
| 2019/0309020 A1 | 10/2019 | Pei et al. |
| 2020/0354697 A1 | 11/2020 | Sethuraman et al. |
| 2021/0070806 A1 | 3/2021 | Pei |

FOREIGN PATENT DOCUMENTS

| | | |
|---|---|---|
| EP | 1797901 A1 | 6/2007 |
| EP | 3544623 A1 | 10/2019 |
| WO | 2007055578 A1 | 5/2007 |
| WO | 2010/039088 A1 | 4/2010 |
| WO | 2014190313 A1 | 11/2014 |
| WO | 2015/179691 A9 | 11/2015 |
| WO | 2015179434 A1 | 11/2015 |
| WO | 2018098231 A1 | 5/2018 |
| WO | 2019217682 A1 | 11/2019 |
| WO | 2022178379 A1 | 8/2022 |

OTHER PUBLICATIONS

International Search Report and Written Opinion issued by the International Searching Authority (ISA/US) in PCT Application No. PCT/US2019/040335 on Nov. 6, 2019. 15 pages.
Non-Final Office Action issued in U.S. Appl. No. 17/053,684 on Sep. 8, 2023, 13 pages.
Final Office Action issued in U.S. Appl. No. 17/053,684 on May 11, 2023, 11 pages.
Non-Final Office Action issued in U.S. Appl. No. 17/053,684 on Jan. 20, 2023, 20 pages.
Pande et al., "Synthesis and Antibacterial Evaluation of Carvosamide Derivatives of Amino Acids", Pharmaceutical Chemistry Journal, Apr. 2014, vol. 48, No. 1, pp. 1-5.
Oh, Donghoon, et al. "Enhanced cellular uptake of short polyarginine peptides through fatty acylation and cyclization." Molecular pharmaceutics 11.8 (2014): 2845-2854.
Do, Hung, et al. "Difatty acyl-conjugated linear and cyclic peptides for siRNA delivery." ACS omega 2.10 (2017): 6939-6957.
Bedewy, Walaa, et al. "Generation of a cell-permeable cycloheptapeptidyl inhibitor against the peptidyl-prolyl isomerase Pin1." Organic & biomolecular chemistry 15.21 (2017): 4540-4543.
International Search Report and Written Opinion of Application No. PCT/US2019/031522, dated Sep. 27, 2019.
Extended European Search Report for Application No. 19831072.4 dated Nov. 3, 2022, 13 pages.
Advisory Action for U.S. Appl. No. 17/053,684 dated Nov. 2, 2022, 4 pages.
European Patent Office. Communication pursuant to Rule 164(1) EPC. in application No. 19831072.4, dated Jul. 29, 2022. 13 pages.
Lightfoot, Helen L. et al. "Endogenous polyamine function—the RNA perspective." Nucleic acids research 42.18 (2014): 11275-11290.
International Preliminary Report on Patentability issued for Application No. PCT/US2019/040335, dated Jan. 14, 2021.

(Continued)

*Primary Examiner* — Jeanette M Lieb
(74) *Attorney, Agent, or Firm* — Meunier Carlin & Curfman LLC

(57) ABSTRACT

The present disclosure provides for polypeptide conjugates. The polypeptide conjugates disclosed herein comprise a polyarginine peptide and a cyclic cell-penetrating peptide (cCPP) conjugated, directly or indirectly, to the polyarginine peptide. The present disclosure demonstrates that cCPPs conjugated to polyarginine peptides can be used to deliver nucleic acids to the cytosol of cells.

20 Claims, 20 Drawing Sheets
Specification includes a Sequence Listing.

(56) References Cited

OTHER PUBLICATIONS

Alhakamy, N. A., Nigatu, A. S., Berkland, C. J., and Ramsey, J. D. (2013) Noncovalently associated cell-penetrating peptides for gene delivery applications. Ther. Deliv. 4, 741-757.

Arthanari, Y.; Pluen, A.; Rajendran, R.; Aojula, H.; Demonacos, C. (2010) Delivery of therapeutic shRNA and siRNA by Tat fusion peptide targeting bcr-abl fusion gene in Chronic Myeloid Leukemia cells. J. Controlled Release 145, 272-280.

Collins, M., and Thrasher, A. (2015) Gene therapy: progress and predictions. Proc. R. Soc. B 282, 20143003.

Dowdy, S. F. (2017) Overcoming cellular barriers for RNA therapeutics. Nat. Biotechnol. 35, 222-229.

Eisenberg, David, Robert M. Weiss, and Thomas C. Terwilliger. The hydrophobic moment detects periodicity in protein hydrophobicity. Proceedings of the National Academy of Sciences 81.1 (1984): 140-144.

Engelman, D. M., Steitz, T. A., & Goldman, A. (1986). Identifying nonpolar transbilayer helices in amino acid sequences of membrane proteins. Annual review of biophysics and biophysical chemistry, 15(1), 321-353.

Gaj, T., Gersbach, C. A., and Barbas, C. F. (2013) ZFN, TALEN, and CRISPR/Cas-based methods for genome engineering. Trends Biotechnol. 31, 397-405.

Giacca, M., and Zacchigna, S. (2012) Virus-mediated gene delivery for human gene therapy. J. Controlled Release 161, 377-388.

Hardee, C., Arévalo-Soliz, L., Hornstein, B., and Zechiedrich, L. (2017) Advances in Non-Viral DNA Vectors for Gene Therapy. Genes 8, 65.

Hopp, T. P., & Woods, K. R. (1981). Prediction of protein antigenic determinants from amino acid sequences. Proceedings of the National Academy of Sciences, 78(6), 3824-3828.

Janin, J. O. E. L. (1979). Surface and inside volumes in globular proteins. Nature, 277(5696), 491-492.

Juliano, R. L. (2016) The delivery of therapeutic oligonucleotides. Nucleic Acids Res. 44(14): 6518-6548.

Kyte, J., & Doolittle, R. F. (1982). A simple method for displaying the hydropathic character of a protein. Journal of molecular biology, 157(1), 105-132.

Lächelt, U., and Wagner., E. (2015) Nucleic Acid Therapeutics Using Polyplexes: A Journey of 50 Years (and Beyond). Chem. Rev. 115, 11043-11078.

Law, M., Jafari, M., and Chen, P. (2008) Physicochemical characterization of siRNA-peptide complexes. Biotechnol Prog, 24, 957-963.

Peng, Q., Zhong, Z., and Zhuo, R. (2008) Disulfide Cross-Linked Polyethylenimines (PEI) Prepared via Thiolation of Low Molecular Weight PEI as Highly Efficient Gene Vectors. Bioconjugate Chem. 19, 499-506.

Qian, Z., LaRochelle, J. R., Jiang, B., Lian, W., Hard, R. L., Selner. N., Luechapanickhul, R., Barrios, A. M., and Pei, D. (2014) Early endosomal escape of a cyclic cell-penetrating peptide allows effective cytosolic cargo delivery. Biochemistry 53, 4034-4046.

Qian, Z., Martyna, A., Hard, R. L., Wang, J., Appiah-Kubi, G., Coss, C., Phelps, M. A., Rossman, J. S., and Pei, D. (2016) Discovery and Mechanism of Highly Efficient Cyclic Cell-Penetrating Peptides. Biochemistry 55, 2601-2612.

Sahin, U., Karikó, K., and Türeci, Ö. (2014) mRNA-based therapeutics—developing a new class of drugs. Nat. Rev. Drug Discov. 13, 759-780.

Shi, B. et al. (2011) Biodistribution of Small Interfering RNA at the Organ and Cellular Levels after Lipid Nanoparticle-mediated Delivery. J Histochem Cytochem. 59(8): 727-740.

Shrake, A., & Rupley, J. A. (1973). Environment and exposure to solvent of protein atoms. Lysozyme and insulin. Journal of molecular biology, 79(2), 351-371.

Tai, Z., Wang, X., Tian, J., Gao, Y., Zhang, L., Yao, C., Wu, X., Zhang, W., Zhu, Q., and Gao, S. (2015) Biodegradable Stearylated Peptide with Internal Disulfide Bonds for Efficient Delivery of siRNA In Vitro and In Vivo. Biomacromolecules 16, 1119-1130.

Tien, M. Z., Meyer, A. G., Sydykova, D. K., Spielman, S. J., & Wilke, C. O. (2013). Maximum allowed solvent accessibilites of residues in proteins. PloS one, 8(11), e80635.

Yin, H., Kanasty, R. L., Eltoukhy, A. A., Vegas, A. J., Dorkin, J. R., and Anderson, D. G. (2014) Non-viral vectors for gene-based therapy. Nat. Rev. Genet. 15, 541-555.

Yoo, J., Lee, D., Gujrati, V., Rejinold, N. S., Lekshmi, K. M., Uthaman, S., Jeong, C., Park, I.-K., Jon, S., and Kim, Y.-C. (2017) Bioreducible branched poly(modified nona-arginine) cell-penetrating peptide as a novel gene delivery platform. J. Controlled Release 246, 142-154.

POLYPEPTIDE CONJUGATES FOR INTRACELLULAR DELIVERY OF NUCLEIC ACIDS

CROSS-REFERENCE TO RELATED APPLICATIONS

This application is a national stage application filed under 35 U.S.C. § 371 of PCT/US2019/040335 filed Jul. 2, 2019, which claims the benefit of priority to U.S. Provisional Application No. 62/692,939, filed Jul. 2, 2018, the entire contents of which are incorporated herein by reference in its entirety for all purposes.

STATEMENT REGARDING FEDERAL FUNDING

This invention was made with government support under GM110208 and GM122459 awarded by the National Institutes of Health. The government has certain rights in the invention.

STATEMENT REGARDING SEQUENCE LISTING

The contents of the text file submitted electronically herewith are incorporated herein by reference in their entirety: A computer readable format copy of the Sequence Listing filename: CYPT_013_01WO_SeqList_ST25.txt date created, Jun. 25, 2019, file size 49 kilobytes.

FIELD OF THE INVENTION

The present disclosure relates to polypeptide conjugates comprising a cell-penetrating peptide (CPP), directly or indirectly attached to a group that binds to a nucleic acid sequence by electrostatic interactions. The group that binds to the nucleic acid sequence by electrostatic interactions comprises at least one peptide or polyamine, such as polyarginine peptide.

BACKGROUND

Nucleic acids and their synthetic analogs hold enormous potential as therapeutic agents, especially against targets that are challenging for conventional drug modalities (e.g., intracellular protein-protein interactions and missing/defective proteins caused by genetic mutations). In the classical gene therapy approach, a gene of interest is incorporated into a viral vector or bacterial plasmid and delivered to tissues/cells to restore normal or correct for pathologic gene expression. More recently, a wide variety of strategies exploiting short oligonucleotides have been explored. For example, antisense oligonucleotides and small interfering RNAs (siRNAs) can be used to specifically knockdown virtually any single or group of genes. Splice-switching oligonucleotides, microRNAs, and anti-microRNAs can also enhance target gene expression or modulate/switch mRNA splicing to express the desired gene products. Another potentially very powerful approach is the use of gene-editing platforms (e.g., TALENs and CRISPR/CAS9) to alter the genomic DNA and provide a permanent cure of the disease. Finally, chemically stabilized mRNAs can be directly delivered into diseased cells and tissues and used as templates for protein synthesis. Collectively, these nucleic acid-based approaches greatly expand the space of pharmacologic targets which are otherwise undruggable with conventional drugs.

Despite their undoubted potential, clinical translation of nucleic acid-based drugs is limited by their poor bioavailability in the target tissues/cells. Because of their high molecular weights and negative charges (with the exception of a few oligonucleotide analogs), nucleic acids cannot cross the cellular membranes to reach the cell interior. Therefore, these nucleic acid-based molecules must be delivered into the target tissues/cells by an appropriate delivery system. The present disclosure is directed towards a novel nucleic acid delivery system which can effectively penetrate through the cellular membranes to reach the interior of the cells.

SUMMARY OF THE INVENTION

In various embodiments, the present disclosure provides for polypeptide conjugates comprising:
a) a group that binds to a nucleic acid sequence by electrostatic interactions (P) comprising at least one peptide or polyamine; and
b) at least one cell-penetrating peptide (CPP);
wherein each peptide comprises at least three monomers selected from arginine, arginine-analog, lysine, lysine-analog, histidine, or histidine-analog; wherein the P is conjugated to the CPP through a bond or at least one linker (L); and
wherein the polypeptide conjugate is optionally charged.

In some embodiments, the polypeptide conjugate as disclosed herein has a molar ratio of P:CPP ranging from about 30:1 to about 1:2.

In some embodiments, the polypeptide conjugate as disclosed herein has an average molecular weight ranging from about 3 kDa to about 100 kDa.

In some embodiments, the polypeptide conjugate as disclosed herein has the following structure:

$$\text{CPP-L-}[P]_n\text{-L-CPP} \qquad (I)$$

wherein n is an integer from 1 to 50; and
wherein P at each occurrence is same or different.

In some embodiments of the polypeptide conjugate as disclosed herein, P comprises a polyarginine peptide (pArg) comprising at least three monomers selected from arginine or arginine-analog.

In some embodiments of the polypeptide conjugate as disclosed herein, P comprises a polyamine selected from a spermidine polymer or a spermine polymer.

In some embodiments of the polypeptide conjugate as disclosed herein, at least one of the CPP is a cyclic CPP (cCPP). In some embodiments, each CPP is, independently, a cyclic CPP (cCPP). In some embodiments, the cCPP comprises from 4 to 14 amino acid monomers. In other embodiments, each cCPP is, independently, selected from Table 4.

In some embodiments of the polypeptide conjugate as disclosed herein, the cCPP is a cyclo(fΦRrRrQ) (SEQ ID NO: 118) peptide or a cyclo(FfΦRrRrQ) (SEQ ID NO: 16), wherein:
F is a L-phenylalanine;
f is a D-phenylalanine;
Φ is an L-2-naphthylalanine;
R is a L-arginine;
r is a D-arginine; and
Q is a L-glutamine.

In some embodiments of the polypeptide conjugate as disclosed herein, the pArg comprises at least five arginine monomers or arginine-analog monomers. In some embodiments, the pArg further comprises at least one cysteine monomer.

In some embodiments, the polypeptide conjugate as disclosed herein has the following structure:

CPP-L-[pArg]$_n$-L-CPP                                 (II)

wherein the [pArg]$_n$ (SEQ ID NO: 130) is

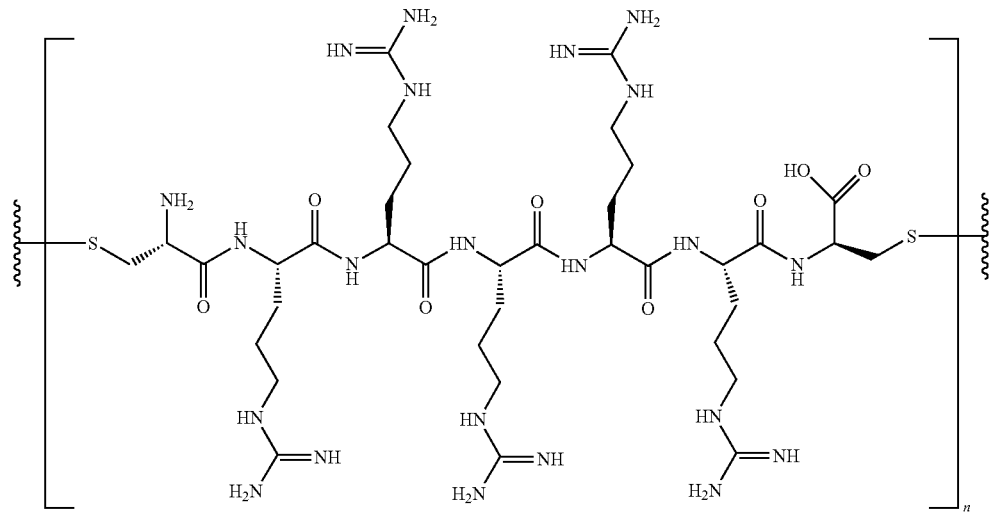

or a charged species thereof.

In some embodiments of the polypeptide conjugate as disclosed herein, n is an integer 1 to 40.

In some embodiments of the polypeptide conjugate as disclosed herein, at least one L comprises a divalent optionally substituted group selected from amino acid, alkylene, alkenylene, alkynylene, aryl, cycloalkyl, cycloalkenyl, cycloalkynyl, heterocyclyl, heteroaryl, —(R$^1$—X—R$^2$)z-, or combinations thereof; wherein each of R$^1$ and R$^2$ are independently selected from a bond, alkylene, alkenylene, alkynylene, carbocyclyl, and heterocyclyl, wherein R$^1$ and R$^2$ are not both a bond;

each X is independently N, S, and O; and z is an integer selected from 1 to 20.

In some embodiments of the polypeptide conjugate as disclosed herein, at least one L comprises an optionally substituted —(O—CH$_2$CH$_2$)z- or an optionally substituted —(CH$_2$CH$_2$—O)z-. In some embodiments, at least one L comprises a divalent 8-amino-3,6-dioxaoctanoic acid residue. In other embodiments, at least one L comprises a divalent 8-amino-3,6,9-trioxaundecanoic acid residue.

In some embodiments of the polypeptide conjugate as disclosed herein, at least one L comprises a physiological cleavable group (PCG). In some embodiments, each PCG is, independently, selected from —S—S—, carbonate, thiocarbonate, thioester, sulfoxide, hydrazine, or protease-cleavable dipeptide linker. In other embodiments, each PCG comprises at least one —S—S—.

In some embodiments of the polypeptide conjugate of formula (I), at least one of the '—' between L and [P]$_1$ represents a bond between two sulfur atoms (disulfide bond). In other embodiments, the "—" between each L and [P]$_n$ represents a bond between two sulfur atoms (disulfide bond).

In some embodiments of the polypeptide conjugate disclosed herein, each P, independently, further comprises at least one group selected from:

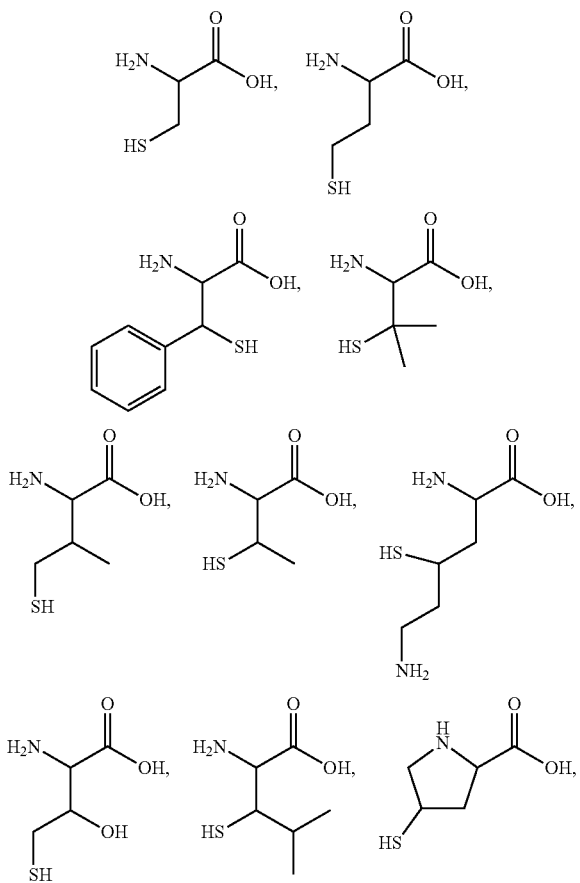

-continued

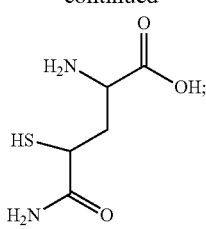

wherein the bond to the hydrogen on at least one of the N- or C-termini is replaced by a bond to the peptide or polyamine; and wherein the bond to the hydrogen on the thiol group is replaced by a bond to the CPP (or cCPP)

In some embodiments of the polypeptide conjugate disclosed herein, each P, independently, further comprises at least one group selected from:

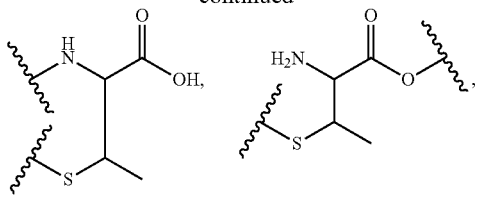

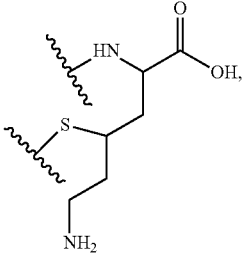 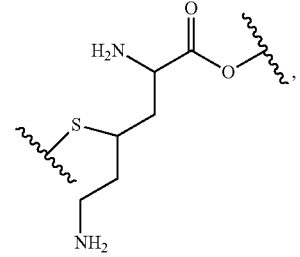

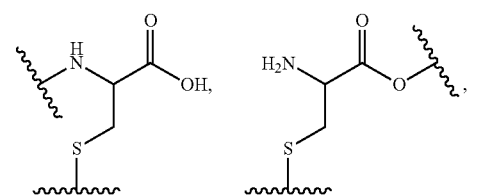

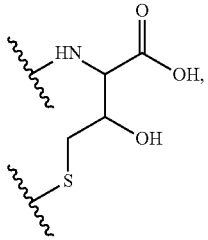 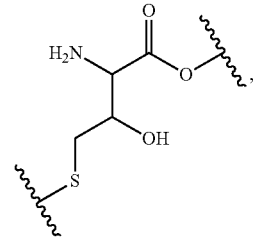

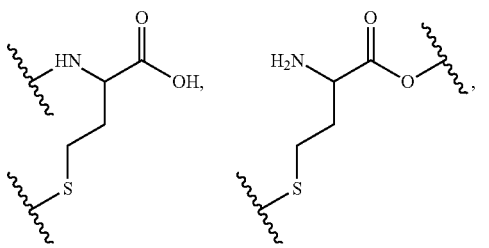 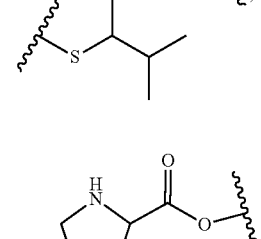

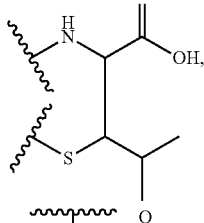 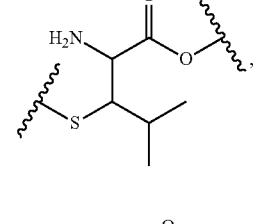

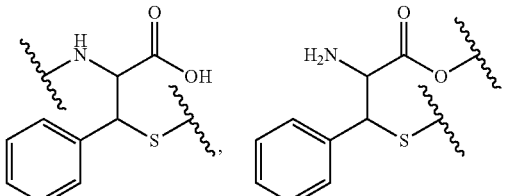

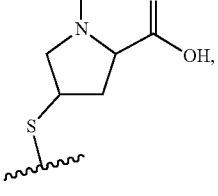 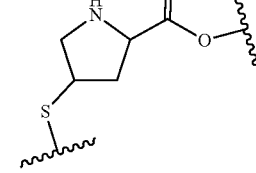

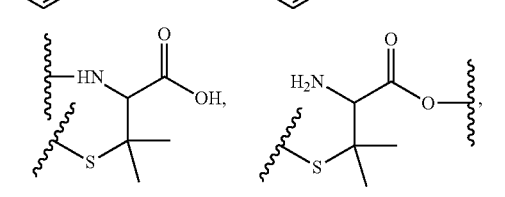

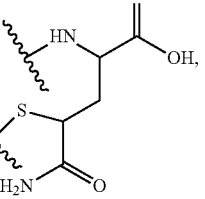 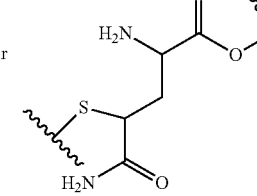

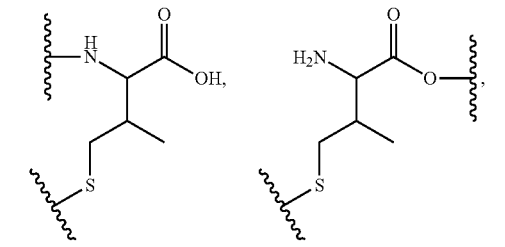

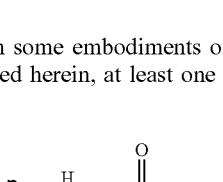 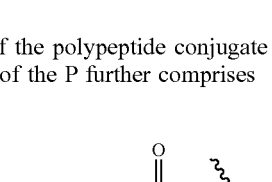

, or

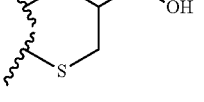 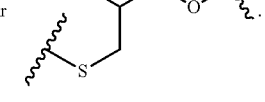

.

In some embodiments of the polypeptide conjugate disclosed herein, at least one of the P further comprises

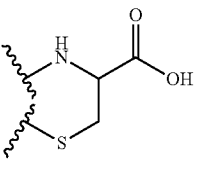 or 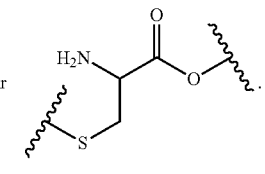

.

In other embodiments, at least one of the P further comprises at least two groups selected form

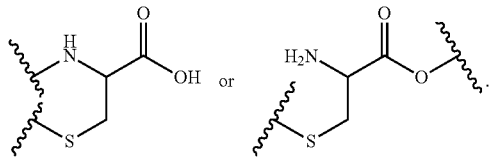 [SMILES: *NC(CS*)C(=O)O ; *OC(=O)C(N)CS*]

In some embodiments, the polypeptide conjugate as disclosed herein has the following structure:

CPP-L-([P¹]$_p$-L¹)$_t$-[P]$_n$-(L²-[P²]$_q$)$_t$-L-CPP     (III)

wherein n, p, and q are each independently an integer from 1 to 50;

t is each independently 0 or 1;

P¹ and P² each comprises at least one peptide or polyamine, wherein each peptide comprises at least three monomers selected from arginine, arginine-analog, lysine, lysine-analog, histidine, or histidine-analog, wherein P, P¹ and P², at each occurrence, are same or different; and L¹ and L² are each independently absent or L as defined in claim 1, wherein L, L¹, and L², at each occurrence, are same or different.

In some embodiments of the polypeptide conjugate of formula (III), P, P¹ or P² comprises a polyarginine peptide (pArg) comprising at least three monomers selected from arginine or arginine-analog. In other embodiments, P, P¹ or P² comprises a polyamine selected from a spermidine polymer or a spermine polymer.

In some embodiments of the polypeptide conjugate of formula (III), at least one of the CPP is a cyclic CPP (cCPP). In other embodiments, each CPP is, independently, a cyclic CPP (cCPP). In one embodiment, the cCPP comprises from 4 to 14 amino acid monomers. In another embodiment, each cCPP is, independently, selected from Table 4.

In some embodiments of the polypeptide conjugate of formula (III) as disclosed herein, the cCPP is a cyclo (fΦRrRrQ) (SEQ ID NO: 118) peptide or a cyclo (FfΦRrRrQ) (SEQ ID NO: 16), wherein:

F is a L-phenylalanine;
f is a D-phenylalanine;
Φ is an L-2-naphthylalanine;
R is a L-arginine;
r is a D-arginine; and
Q is a L-glutamine.

In some embodiments of the polypeptide conjugate of formula (III), the pArg comprises at least five arginine monomers or arginine-analog monomers. In one embodiment, the pArg further comprises at least one cysteine monomer.

In some embodiments of the polypeptide conjugate of formula (III), n is an integer 1 to 40. In some embodiments of the polypeptide conjugate of formula (III), n is an integer 5 to 40.

In some embodiments of the polypeptide conjugate of formula (III), at least one of L, L¹, or L² comprises a divalent optionally substituted group selected from amino acid, polyethylene glycol, alkylene, alkenylene, alkynylene, aryl, cycloalkyl, cycloalkenyl, cycloalkynyl, heterocyclyl, heteroaryl, —(R¹—X—R²)z-, or combinations thereof;

each of R¹ and R² are independently selected from a bond, alkylene, alkenylene, alkynylene, carbocyclyl, and heterocyclyl, wherein R¹ and R² are not both a bond;

each X is independently N, S, and O; and z is an integer selected from 1 to 20.

In some embodiments of the polypeptide conjugate of formula (III), at least one of L, L¹, or L² comprises an optionally substituted —(O—CH₂CH₂)z- or an optionally substituted —(CH₂CH₂—O)z-.

In some embodiments of the polypeptide conjugate of formula (III), at least one of L, L¹, or L² comprises a divalent 8-amino-3,6-dioxaoctanoic acid residue. In some embodiments, at least one of L, L¹, or L² comprises a divalent 8-amino-3,6,9-trioxaundecanoic acid residue. In other embodiments, at least one of L, L¹, or L² comprises a physiological cleavable group (PCG).

In some embodiments of the polypeptide conjugate of formula (III) as disclosed herein, each PCG is, independently, selected from —S—S—, carbonate, thiocarbonate, thioester, sulfoxide, hydrazine, or protease-cleavable dipeptide linker. In some embodiments, each PCG comprises at least one —S—S—.

In some embodiments of the polypeptide conjugate of formula (III), at least one of the "—" between L and ([P¹]$_p$-L¹)$_t$, L and [P]$_n$, or L and (L²-[P²]$_q$)$_t$ represents a bond between two sulfur atoms (disulfide bond).

In some embodiments of the polypeptide conjugate of formula (III), at least one of P, P¹ or P² further comprises at least one group selected from:

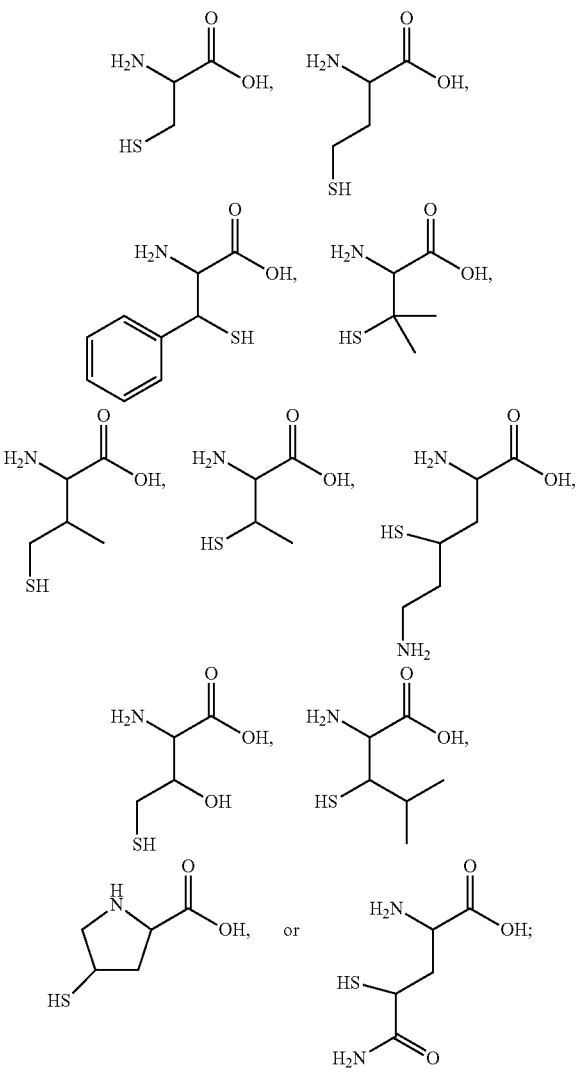

wherein the bond to the hydrogen on at least one of the N- or C-termini is replaced by a bond to the peptide or polyamine; and
wherein the bond to the hydrogen on the thiol group is replaced by a bond to the CPP.

In some embodiments of the polypeptide conjugate of formula (III), at least one of P, P¹ or P² further comprises at least one group selected from:

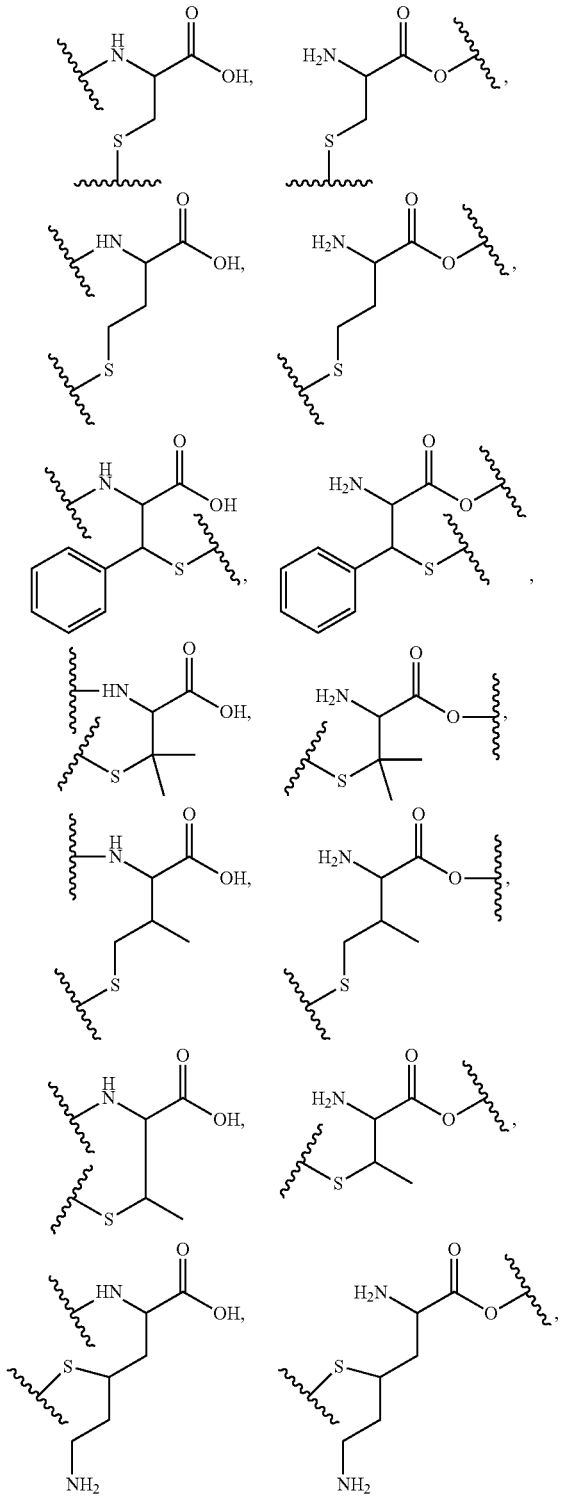

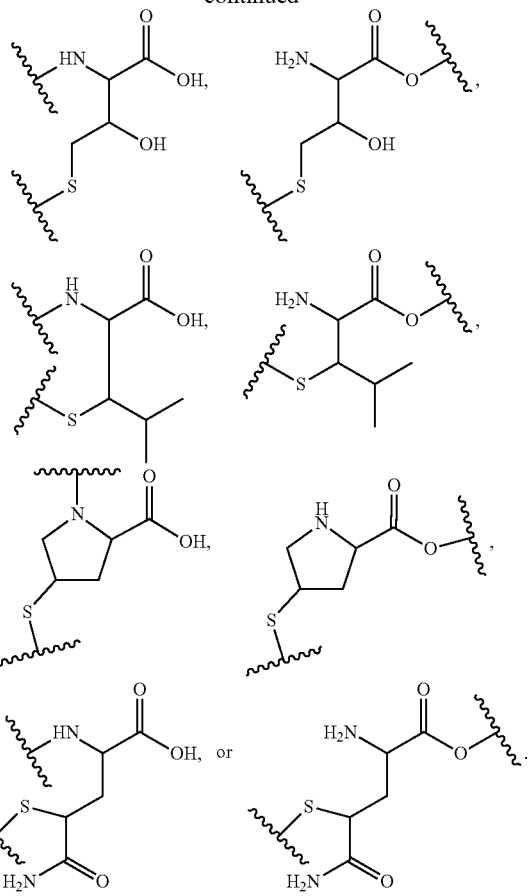

In some embodiments of the polypeptide conjugate of formula (III), at least one of P, P¹ or P² further comprises

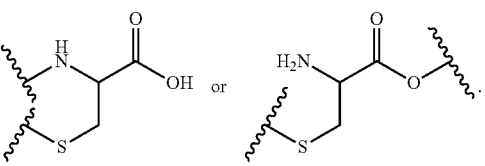 [SMILES: *NC(CS*)C(=O)O ; *OC(=O)C(N)CS*]

In other embodiments, at least two of P, P¹ or P² further comprises a group selected form In some embodiments of the polypeptide conjugate of formula (III), the pArg further comprises one or more β-alanine monomers. In some embodiments, each pArg comprises, independently, 3, 4, 5, 6, 7, or 8 arginine monomers. In other embodiments, each pArg comprises 5 arginine monomers. In one embodiment, at least one pArg further comprises a cysteine monomer.

In some embodiments of the polypeptide conjugate of formula (I), (II), or (III), the pArg is each independently selected from: -Cys-(Arg)$_x$-Cys- (SEQ ID NO: 131), -Cys-βAla-(Arg)$_x$-Cys- (SEQ ID NO: 132), -Cys-(Arg)$_x$-βAla-Cys- (SEQ ID NO: 133), or -Cys-βAla-(Arg)$_x$-βAla-Cys- (SEQ ID NO: 134), wherein x=3, 4, 5, 6, 7, or 8.

In some embodiments of the polypeptide conjugate of formula (I), (II), or (III), P is each independently selected from: -Cys-(Arg)$_x$-Cys- (SEQ ID NO: 131), -Cys-βAla-(Arg)$_x$-Cys- (SEQ ID NO: 132), -Cys-(Arg)$_x$-βAla-Cys- (SEQ ID NO: 133), or -Cys-βAla-(Arg)$_x$-βAla-Cys- (SEQ ID NO: 134), -Cys-(polyamine)$_x$-Cys-, -Cys-βAla-(polyamine)$_x$-Cys-, -Cys-(polyamine)$_x$-βAla-Cys-, -Cys-βAla-(polyamine)$_x$-βAla-Cys- (SEQ ID NO: 135), —S-(polyamine)$_x$-S—, wherein x=3, 4, 5, 6, 7, or 8.

In some embodiments, the polypeptide conjugate of formula (I) as disclosed herein has the structure

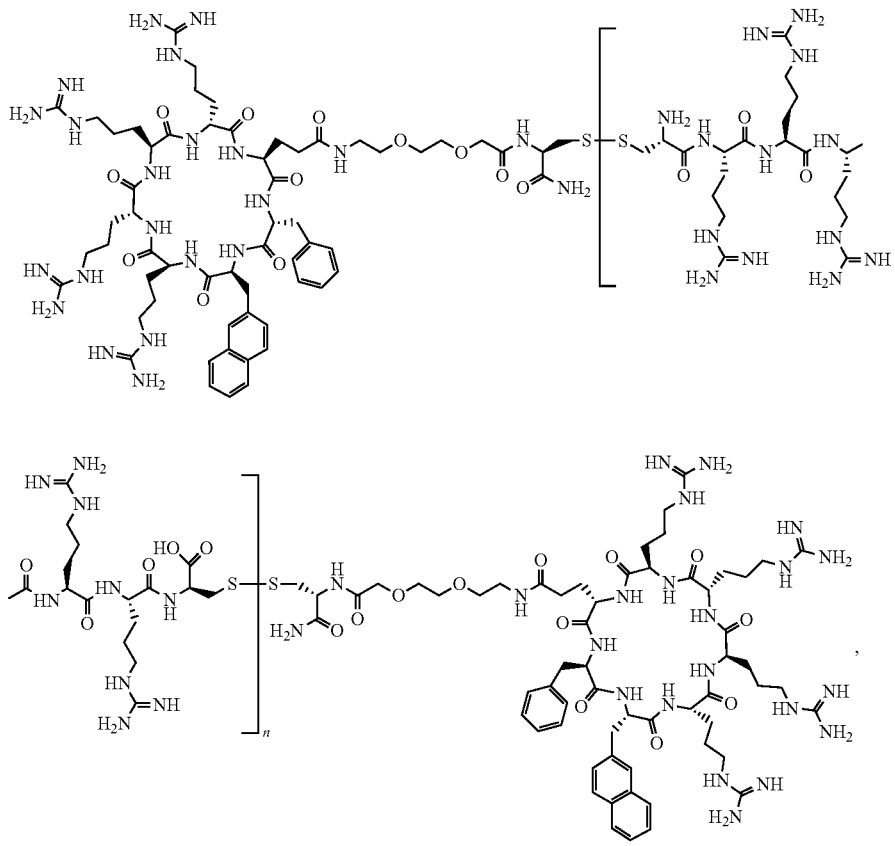

or a charged species thereof.

In some embodiments, the polypeptide conjugate of formula (I) as disclosed herein has the structure

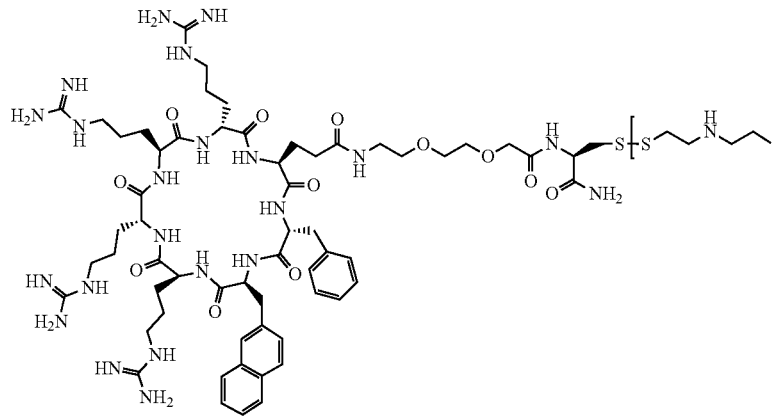

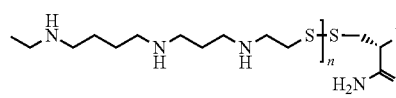
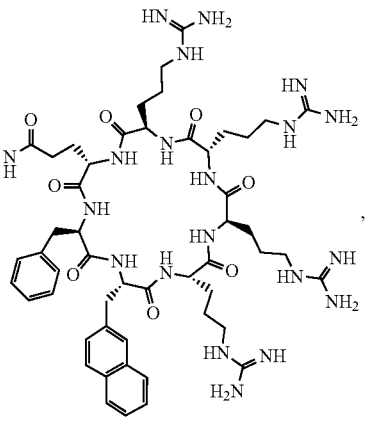

or a charged species thereof.

In some embodiments, the polypeptide conjugate as disclosed herein has the following structure:

$$\text{CPP-L-}([P]_m)_s \quad \text{(IV)}$$

wherein:
s is an integer from 1 to 10;
each m is, independently, an integer from 1 to 50; and
wherein P at each occurrence is same or different.

In some embodiments of the polypeptide conjugate of formula (IV), P comprises a polyarginine peptide (pArg) comprising at least three monomers selected from arginine or arginine-analog. In some embodiments, P comprises a polyamine selected from a spermidine polymer or a spermine polymer.

In some embodiments of the polypeptide conjugate of formula (IV), the CPP is acyclic CPP (cCPP). In some embodiments, the cCPP comprises from 4 to 14 amino acid monomers. In other embodiments, the cCPP is selected from Table 4.

In some embodiments of the polypeptide conjugate of formula (IV), the pArg comprises at least five arginine monomers or arginine-analog monomers. In some embodiments, the pArg further comprises at least one cysteine monomer.

In some embodiments of the polypeptide conjugate of formula (IV), L comprises a divalent optionally substituted group selected from amino acid, polyethylene glycol, alkylene, alkenylene, alkynylene, aryl, cycloalkyl, cycloalkenyl, cycloalkynyl, heterocyclyl, heteroaryl, —(R¹—X—R²)z-, or combinations thereof;
each of R¹ and R² are independently selected from a bond, alkylene, alkenylene, alkynylene, carbocyclyl, and heterocyclyl, wherein R¹ and R² are not both a bond;
each X is independently N, S, and O; and
z is an integer selected from 1 to 20.

In some embodiments of the polypeptide conjugate of formula (IV), L comprises an optionally substituted —(O—CH₂CH₂)z- or an optionally substituted —(CH₂CH₂—O)z-. In some embodiments, L comprises a divalent 8-amino-3,6-dioxaoctanoic acid residue. In other embodiments, L comprises a divalent 8-amino-3,6,9-trioxaundecanoic acid residue. In one embodiment, L comprises a physiological cleavable group (PCG).

In some embodiments of the polypeptide conjugate of formula (IV), each PCG is, independently, selected from —S—S—, carbonate, thiocarbonate, thioester, sulfoxide, hydrazine, or protease-cleavable dipeptide linker. In some embodiments, each PCG comprises at least one —S—S—.

In some embodiments of the polypeptide conjugate of formula (IV), L comprises a polythiolamine or a 3,5-bis (mercaptomethyl)benzoyl (Bmb) amide.

In some embodiments of the polypeptide conjugate of formula (IV), L comprises two or more physiological cleavable groups.

In some embodiments of the polypeptide conjugate of formula (IV), the "—" between L and ([P]ₘ)ₛ represents a bond between two sulfur atoms (disulfide bond).

In some embodiments of the polypeptide conjugate of formula (IV), each P, independently, further comprises at least one group selected from:

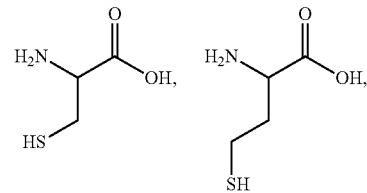

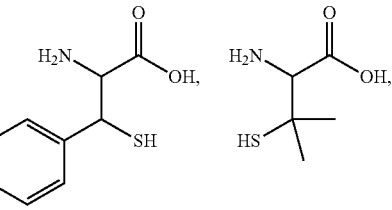

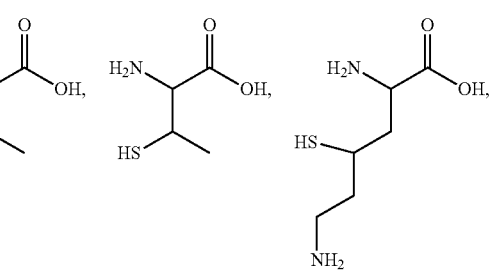

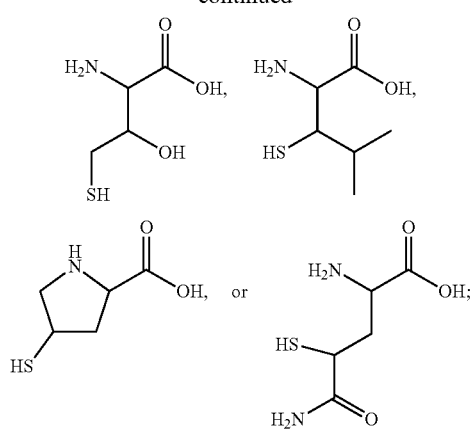
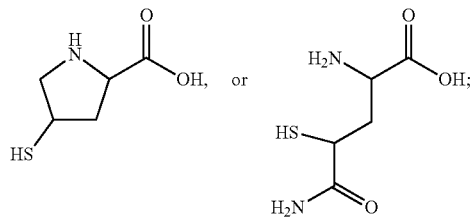
wherein the bond to the hydrogen on one at least one of the N- or C-termini is replaced by a bond to the peptide or polyamine; and
wherein the bond to the hydrogen on the thiol group is replaced by a bond to the CPP.
In some embodiments of the polypeptide conjugate of formula (IV), each P, independently, further comprises at least one group selected from:
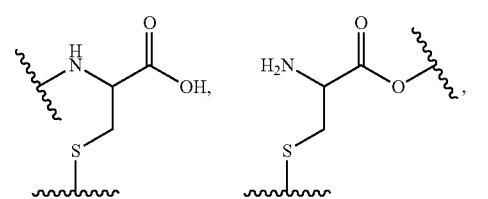
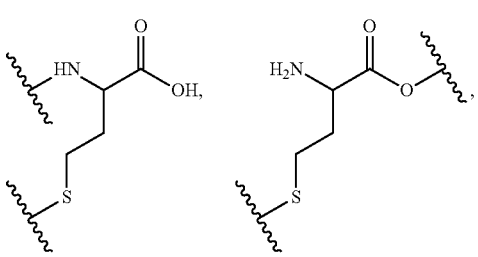
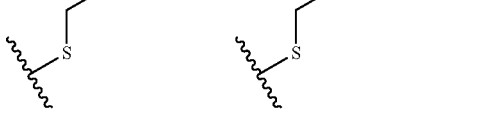
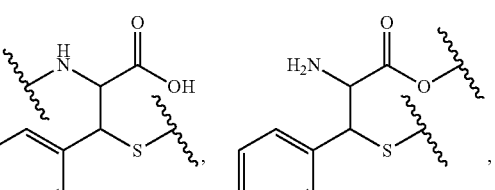
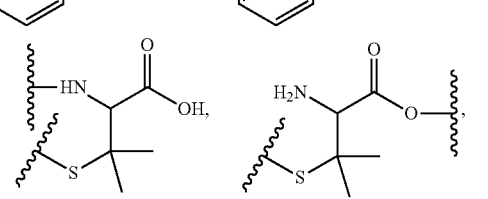
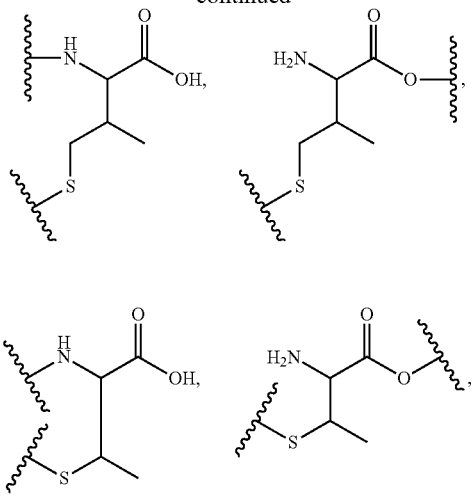
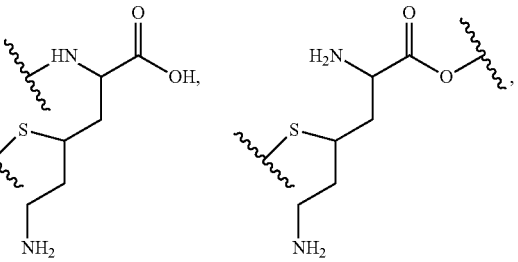
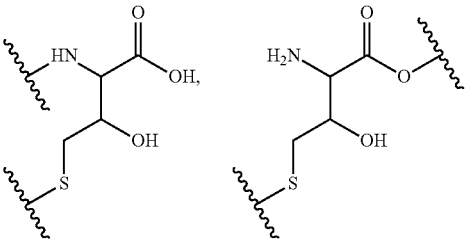
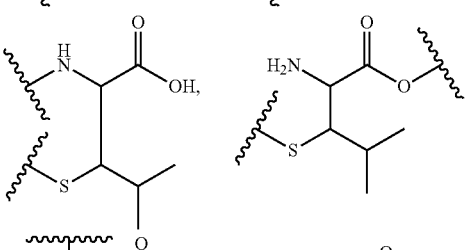
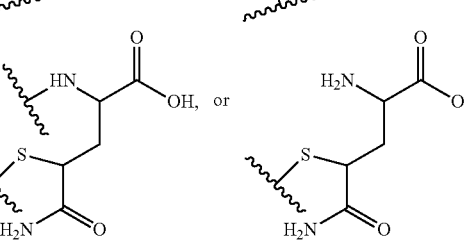

In some embodiments of the polypeptide conjugate of formula (IV), at least one of the P further comprises

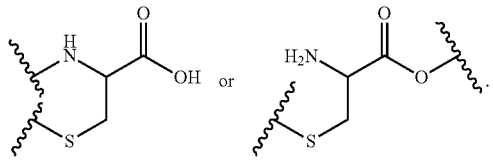 [SMILES: *NC(CS*)C(=O)O ; *OC(=O)C(N)CS*]

In other embodiments, at least one of the P further comprises at least two groups selected from

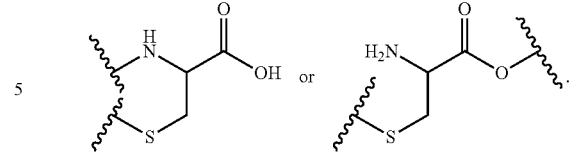

In some embodiments of the polypeptide conjugate of formula (IV), s is 2, 3, 4, or 5.

In some embodiments, the polypeptide conjugate of formula (IV) as disclosed herein has the structure

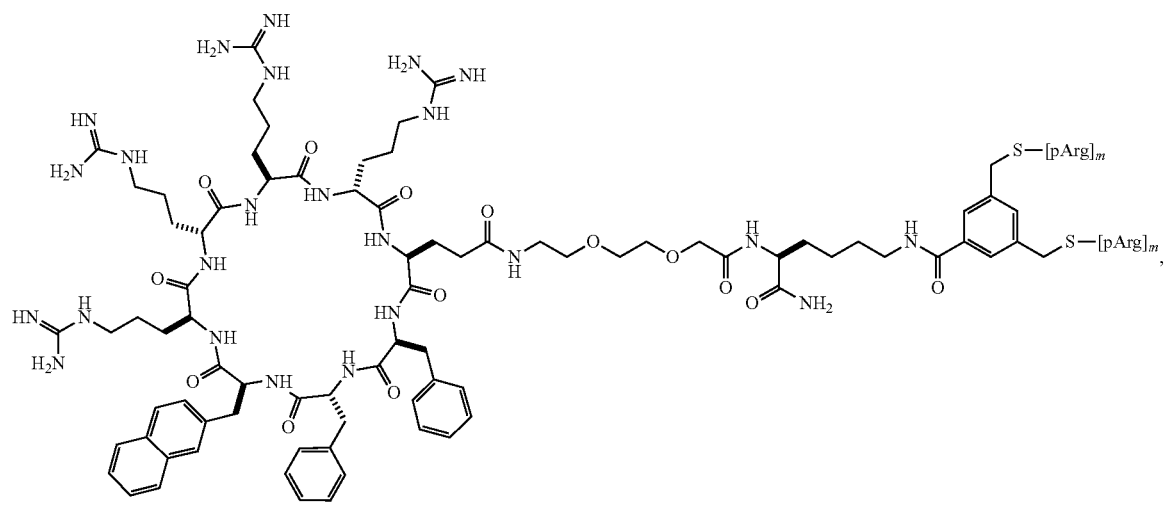

or a charged species thereof.

In some embodiments, the polypeptide conjugate of formula (IV) as disclosed herein has the structure

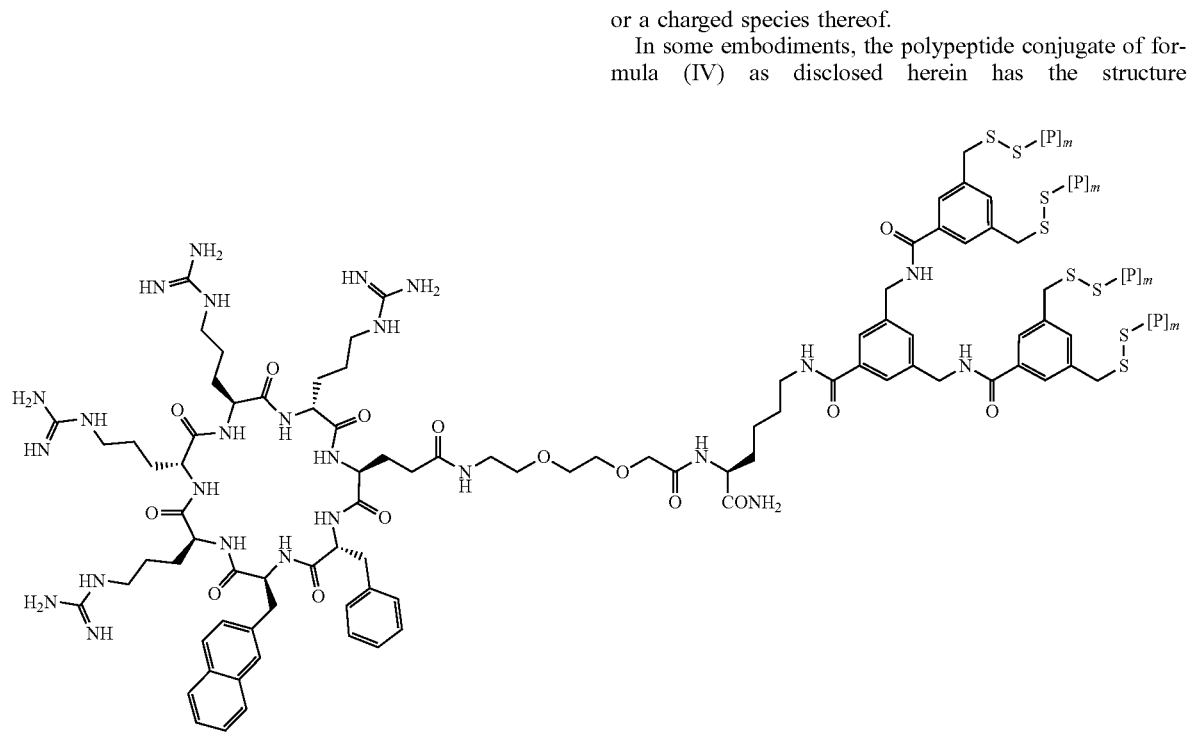

or a charged species thereof.

In some embodiments, the polypeptide conjugate as disclosed herein has the following structure:

$$cCPP\text{-}L\text{-}[P]_n\text{-}[P]_m\text{-}(L\text{-}cCPP)_v \qquad (V)$$

wherein, cCPP is a cyclic CPP; and n is an integer selected from 1 to 50;

m is an integer selected from 0 to 49 provided that the sum of n and m is 50 or less;

v is 0 or 1;

wherein P at each occurrence is same or different; and wherein when v is 0, the last [P] in $[P]_m$ is monovalent.

In some embodiments of the polypeptide conjugate of formula (V), the "—" between [P] and $[P]_m$ represents a bond between two sulfur atoms (a disulfide bond).

In some embodiments, the polypeptide conjugate of formula (IV) has the following structure:

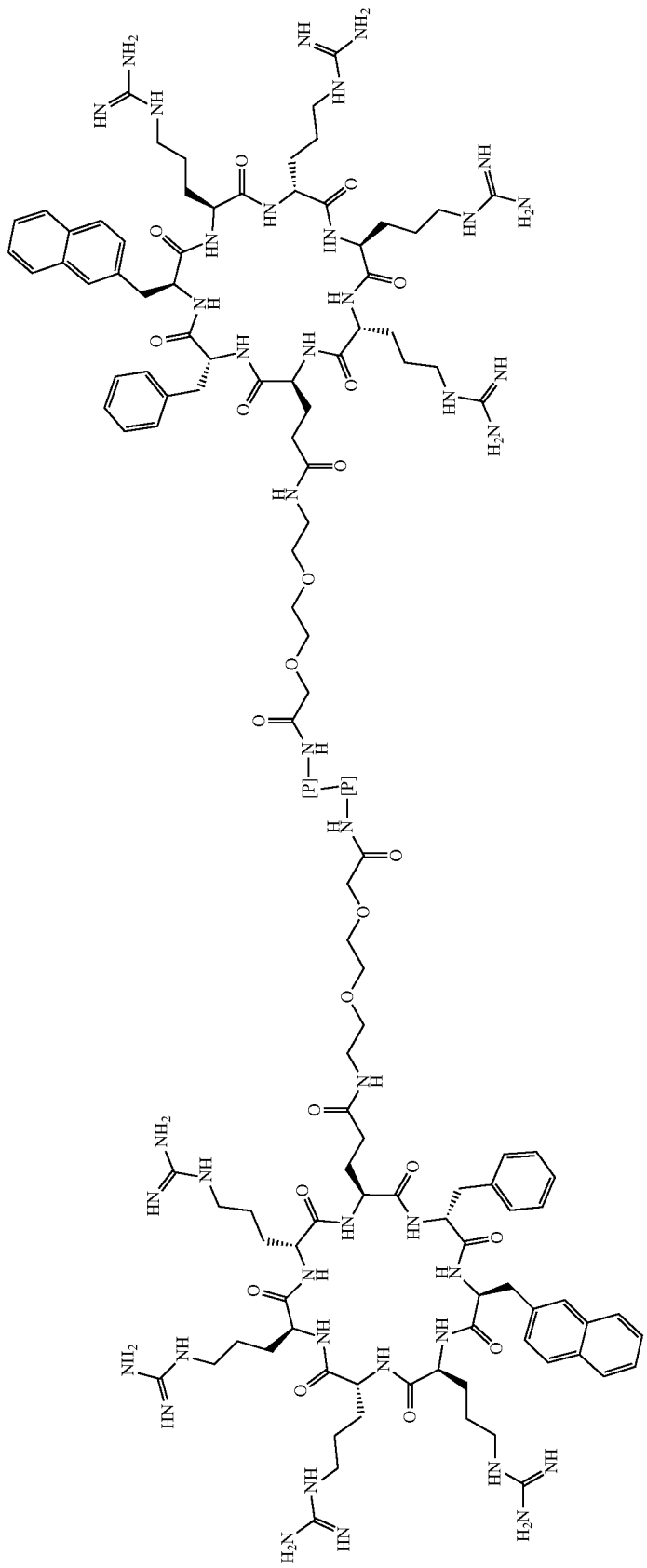

or a charged species thereof

In some embodiments of the polypeptide conjugate of formula (VI), the "—" between [P] and [P] represents a bond between two sulfur atoms (a disulfide bond).

In some embodiments, the polypeptide conjugate as disclosed herein has the following structure:

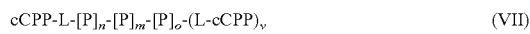  (VII)

wherein, cCPP is a cyclic CPP; and n is an integer selected from 1 to 50;

m and o, are each independently, an integer from 0 to 49 provided that the sum of n, m, and o is 50 or less;

v is 0 or 1;

wherein P at each occurrence is same or different; and wherein when v is 0, the last [P] in $[P]_o$ is monovalent.

In some embodiments of the polypeptide conjugate of formula (VII) as disclosed herein, at least one of the "—" between $[P]_n$ and $[P]_m$ or $[P]_m$ and $[P]_o$ represents a bond between two sulfur atoms (a disulfide bond). In other embodiments, the "—" between $[P]_n$ and $[P]_m$ and between $[P]_m$ and $[P]_o$ represents a bond between two sulfur atoms (a disulfide bond).

In some embodiments, the polypeptide conjugate of formula (VI) as disclosed herein, has the following structure:

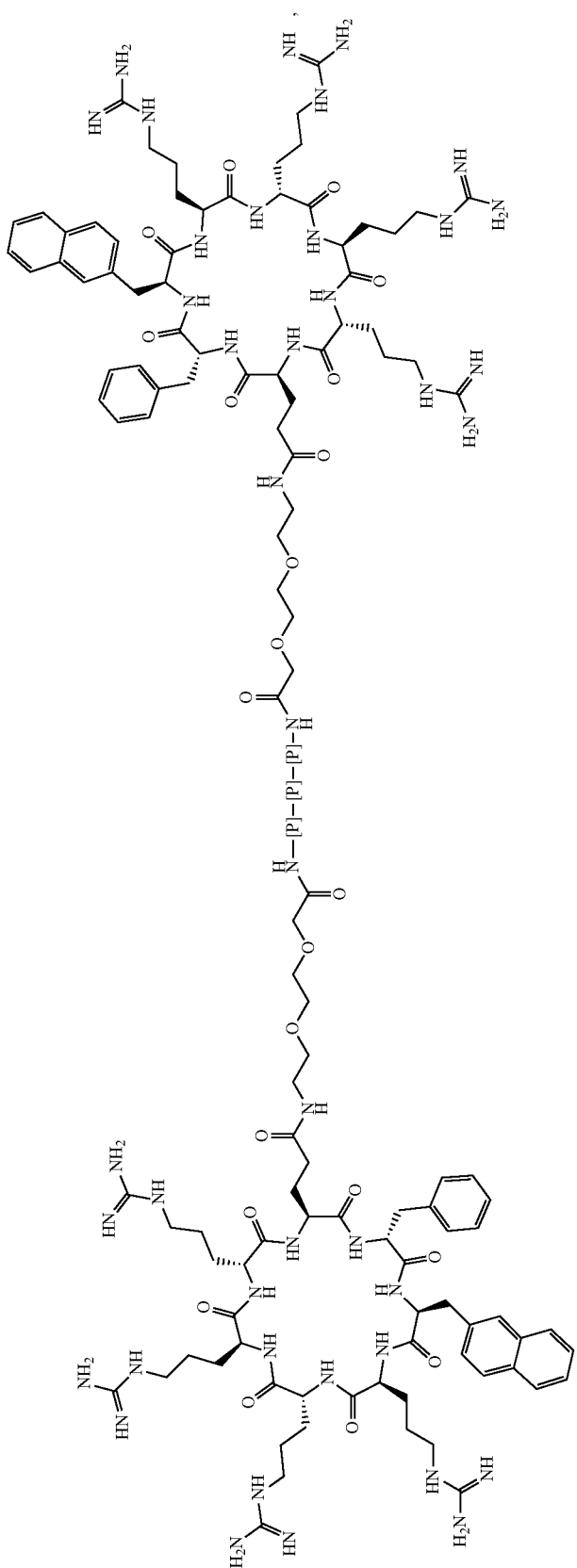

or a charged species thereof

In some embodiments of the polypeptide conjugate of formula (VIII) as disclosed herein, at least one of the "—" between [P] and [P] represents a bond between two sulfur atoms (a disulfide bond). In other embodiment, each "—" between [P] and [P] represents a bond between two sulfur atoms (a disulfide bond).

The present disclosure also relates to a complex comprising any one of the polypeptide conjugates as disclosed herein and at least one nucleic acid sequence.

The present disclosure also relates to a cell comprising any one of the polypeptide conjugates as disclosed herein.

The present disclosure also relates to a cell comprising a complex comprising any one of the polypeptide conjugates as disclosed herein and a nucleic acid sequence.

The present disclosure also relates to a method of delivering a nucleic acid sequence to a cell, comprising contacting the cell with any one of the complexes as disclosed herein.

The present disclosure also relates to a method of delivering a nucleic acid sequence to a cell of a subject in need thereof, comprising administering any one of the complexes as disclosed herein.

The present disclosure also relates to a method of treating a disease or condition in a patient in need thereof, comprising administering any one of the complexed as disclosed herein to the patient.

DETAILED DESCRIPTION

Figure 1:
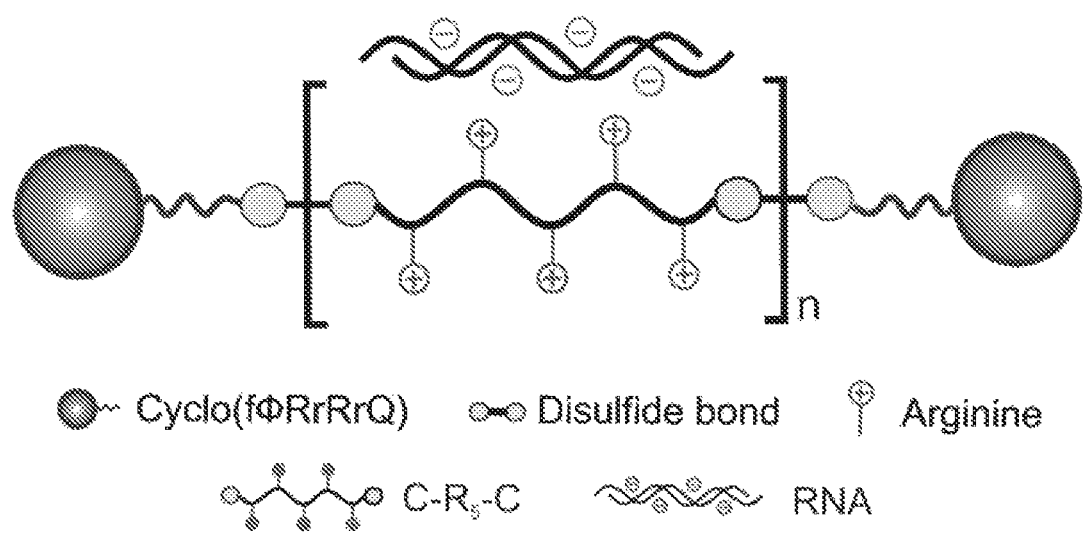
FIG. 1 shows a design concept of polypeptide conjugate of the disclosure.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value, as well as the recited value.

Throughout the present specification, numerical ranges are provided for certain quantities. It is to be understood that these ranges comprise all values and subranges therein. Thus, the range "from 50 to 80" includes all possible values therein (e.g., 50, 51, 52, 53, 54, 55, 56, etc.) and all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a polypeptide conjugate" refers to one or more polypeptide conjugates or at least one polypeptide conjugate. As such, the terms "a" (or "an"), "one or more" and "at least one" are used interchangeably herein. In addition, reference to "a polypeptide conjugate" by the indefinite article "a" or "an" does not exclude the possibility that more than one of the polypeptide conjugates is present, unless the context clearly requires that there is one and only one of the polypeptide conjugates.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, "treat," "treating," "treatment" and variants thereof, refers to any administration of the polypeptide conjugate of the present disclosure that partially or completely alleviates, ameliorates, prevents, relieves, inhibits, delays onset of, reduces severity of, and/or reduces incidence of one or more symptoms or features of a disease or a condition as described herein.

As used herein, "therapeutically effective" refers to an amount of the polypeptide conjugate or the complex thereof of the present disclosure that can deliver an amount of a therapeutic nucleic acid which confers a therapeutic effect on a patient.

As used herein, "cell penetrating peptide" or "CPP" refers to any peptide which is capable of penetrating a cell membrane. As used herein, "cyclic cell penetrating peptide" or "cCPP" refers to any cyclic peptide which is capable of penetrating a cell membrane.

As used herein, "linker" or "L" refers to a moiety that covalently attaches two or more components of the polypeptide conjugates disclosed herein (e.g., a linker may covalently attach a CPP and a group that binds to a nucleic acid sequence by electrostatic interactions [i.e., P]). In some embodiments, the linker can be natural or non-natural amino acid or polypeptide. In other embodiments, the linker is a synthetic compound containing two or more appropriate functional groups suitable to bind, e.g., the CPP and, independently, P. In some embodiments, the linker is about 3 to about 100 (e.g., about 3 to about 20) atoms in linear length (not counting the branched atoms or substituents). In some embodiments, the linker provides about 1 Å to about 400 Å in distance of the two groups to which it connects.

As used herein, "polypeptide" refers to a string of at least two amino acids attached to one another by a peptide bond. There is no upper limit to the number of amino acids that can be included in a polypeptide. Further, polypeptides may include non-natural amino acids, amino acid analogs, or other synthetic molecules that are capable of integrating into a polypeptide.

As used herein, "polyarginine peptide" refers to a string of at least two arginine amino acids (independently D or L). In some embodiments, the polyarginine peptide has the following repeating units where n is an integer selected from 1 to 100 and the polyarginine peptide can have one additional arginine monomer to make an odd-numbered chain.

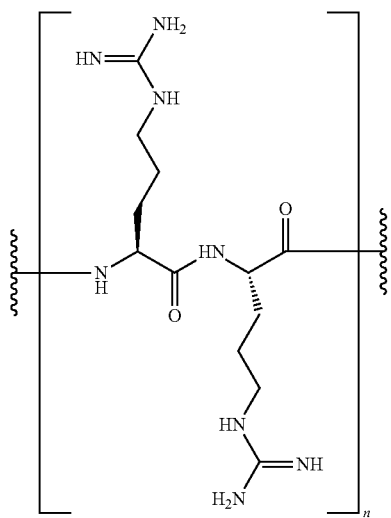

As used herein, a "monomer" refers to an amino acid residue in a polypeptide. In some embodiments, an amino acid monomer is divalent. In other embodiments, an amino acid monomer may be trivalent if the monomer is further substituted. For example, a cysteine monomer can independently form peptide bonds at the N and C termini, and also form a disulfide bond.

As used herein, an "amino acid-analog" or "analog" (e.g., "arginine-analog", "lysine-analog" or "histidine-analog") refers to a variant of an amino acid that retains at least one function of the amino acid, such as the ability to bind an oligonucleotide through electrostatic interactions. Such variants may have an elongated or shorter side chain (e.g., by one or more —$CH_2$— groups that retains the ability to bind an oligonucleotide through electrostatic interactions, or alternatively, the modification can improve the ability to bind an oligonucleotide through electrostatic interactions. For example, an arginine analog may include an additional methylene or ethylene between the backbone and guanidine/guanidinium group. Other examples include amino acids with one or more additional substituents (e.g., Me, Et, halogen, thiol, methoxy, ethoxy, C1-haloalkyl, C2-haloalkyl, amine, guanidine, etc). The amino acid-analog can be monovalent, divalent, or trivalent.

Throughout the present specification, peptides and amino acid monomers are depicted as charge neutral species. It is to be understood that such species may bear a positive or negative charge depending on the conditions. For example, at pH 7, the N-terminus of an amino acid is protonated and bears a positive charge (—$NH_3^+$), and the C-terminus of an amino acid is deprotonated and bears a negative charge (—$CO_2^-$). Similarly, the side chains of certain amino acids may bear a positive or negative charge.

As used herein, a "charged species" refers to a moiety bearing either a positive or negative charge. For example, when the CPP or cCPP contains arginine or arginine analog monomers, the guanidine group

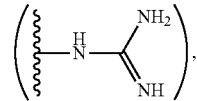

under certain conditions, can be protonated to form a guanidinium group

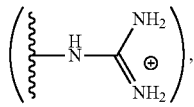

i.e., the charged species. In some embodiments, the between about 5% and about 100% of the moieties in the conjugates described herein that are capable of bearing a charge, are changed, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and subranges therebetween.

As used herein, "divalent" refers to moiety having two points of attachment to the rest of the molecule. For example, a divalent linker group was two points of attachment in a polypeptide conjugate, the first point of attachment is to the cell-penetrating peptide (CPP) and the second point of attachment is to the group that binds to a nucleic acid sequence by electrostatic interactions (P).

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, pentylene, and the like. Unless stated otherwise specifically in the specification, an alkylene chain can be optionally substituted as described herein.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethenylene (—CH=CH—), propenylene, butenylene, and the like. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to forty carbon atoms, and having one or more carbon-carbon triple bonds. Non-limiting examples of $C_2$-$C_{40}$ alkynylene include ethynylene (—C≡C—), propargylene and the like. Unless stated otherwise specifically in the specification, an alkynylene chain can be optionally substituted.

"Aryl" refers to a hydrocarbon ring system comprising hydrogen, 6 to 40 carbon atoms and at least one aromatic ring. For purposes of this disclosure, the aryl can be a monovalent or a divalent radical (not counting substituents), which can be a monocyclic, bicyclic, tricyclic or tetracyclic ring system, and which can include fused or bridged ring systems. Aryl radicals include, but are not limited to, radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl radical can be divalent when used as a linker or as a part of a linker. Unless stated otherwise specifically in the specification, an aryl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl and rings that are fully unsaturated, partially unsaturated, and fully saturated. In some embodiments, the carbocyclyl can be divalent when used as a linker or as a part of a linker. Unless stated otherwise specifically in the specification, a carbocyclyl group can be optionally substituted.

"Cycloalkyl" refers to a stable non-aromatic monocyclic or polycyclic fully saturated hydrocarbon radical having from 3 to 40 carbon atoms and at least one ring, wherein the ring consists solely of carbon and hydrogen atoms, which can include fused or bridged ring systems. For purposes of this disclosure, the cycloalkyl can be a monovalent or a divalent radical (not counting substituents). Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. In some embodiments, the cycloalkyl radical can be divalent when used as a linker or as a part of a linker. Unless otherwise stated specifically in the specification, a cycloalkyl group can be optionally substituted.

"Cycloalkenyl" refers to a stable non-aromatic monocyclic or polycyclic hydrocarbon radical having from 3 to 40 carbon atoms, at least one ring having, and one or more carbon-carbon double bonds, wherein the ring consists solely of carbon and hydrogen atoms, which can include fused or bridged ring systems. For purposes of this invention, the cycloalkenyl can be a monovalent or a divalent radical (not counting substituents). Monocyclic cycloalkenyl radicals include, for example, cyclopentenyl, cyclohexenyl, cycloheptenyl, cyclooctenyl, and the like. Polycyclic cycloalkenyl radicals include, for example, bicyclo [2.2.1] hept-2-enyl and the like. In some embodiments, the cycloalkenyl radical can be divalent when used as a linker or as a part of a linker. Unless otherwise stated specifically in the specification, a cycloalkenyl group can be optionally substituted.

"Cycloalkynyl" refers to a stable non-aromatic monocyclic or polycyclic hydrocarbon radical having from 3 to 40 carbon atoms, at least one ring, and one or more carbon-carbon triple bonds, wherein the ring consists solely of carbon and hydrogen atoms, which can include fused or bridged ring systems. For purposes of this invention, the cycloalkynyl can be a monovalent or a divalent radical (not counting substituents). Monocyclic cycloalkynyl radicals include, for example, cycloheptynyl, cyclooctynyl, and the like. In some embodiments, the cycloalkynyl radical can be divalent when used as a linker or as a part of a linker. Unless otherwise stated specifically in the specification, a cycloalkynyl group can be optionally substituted.

"Heterocyclyl," "heterocyclic ring" or "heterocycle" refers to a stable 3- to 20-membered aromatic ring radical which consists of two to twelve carbon atoms and from one to six heteroatoms selected from the group consisting of nitrogen, oxygen and sulfur. For purposes of this invention, the heterocyclyl radical can be a monovalent or a divalent radical (not counting substituents). Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. In some embodiments, the heterocyclyl radical can be divalent when used as a linker or as a part of a linker. Unless stated otherwise specifically in the specification, a heterocyclyl group can be optionally substituted.

"Heteroaryl" refers to a 5- to 20-membered ring system radical comprising hydrogen atoms, one to fourteen carbon atoms, one to six heteroatoms selected from the group consisting of nitrogen, oxygen and sulfur, and at least one aromatic ring. For purposes of this invention, the heteroaryl radical can be a monovalent or a divalent radical (not counting substituents) and can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl radical can be divalent when used as a linker or as a part of a linker. Unless stated otherwise specifically in the specification, a heteroaryl group can be optionally substituted.

The term "ether" used herein refers to a straight or branched divalent radical moiety —[(CH$_2$)$_m$—O—(CH$_2$)$_n$]$_z$— wherein each of m, n, and z are independently selected from 1 to 40. Examples include, but are not limited to, polyethylene glycol. Unless stated otherwise specifically in the specification, the ether can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more atoms on any of the above groups are replaced by a substituent listed in this paragraph, and the substituent forms a covalent bond with the CPP, P, or L. For example, in certain embodiments, any of the above groups can be substituted at a first position with a carboxylic acid (i.e., —C(=O)OH) which forms an amide bond with a lysine in the CPP, or a group can be substituted at a second position with a thiol group which forms a disulfide bond with a cysteine (or amino acid analog having a thiol group).

Polypeptide Conjugates

Nucleic acid delivery systems can be divided into two main strategies: 1) viral delivery and 2) non-viral delivery. Viral vectors have the advantage of high efficacy, but can result in immunogenicity and tumorigenicity. Additionally, viral delivery is limited to biologically synthesized nucleic acids and incompatible with short synthetic oligonucleotides or their analogs. Non-viral delivery vectors include various cationic lipids, polymers, carbohydrate analogs, and cell-penetrating peptides (CPPs). These vectors are usually mixed with nucleic acids to form complexes such as nanoparticles or liposomes. The complexes/conjugates are taken up by cells through various endocytic pathways, including macropinocytosis, clathrin- and caveolae-mediated endocytosis. The main limitation of the non-viral delivery systems has been the poor endosomal escape efficiency, resulting in the entrapment of the vast majority of the cargoes inside the endosomal/lysosomal compartments. The nanoparticle-based systems are also limited to distribution into organs/tissues with good blood access and/or relatively large blood vessel fenestrations, such as liver, spleen, or kidney.

The present disclosure relates to a discovery that some CPPs, including cyclic CPPs (cCPPs), are highly active with cytosolic delivery efficiencies of up to 120% (compared to 2% for Tat). The CPPs bind directly to the plasma membrane phospholipids and are internalized by various endocytic mechanisms. The inventors discovered that cCPPs are especially remarkably efficient in endosomal escape, by binding to the early endosomal membrane and inducing budding of small vesicles enriched with the CPPs from the endosomal membrane. Subsequent collapse of the budded vesicles releases the CPPs (and CPP-cargo conjugates) into the cytosol. Moreover, the cCPPs have proven highly effective for cytosolic delivery of a wide variety of cargos, including small molecules, linear peptides, cyclic peptides, and proteins.

The present disclosure relates to a discovery of novel biodegradable polypeptide conjugate comprising at least one CPP, which form non-covalent complexes with nucleic acids (e.g., siRNA). Without being bound by theory, the polypeptide conjugate/nucleic acid complex can effectively enter the cytosol of mammalian cells, where the complex undergoes spontaneous degradation in the reducing environment, releasing the nucleic acid cargo for modulation of the biological activity of a specific target(s).

In various embodiments, the polypeptide conjugates described herein comprise:
  a) a group that binds to a nucleic acid sequence by electrostatic interactions (P) comprising at least one peptide or polyamine; and
  b) at least one cell-penetrating peptide (CPP);
  wherein each peptide comprises at least three monomers selected from arginine, arginine-analog, lysine, lysine-analog, histidine, or histidine-analog; wherein the P is conjugated to the CPP through a bond or at least one linker (L); and
  wherein the polypeptide conjugate is optionally charged.

In some embodiments, the polypeptide conjugate as disclosed herein has a molar ratio of P:CPP ranging from about 30:1 to about 1:2. In some embodiments, the molar ratio of P:CPP is about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, or about 1:2, inclusive of all values and subranges therebetween.

In some embodiments, the polypeptide conjugate as disclosed herein has an average molecular weight ranging from about 1 kDa to about 100 kDa. In some embodiments, the average molecular weight of the polypeptide conjugate is about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 36 kDa, about 37 kDa, about 38 kDa, about 39 kDa, about 40 kDa, about 41 kDa, about 42 kDa, about 43 kDa, about 44 kDa, about 45 kDa, about 46 kDa, about 47 kDa, about 48 kDa, about 49 kDa, about 50 kDa, about 51 kDa, about 52 kDa, about 53 kDa, about 54 kDa, about 55 kDa, about 56 kDa, about 57 kDa, about 58 kDa, about 59 kDa, about 60 kDa, about 61 kDa, about 62 kDa, about 63 kDa, about 64 kDa, about 65 kDa, about 66 kDa, about 67 kDa, about 68 kDa, about 69 kDa, about 70 kDa, about 71 kDa, about 72 kDa, about 73 kDa, about 74 kDa, about 75 kDa, about 76 kDa, about 77 kDa, about 78 kDa, about 79 kDa, about 80 kDa, about 81 kDa, about 82 kDa, about 83 kDa, about 84 kDa, about 85 kDa, about 86 kDa, about 87 kDa, about 88 kDa, about 89 kDa, about 90 kDa, about 91 kDa, about 92 kDa, about 93 kDa, about 94 kDa, about 95 kDa, about 96 kDa, about 97 kDa, about 98 kDa, about 99 kDa, or about 100 kDa, inclusive of all ranges and subranges therebetween. In some embodiments, the polypeptide conjugate as disclosed herein has an average molecular weight ranging from about 3 kDa to about 100 kDa.

In some embodiments, the polypeptide conjugate as disclosed herein has the following structure:

$$\text{CPP-L-[P]}_n\text{-L-CPP} \qquad (I)$$

wherein n is an integer from 1 to 50; and wherein P at each occurrence is same or different.

In some embodiments of the polypeptide conjugate as disclosed herein, P comprises a polyarginine peptide (pArg) comprising at least three monomers selected from arginine or arginine-analog.

In some embodiments of the polypeptide conjugate as disclosed herein, P comprises a polyamine selected from a spermidine polymer or a spermine polymer.

In some embodiments of the polypeptide conjugate as disclosed herein, at least one of the CPP is a cyclic CPP (cCPP). In some embodiments, the CPP is, each independently, a cyclic CPP (cCPP). In some embodiments, cCPP comprises from 4 to 14 amino acid monomers. In other embodiments, cCPP is, each independently, selected from Table 4.

In some embodiments of the polypeptide conjugate as disclosed herein, the cCPP is a cyclo(fΦRrRrQ) peptide or a cyclo(FfΦRrRrQ), wherein:

F is a L-phenylalanine;
f is a D-phenylalanine;
Φ is an L-2-naphthylalanine;
R is a L-arginine;
r is a D-arginine; and
Q is a L-glutamine.

In some embodiments of the polypeptide conjugate as disclosed herein, the pArg comprises at least five arginine monomers or arginine-analog monomers. In some embodiments, the pArg further comprises at least one cysteine monomer.

In some embodiments, the polypeptide conjugate as disclosed herein has the following structure:

$$\text{CPP-L-[pArg]}_n\text{-L-CPP} \qquad (II)$$

wherein the $[\text{pArg}]_n$ is

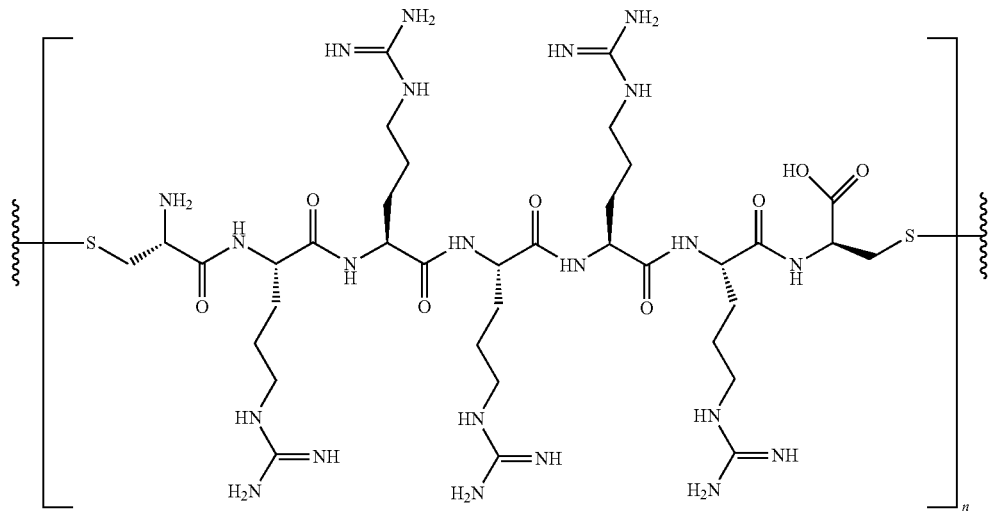

or a charged species thereof.

In some embodiments of the polypeptide conjugate as disclosed herein, n is an integer 1 to 40. In some embodiments of the polypeptide conjugate as disclosed herein, n is an integer 2 to 40. In other embodiments of the polypeptide conjugate as disclosed herein, n is an integer selected from 2 to 30. In other embodiments of the polypeptide conjugate as disclosed herein, n is an integer selected from 2 to 20. In other embodiments of the polypeptide conjugate as disclosed herein, n is an integer selected from 2 to 10.

In some embodiments of the polypeptide conjugate as disclosed herein, at least one L comprises a divalent optionally substituted group selected from amino acid, alkylene, alkenylene, alkynylene, aryl, cycloalkyl, cycloalkenyl, cycloalkynyl, heterocyclyl, heteroaryl, $-(R^1-X-R^2)z-$, or combinations thereof; wherein each of $R^1$ and $R^2$ are independently selected from a bond, alkylene, alkenylene, alkynylene, carbocyclyl, and heterocyclyl, wherein $R^1$ and $R^2$ are not both a bond;

each X is independently N, S, and O; and z is an integer selected from 1 to 20.

In some embodiments of the polypeptide conjugate as disclosed herein, at least one L comprises an optionally substituted $-(O-CH_2CH_2)z-$ or an optionally substituted $-(CH_2CH_2-O)z-$. In some embodiments, at least one L comprises a divalent 8-amino-3,6-dioxaoctanoic acid residue. In other embodiments, at least one L comprises a divalent 8-amino-3,6,9-trioxaundecanoic acid residue.

In some embodiments of the polypeptide conjugate as disclosed herein, at least one L comprises a physiological cleavable group (PCG). In some embodiments, each PCG is, independently, selected from —S—S—, carbonate, thiocarbonate, thioester, sulfoxide, hydrazine, or protease-cleavable dipeptide linker. In other embodiments, each PCG comprises at least one —S—S—.

In some embodiments of the polypeptide conjugate of formula (I) as disclosed herein, at least one of the "—" between L and [P]$_n$ represents a bond between two sulfur atoms (disulfide bond). In other embodiments, the "—" between L and [P]$_n$ each represents a bond between two sulfur atoms (disulfide bond).

In some embodiments of the polypeptide conjugate as disclosed herein, each P, independently, further comprises at least one group selected from:

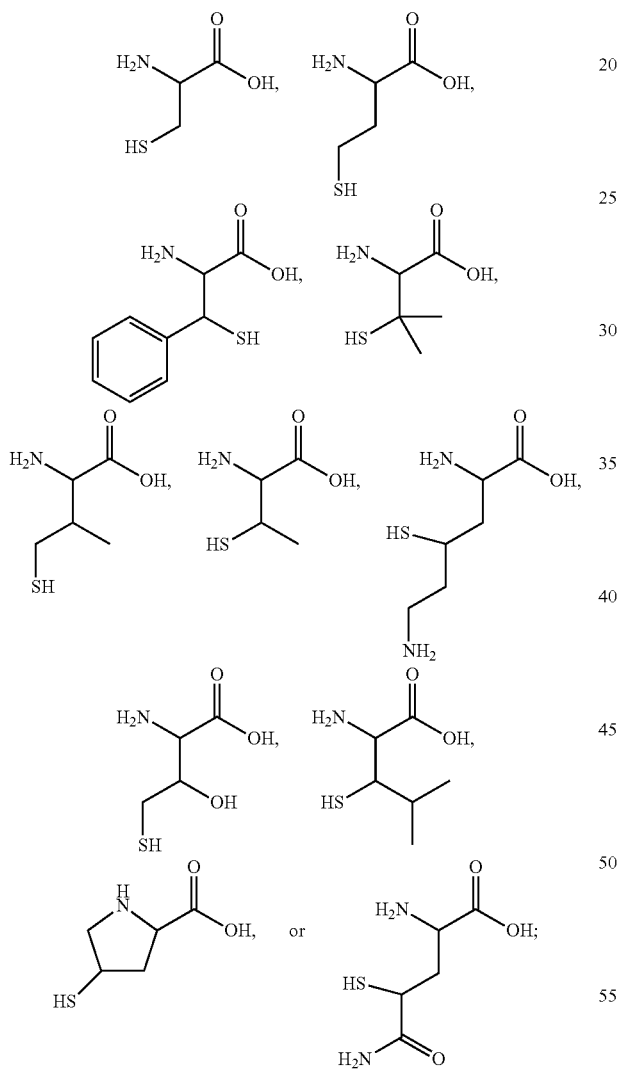

wherein the bond to the hydrogen on at least one of the N- or C-termini is replaced by a bond to the peptide or polyamine; and
wherein the bond to the hydrogen on the thiol group is replaced by a bond to the CPP.

In some embodiments of the polypeptide conjugate as disclosed herein, each P, independently, further comprises at least one group selected from:

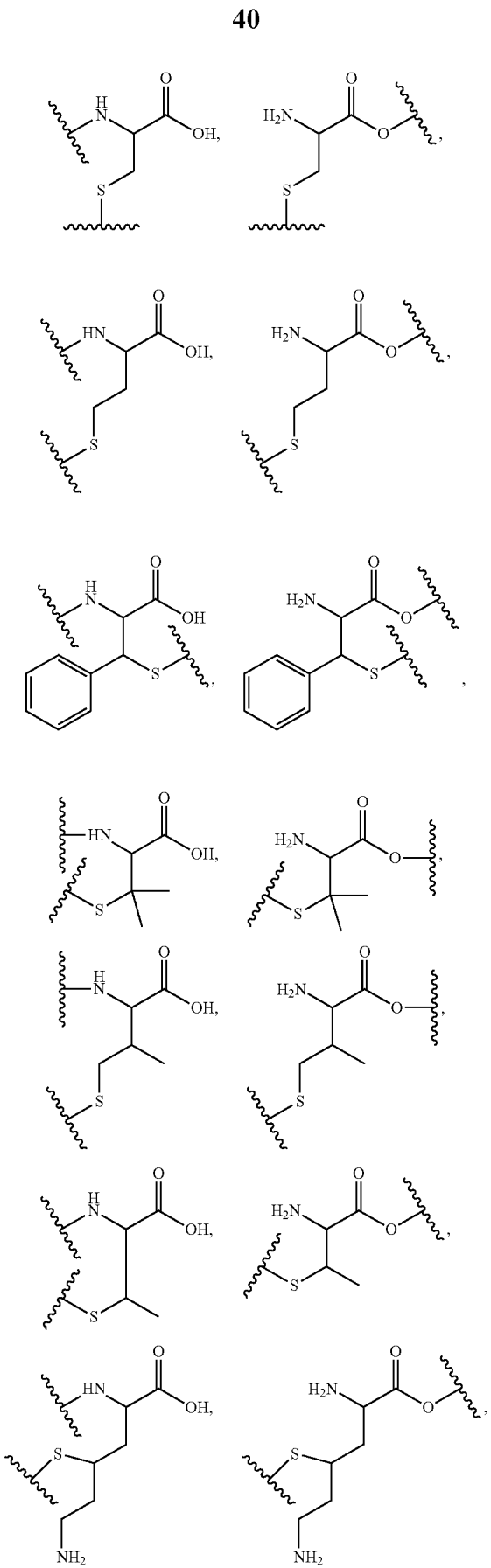

-continued

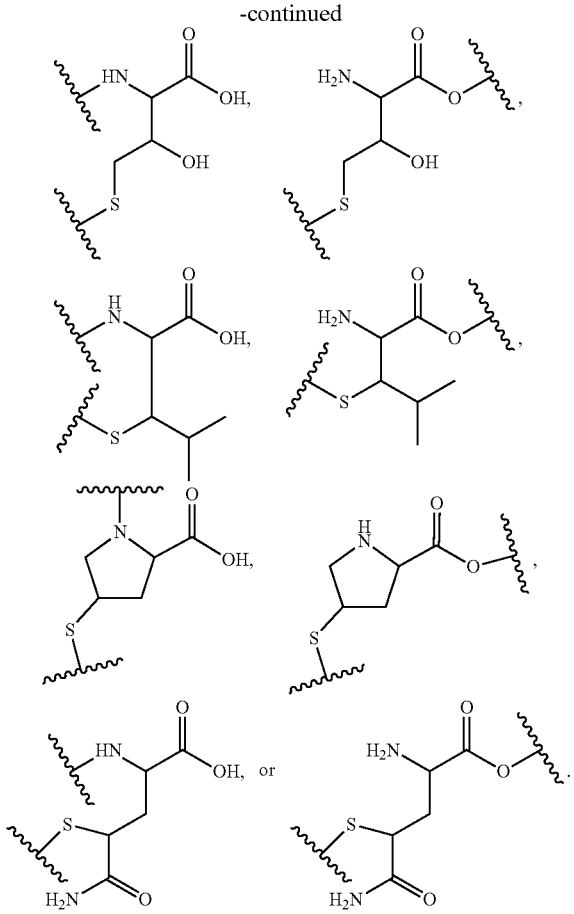

In some embodiments of the polypeptide conjugate as disclosed herein, at least one of the P further comprises

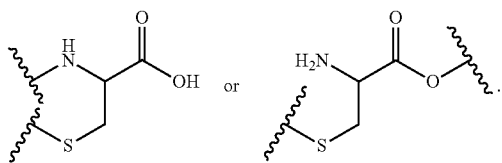 [SMILES: *NC(CS*)C(=O)O ; *OC(=O)C(N)CS*]

In other embodiments, at least one of the P further comprises at least two groups selected from

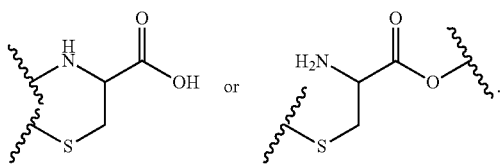 [SMILES: *NC(CS*)C(=O)O ; *OC(=O)C(N)CS*]

In some embodiments, the polypeptide conjugate as disclosed herein has the following structure:

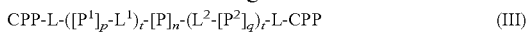

wherein n, p, and q are each independently an integer from 1 to 50;

t is each independently 0 or 1;

$P^1$ and $P^2$ each comprises at least one peptide or polyamine, wherein each peptide comprises at least three monomers selected from arginine, arginine-analog, lysine, lysine-analog, histidine, or histidine-analog, wherein P, $P^1$ and $P^2$, at each occurrence, are same or different; and $L^1$ and $L^2$ are each independently absent or L as defined in claim 1, wherein L, $L^1$, and $L^2$, at each occurrence, are same or different.

In some embodiments of the polypeptide conjugate of formula (III) as disclosed herein, P, $P^1$ or $P^2$ comprises a polyarginine peptide (pArg) comprising at least three monomers selected from arginine or arginine-analog. In some embodiments of the polypeptide conjugate of formula (III) as disclosed herein, P, $P^1$ or $P^2$ comprises a polyarginine peptide (pArg) comprising three monomers selected from arginine or arginine-analog. In other embodiments, P, $P^1$ or $P^2$ comprises a polyamine selected from a spermidine polymer or a spermine polymer.

In some embodiments of the polypeptide conjugate of formula (III) as disclosed herein, P, $P^1$ or $P^2$ comprises mixtures of monomers selected from arginine, arginine-analog, lysine, lysine-analog, histidine, or histidine-analog (e.g., -Arg-Lys-Arg-; -Arg-Arg-His-; etc). In some embodiments of the polypeptide conjugate of formula (III) as disclosed herein, P, $P^1$ or $P^2$ further comprises at least one amino acid monomer (e.g., such as those shown in Table 1).

In some embodiments of the polypeptide conjugate of formula (III) as disclosed herein, at least one of the CPP is a cyclic CPP (cCPP). In other embodiments, the CPP is, each independently, a cyclic CPP (cCPP). In one embodiment, the cCPP comprises from 4 to 14 amino acid monomers. In another embodiment, the cCPP is, each independently, selected from Table 4.

In some embodiments of the polypeptide conjugate of formula (III), the cCPP is a cyclo(fΦRrRrQ) (SEQ ID NO: 118) peptide or a cyclo(FfΦRrRrQ) (SEQ ID NO: 16), wherein:

F is a L-phenylalanine;
f is a D-phenylalanine;
Φ is an L-2-naphthylalanine;
R is a L-arginine;
r is a D-arginine; and
Q is a L-glutamine.

In some embodiments of the polypeptide conjugate of formula (III), the pArg comprises at least three arginine monomers or arginine-analog monomers. In some embodiments of the polypeptide conjugate of formula (III), the pArg comprises three arginine monomers or arginine-analog monomers. In some embodiments of the polypeptide conjugate of formula (III), the pArg comprises at least five arginine monomers or arginine-analog monomers. In other embodiments, the pArg further comprises at least one amino acid monomer (e.g., such as those shown in Table 4). In one embodiment, the pArg further comprises at least one cysteine monomer. In one embodiment, at least one pArg further comprises a thioether moiety (—S—).

In some embodiments of the polypeptide conjugate of formula (III), n is an integer 1 to 40. In some embodiments of the polypeptide conjugate of formula (III), n is an integer 5 to 40.

In some embodiments of the polypeptide conjugate of formula (III), at least one of L, $L^1$, or $L^2$ comprises a divalent optionally substituted group selected from amino acid, polyethylene glycol, alkylene, alkenylene, alkynylene, aryl, cycloalkyl, cycloalkenyl, cycloalkynyl, heterocyclyl, heteroaryl, —($R^1$—X—$R^2$)z-, or combinations thereof;

each of $R^1$ and $R^2$ are independently selected from a bond, alkylene, alkenylene, alkynylene, carbocyclyl, and heterocyclyl, wherein $R^1$ and $R^2$ are not both a bond;

each X is independently N, S, and O; and z is an integer selected from 1 to 20.

In some embodiments of the polypeptide conjugate of formula (III), at least one of L, $L^1$, or $L^2$ comprises an optionally substituted —(O—CH$_2$CH$_2$)z- or an optionally substituted —(CH$_2$CH$_2$—O)z-.

In some embodiments of the polypeptide conjugate of formula (III), at least one of L, $L^1$, or $L^2$ comprises a divalent 8-amino-3,6-dioxaoctanoic acid residue. In some embodiments, at least one of L, $L^1$, or $L^2$ comprises a divalent 8-amino-3,6,9-trioxaundecanoic acid residue. In other embodiments, at least one of L, $L^1$, or $L^2$ comprises a physiological cleavable group (PCG).

In some embodiments of the polypeptide conjugate of formula (III), each PCG is, independently, selected from —S—S—, carbonate, thiocarbonate, thioester, sulfoxide, hydrazine, or protease-cleavable dipeptide linker. In some embodiments, each PCG comprises at least one —S—S—.

In some embodiments of the polypeptide conjugate of formula (III), at least one of the "—" between L and ($[P^1]_p$-$L^1$)$_r$, L and $[P]_n$, or L and ($L^2$-$[P^2]_q$)$_t$ represents a bond between two sulfur atoms (disulfide bond).

In some embodiments of the polypeptide conjugate of formula (III), at least one of P, $P^1$ or $P^2$ further comprises at least one group selected from:

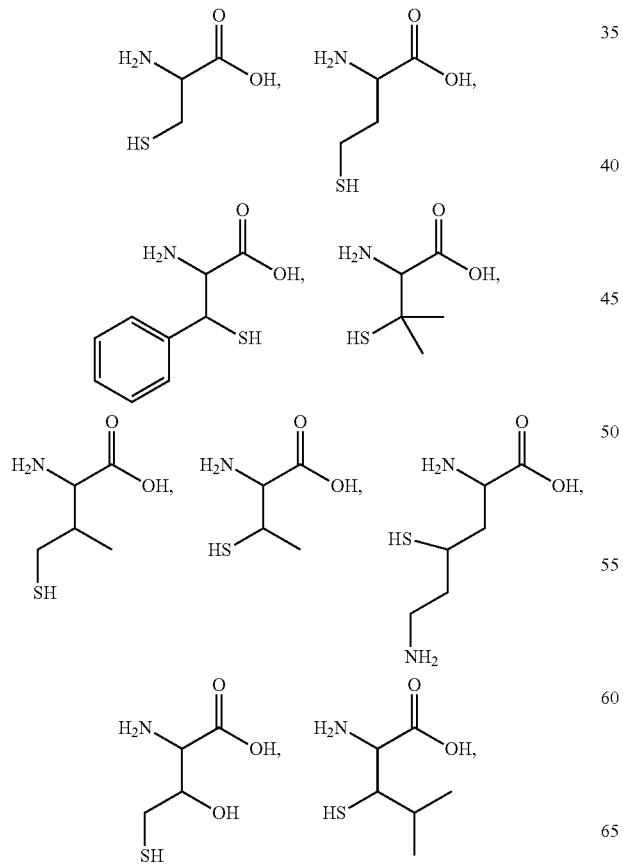

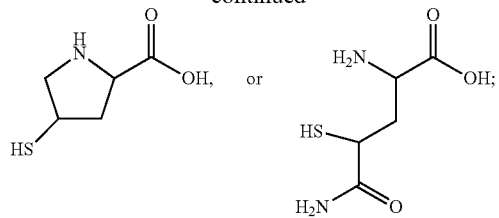

wherein the bond to the hydrogen on at least one of the N- or C-termini is replaced by a bond to the peptide or polyamine; and wherein the bond to the hydrogen on the thiol group is replaced by a bond to the CPP.

In some embodiments of the polypeptide conjugate of formula (III), at least one of P, $P^1$ or $P^2$ further comprises at least one group selected from:

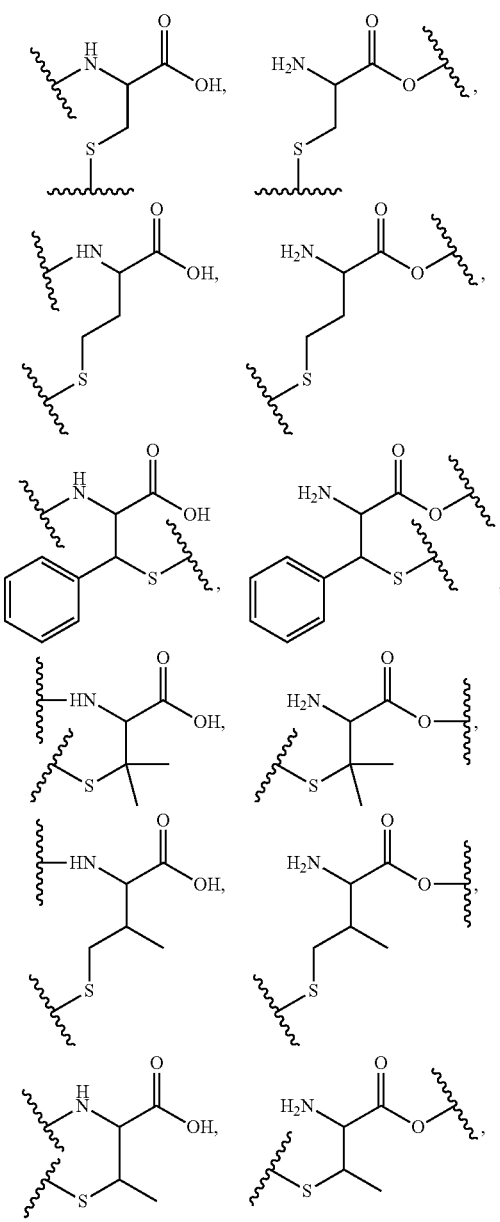

-continued

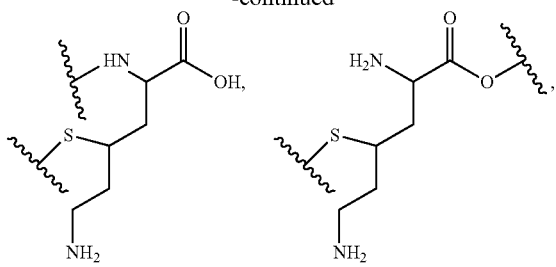

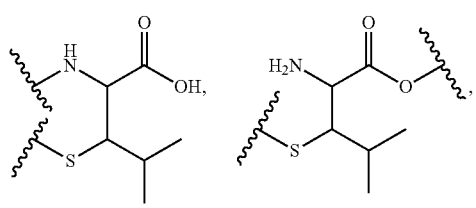

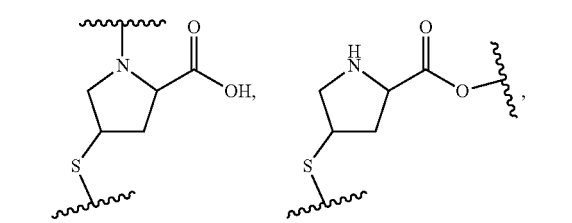

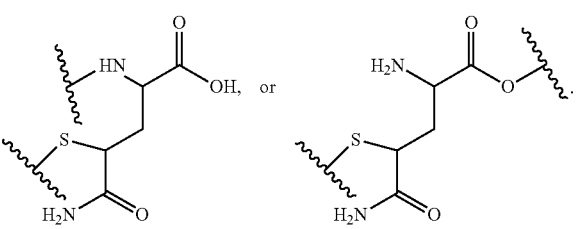

In some embodiments of the polypeptide conjugate of formula (III), at least one of P, $P^1$ or $P^2$ further comprises

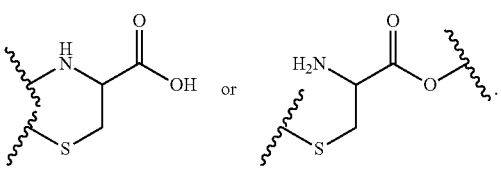 [SMILES: *NC(CS*)C(=O)O ; *OC(=O)C(N)CS*]

In other embodiments, at least at least two of P, $P^1$ or $P^2$ further comprises a group selected form

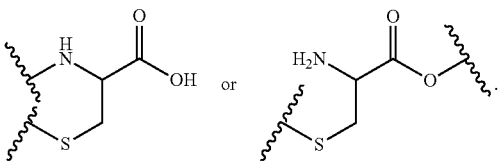 [SMILES: *NC(CS*)C(=O)O ; *OC(=O)C(N)CS*]

In some embodiments of the polypeptide conjugate of formula (III), the pArg further comprises one or more β-alanine monomers. In some embodiments, each pArg comprises, independently, 3, 4, 5, 6, 7, or 8 arginine monomers. In other embodiments, each pArg comprises 3 arginine monomers. In other embodiments, each pArg comprises 5 arginine monomers. In other embodiments, at least one pArg further comprises at least one amino acid monomer (e.g., such as those shown in Table 4). In one embodiment, at least one pArg further comprises a cysteine monomer. In one embodiment, at least one pArg further comprises a thioether moiety (—S—).

In some embodiments of the polypeptide conjugate of formula (III), n, p, and q are each independently an integer from 1 to 40. In other embodiments, n, p, and q are each independently an integer from 1 to 30. In other embodiments, n, p, and q are each independently an integer from 1 to 20. In other embodiments, n, p, and q are each independently an integer from 1 to 10. In other embodiments, n, p, and q are each independently an integer from 1 to 5.

In some embodiments of the polypeptide conjugate of formula (I), (II), or (III) as disclosed herein, P is each independently selected from: -Cys-(Arg)$_x$-Cys- (SEQ ID NO: 131), -Cys-βAla-(Arg)$_x$-Cys- (SEQ ID NO: 132), -Cys-(Arg)$_x$-βAla-Cys- (SEQ ID NO: 133), or -Cys-βAla-(Arg)$_x$-βAla-Cys- (SEQ ID NO: 134), -Cys-(polyamine)$_x$-Cys-, -Cys-βAla-(polyamine)$_x$-Cys-, -Cys-(polyamine)$_x$-βAla-Cys-, -Cys-βAla-(polyamine)$_x$-βAla-Cys- (SEQ ID NO: 135), or —S-(polyamine)$_x$-S—, wherein x=3, 4, 5, 6, 7, or 8.

In some embodiments, the polypeptide conjugate of formula (I) as disclosed herein has the structure
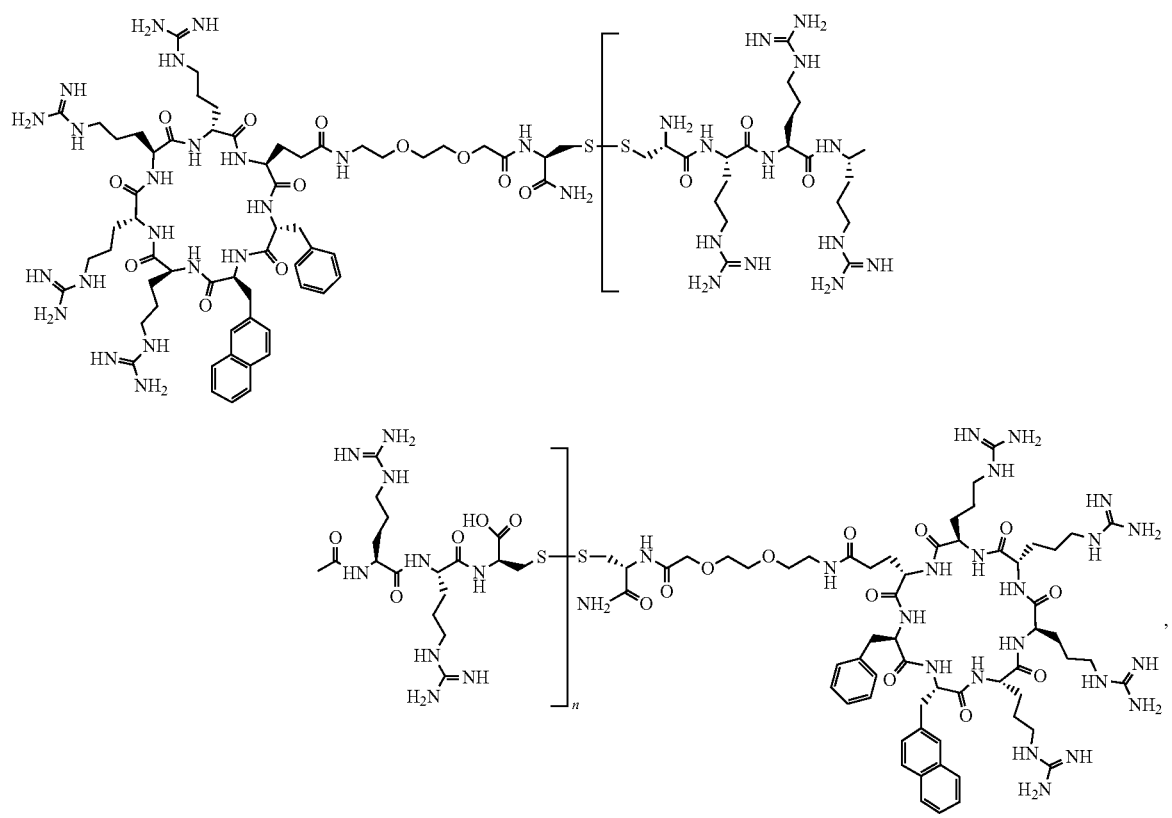
or a charged species thereof.

In some embodiments, the polypeptide conjugate of formula (I) as disclosed herein has the structure

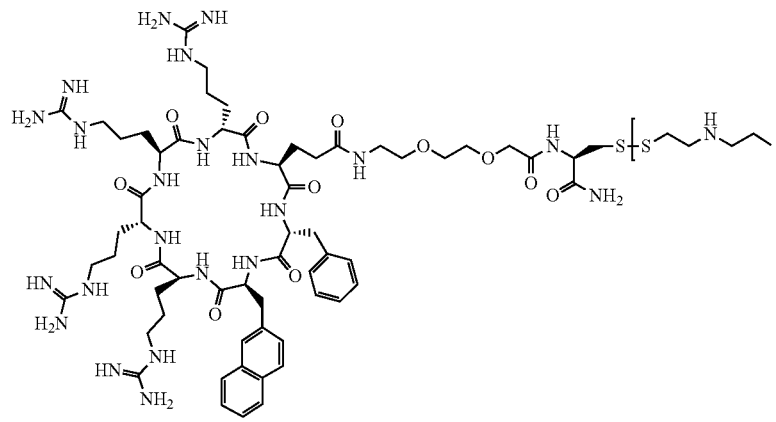

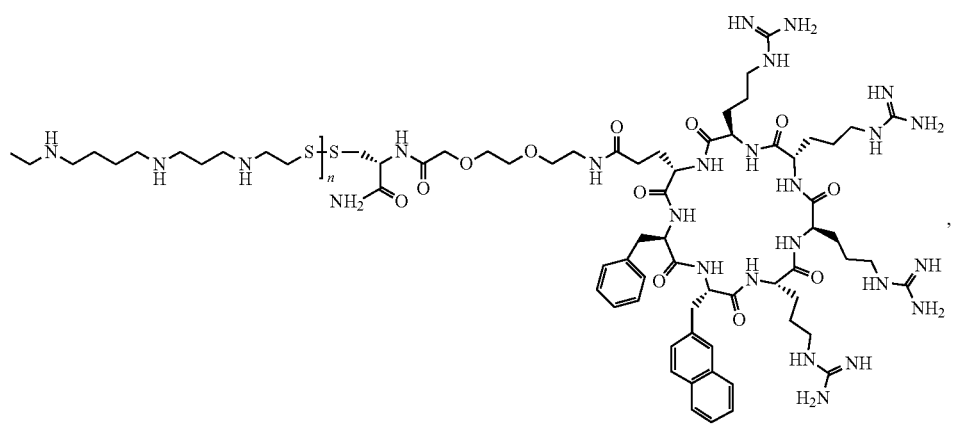

or a charged species thereof.

In some embodiments, the polypeptide conjugate as disclosed herein has the following structure:

wherein:
s is an integer from 1 to 10;
each m is, independently, an integer from 1 to 50; and
wherein P at each occurrence is same or different.

In some embodiments of the polypeptide conjugate of formula (IV) as disclosed herein, P comprises a polyarginine peptide (pArg) comprising at least three monomers selected from arginine or arginine-analog. In some embodiments, P comprises a polyamine selected from a spermidine polymer or a spermine polymer.

In some embodiments of the polypeptide conjugate of formula (IV) as disclosed herein, at least one of the CPP is a cyclic CPP (cCPP). In some embodiments, the cCPP comprises from 4 to 14 amino acid monomers. In other embodiments, the cCPP is, each independently, selected from Table 4.

In some embodiments of the polypeptide conjugate of formula (IV) as disclosed herein, the pArg comprises three arginine monomers or arginine-analog monomers. In some embodiments of the polypeptide conjugate of formula (IV) as disclosed herein, the pArg comprises at least five arginine monomers or arginine-analog monomers. In other embodiments, the pArg further comprises at least one amino acid monomer (e.g., such as those shown in Table 4). In some embodiments, the pArg further comprises at least one cysteine monomer. In one embodiment, the pArg further comprises a cysteine monomer. In one embodiment, at least one pArg further comprises a thioether moiety (—S—).

In some embodiments of the polypeptide conjugate of formula (IV) as disclosed herein, L comprises a divalent optionally substituted group selected from amino acid, polyethylene glycol, alkylene, alkenylene, alkynylene, aryl, cycloalkyl, cycloalkenyl, cycloalkynyl, heterocyclyl, heteroaryl, —(R$^1$—X—R$^2$)z-, or combinations thereof;
each of R$^1$ and R$^2$ are independently selected from a bond, alkylene, alkenylene, alkynylene, carbocyclyl, and heterocyclyl, wherein R$^1$ and R$^2$ are not both a bond;
each X is independently N, S, and O; and
z is an integer selected from 1 to 20.

In some embodiments of the polypeptide conjugate of formula (IV) as disclosed herein, L comprises an optionally substituted —(O—CH$_2$CH$_2$)z- or an optionally substituted —(CH$_2$CH$_2$—O)z-. In some embodiments, L comprises a divalent 8-amino-3,6-dioxaoctanoic acid residue. In other embodiments, L comprises a divalent 8-amino-3,6,9-trioxaundecanoic acid residue. In one embodiment, L comprises a physiological cleavable group (PCG).

In some embodiments of the polypeptide conjugate of formula (IV) as disclosed herein, each PCG is, independently, selected from —S—S—, carbonate, thiocarbonate, thioester, sulfoxide, hydrazine, or protease-cleavable dipeptide linker. In some embodiments, each PCG comprises at least one —S—S—.

In some embodiments of the polypeptide conjugate of formula (IV) as disclosed herein, L comprises a polythiolamine or a 3,5-bis(mercaptomethyl)benzoyl (Bmb) amide.

In some embodiments of the polypeptide conjugate of formula (IV), L comprises two or more physiological cleavable groups.

In some embodiments of the polypeptide conjugate of formula (IV) as disclosed herein, the "—" between L and ([P]$_m$)$_s$ represents a bond between two sulfur atoms (disulfide bond).

In some embodiments of the polypeptide conjugate of formula (IV) as disclosed herein, each P, independently, further comprises at least one group selected from:

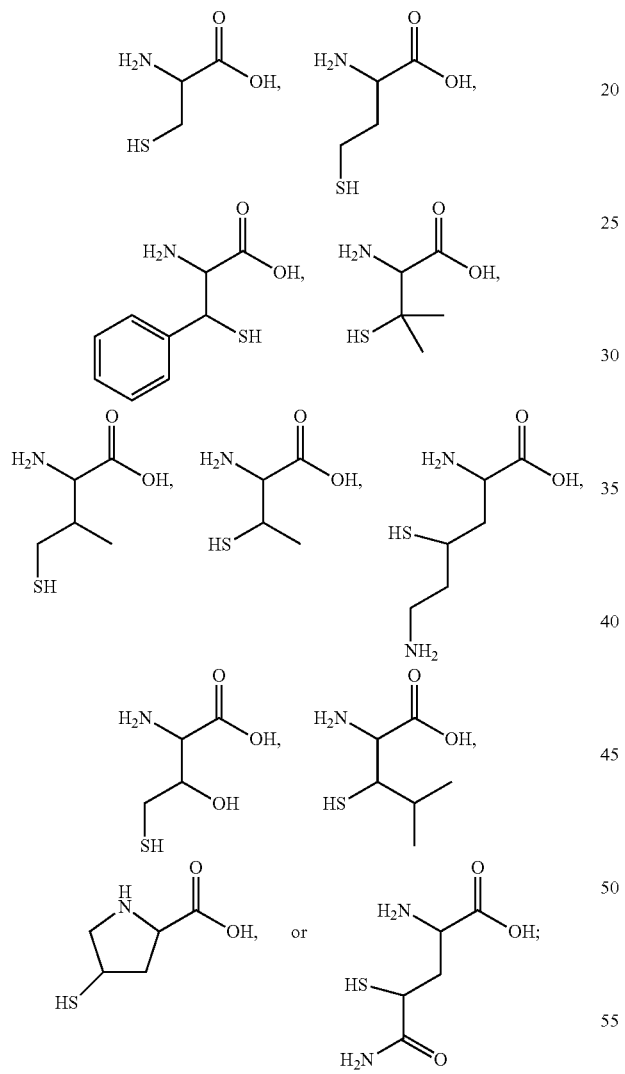

wherein the bond to the hydrogen on one at least one of the N- or C-termini is replaced by a bond to the peptide or polyamine; and
wherein the bond to the hydrogen on the thiol group is replaced by a bond to the CPP.

In some embodiments of the polypeptide conjugate of formula (IV) as disclosed herein, each P, independently, further comprises at least one group selected from:

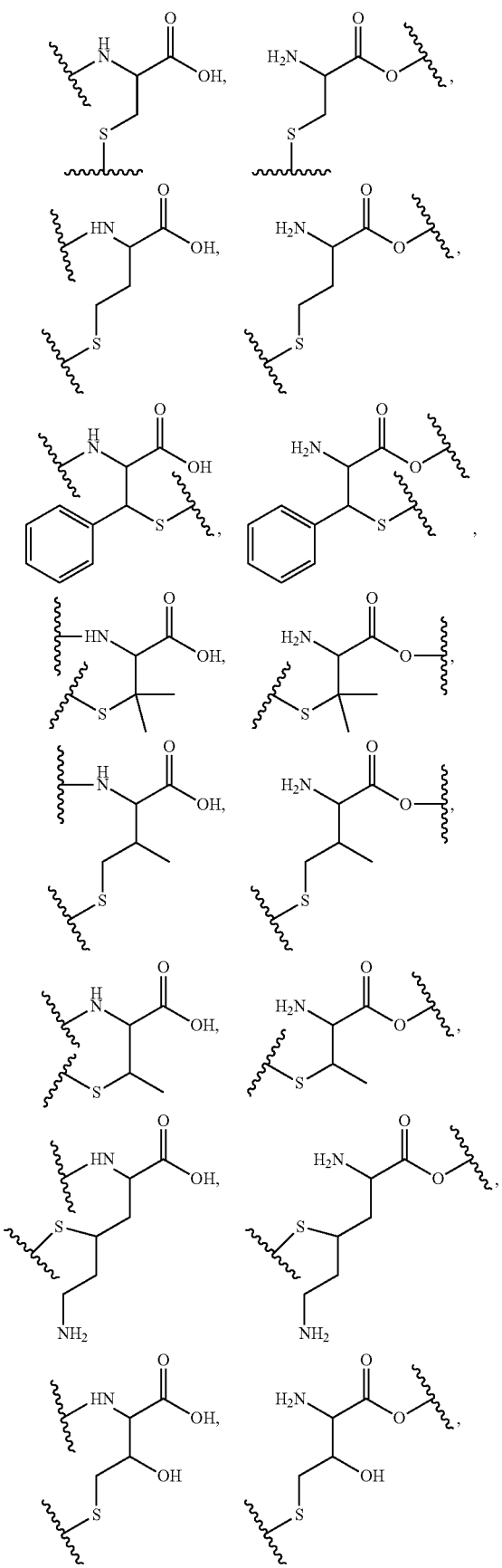

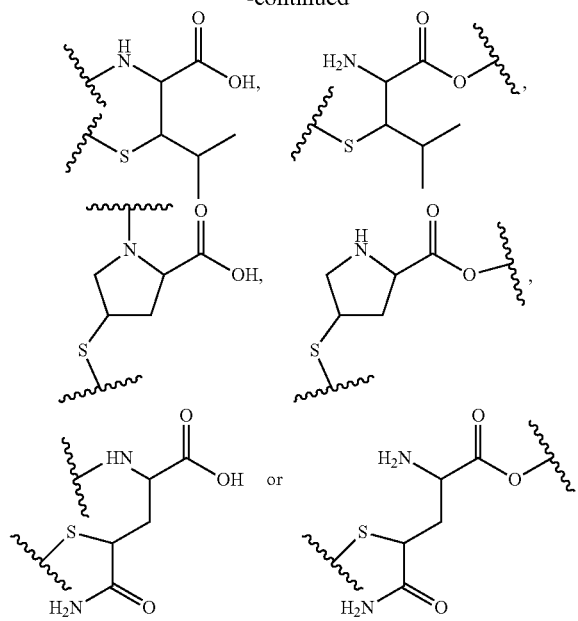

In some embodiments of the polypeptide conjugate of formula (IV) as disclosed herein, at least one of the P further comprises

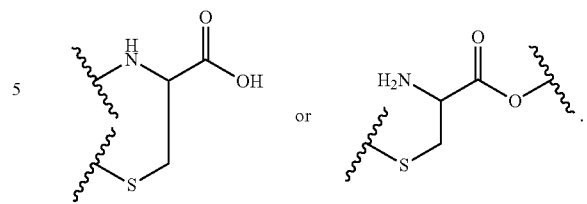

In other embodiments, at least one of the P further comprises at least two groups selected form

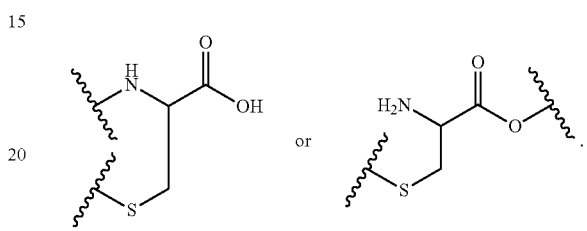

In some embodiments of the polypeptide conjugate of formula (IV) as disclosed herein, s is 2, 3, 4, or 5.

In some embodiments, the polypeptide conjugate of formula (IV) as disclosed herein has the structure

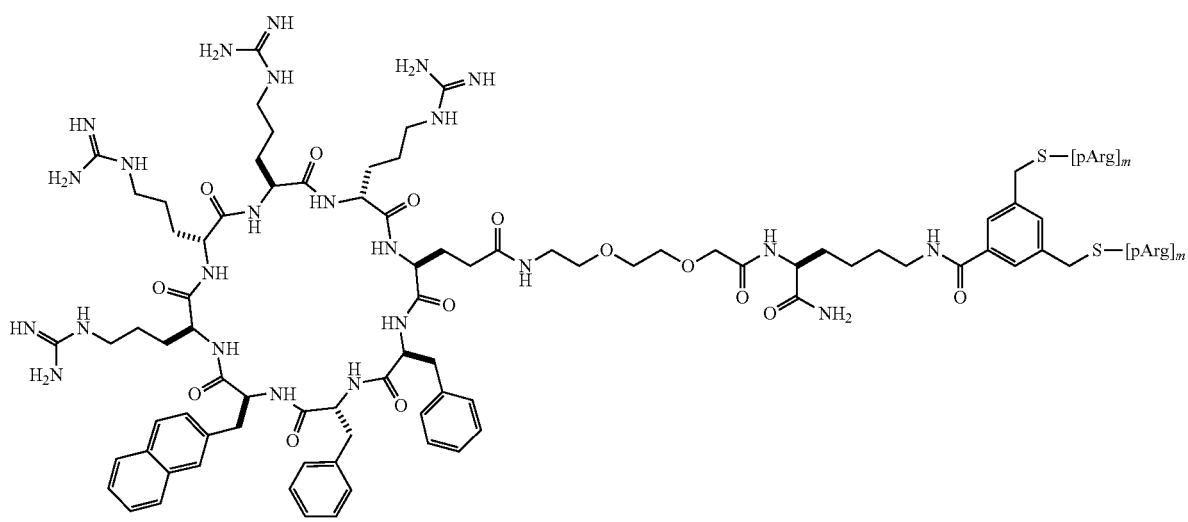

or charged species thereof.

In some embodiments, the polypeptide conjugate of formula (IV) as disclosed herein has the structure

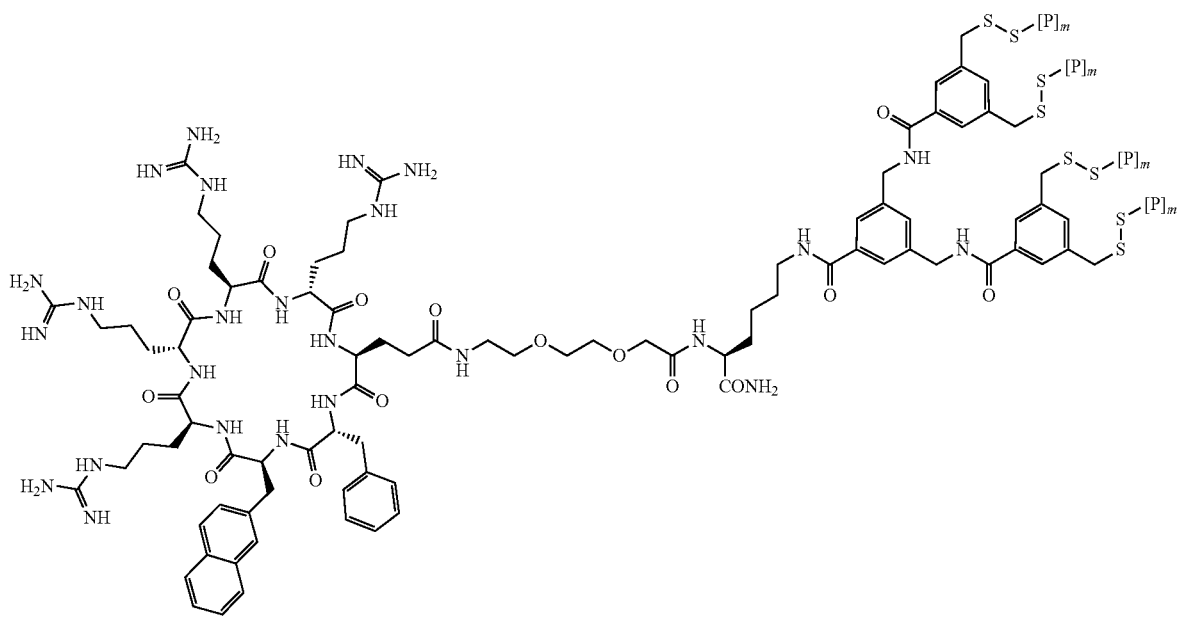

or charged species thereof.

In some embodiments, the polypeptide conjugate as disclosed herein has the following structure:

wherein,
cCPP is a cyclic CPP; and
n is an integer selected from 1 to 50;
m is an integer selected from 0 to 49 provided that the sum of n and m is 50 or less;
v is 0 or 1;

wherein P at each occurrence is same or different; and
wherein when v is 0, the last [P] in [P]$_m$ is monovalent.

In some embodiments of the polypeptide conjugate of formula (V), v is 1.

In some embodiments of the polypeptide conjugate of formula (V) as disclosed herein, the "—" between [P]$_n$ and [P]$_m$ represents a bond between two sulfur atoms (a disulfide bond).

In some embodiments, the polypeptide conjugate of formula (IV) as disclosed herein, has the following structure:

(VI)
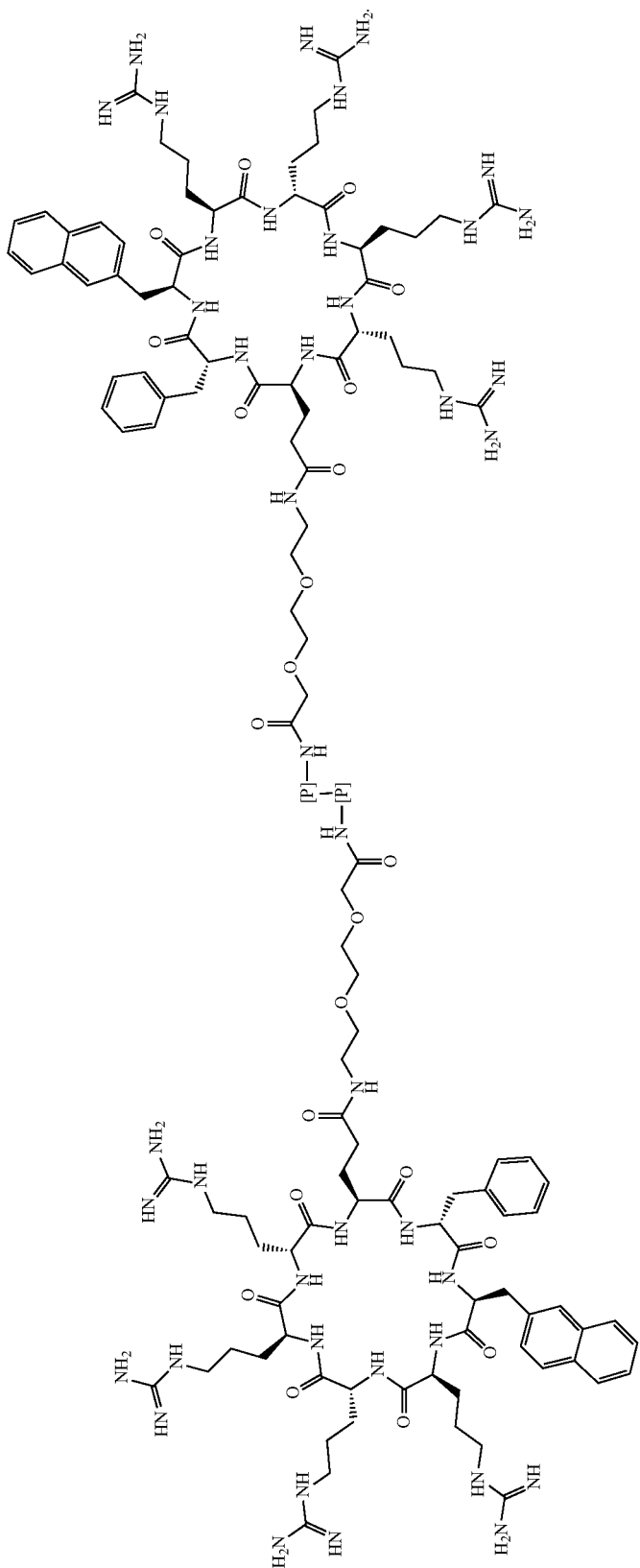

In some embodiments of the polypeptide conjugate of formula (VI) as disclosed herein, the "—" between [P] and [P] represents a bond between two sulfur atoms (a disulfide bond).

In some embodiments, the polypeptide conjugate as disclosed herein has the following structure:

cCPP-L-[P]$_n$-[P]$_m$-[P]$_o$-(L-cCPP)  (VII)

wherein,
cCPP is a cyclic CPP; and
n is an integer selected from 1 to 50;
m and o, are each independently, an integer from 0 to 49 provided that the sum of n, m, and o is 50 or less;
v is 0 or 1;
wherein P at each occurrence is same or different; and
wherein when v is 0, the last [P] in [P]$_o$ is monovalent.

In some embodiments of the polypeptide conjugate of formula (VII), v is 1.

In some embodiments of the polypeptide conjugate of formula (VII) as disclosed herein, at least one of the "—" between n an [P]$_m$ or [P]$_m$ and [P]$_o$ represents a bond between two sulfur atoms (a disulfide bond). In other embodiments, the "—" between [P]$_n$ and [P]$_m$ and between [P]$_m$ and [P]$_o$ represents a bond between two sulfur atoms (a disulfide bond).

In some embodiments, the polypeptide conjugate of formula (VI) as disclosed herein, has the following structure:

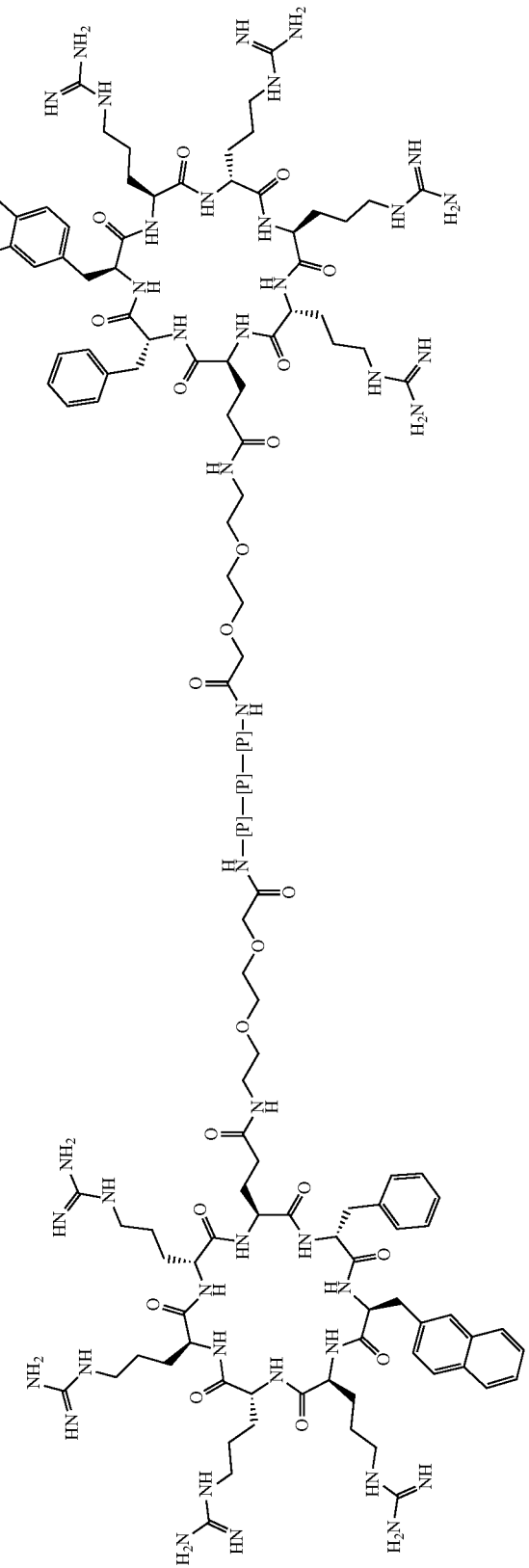

In some embodiments of the polypeptide conjugate of formula (VIII) as disclosed herein, at least one of the "—" between [P] and [P] represents a bond between two sulfur atoms (a disulfide bond). In other embodiment, each "—" between [P] and [P] represents a bond between two sulfur atoms (a disulfide bond).

In some embodiment, the dash "—" between P (including $P^1$ and $P^2$), L (including $L^1$ and $L^2$), and CPP (including cCPP) in formula (I), (II), (III), (IV), (V), (VI), (VII), and (VIII) represents each component's spatial orientation. To be clear, "—" not strictly as a C—C bond, although in some embodiments, it may be. In some embodiments, each P can be discussed as its own component having a chemical group necessary to covalently attach to L. In some embodiments, each P can be discussed as its own component having a chemical group necessary to covalently attach to another group of P. In some embodiments, the CPP can be discussed as its own component having a chemical group necessary to covalently attach to L. One skilled in the art would readily understand how each component, described separately, can covalently attach to one another to provide the polypeptide conjugate as disclosed herein.

In some embodiments, any of L (including $L^1$ and $L^2$) disclosed herein can be the linker that is covalently attached to P and/or to the CPP. In some embodiments, any of L disclosed herein can describe the linker moiety before covalently attaching it to P and/or to CPP. In a non-limited example, L can comprise a chemical group (e.g., —SH, —NH$_2$, —OH etc) which can be reacted with another chemical group on or attached to P or CPP in order to form a covalent bond, e.g., disulfide bond (—S—S—), amine bond (—NH—), ether bond (—O—), amide bond (—NH(O)—), ester bond (—C(O)O—), etc. In one embodiment, a chemical group already present in L as described herein can be used to covalently attach L to the P and/or to the CPP. The chemistry used to covalently attach P to L and L to CPP can be readily understood by one skilled in the art.

In one embodiment, any of L disclosed herein can further comprise a chemical group useful in covalently attaching L to the P and/or to the CPP.

Cell-Penetrating Peptides (CPP)

As discussed above, the polypeptide conjugates disclosed herein comprise cell-penetrating peptides (CPPs). CPPs are peptides that facilitate cellular intake or uptake of various molecular equipment, often refers to as a "cargo" (e.g., nucleic acid or siRNA). The "cargo" is associated with the peptides through non-covalent interactions, such as by electrostatic interactions. The function of the CPPs are to deliver the cargo into cells, a process that commonly occurs through endocytosis and subsequently released into cytosol of mammalian cells.

(i) CPPs typically have an amino acid composition that either contains a high relative abundance of positively charged amino acids such as arginine or has sequences that contain an alternating pattern of polar/charged amino acids and non-polar, hydrophobic amino acids. Some CPPs comprise hydrophobic peptides, containing only apolar residues, with low net charge or have hydrophobic amino acid groups that are crucial for cellular uptake. Non-limiting examples of linear CPPs include Polyarginine (e.g., $R_9$ or $R_{11}$), Antennapedia sequences, HIV-TAT, Penetratin, Antp-3A (Antp mutant), Buforin II. Transportan, MAP (model amphipathic-peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In some embodiments, CPPs are cyclic CPPs (cCPPs). The cCPP may be or include any amino sequence, which facilitates cellular uptake of the polypeptide conjugates disclosed herein. Suitable cCPPs for use in the polypeptide conjugates and methods described herein can include naturally occurring sequences, modified sequences, and synthetic sequences. In embodiments, the total number of amino acids in the cCPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the cCPPs disclosed herein comprise about 4 to about to about 13 amino acids. In particular embodiments, the CPPs disclosed herein comprise about 6 to about 10 amino acids, or about 6 to about 8 amino acids.

Each amino acid in the CPP or cCPP may be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allosoleucine | Alle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| glutamine | Gln (Q) | gln (q) |
| glycine | Gly (G) | gly (g) |
| histidine | His (H) | his (h) |
| Homoproline (aka pipecolic acid) | Pip (Θ) | pip (θ) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe (f) |
| phenylglycine | Phg (Ψ) | phg |
| 4-(phosphonodifluoromethyl)phenylalanine | F$_2$Pmp (A) | f$_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| valine | Val (V) | val (v) |

*single letter abbreviations: when shown in capital letters herein it indicates the L-amino acid In some embodiments, the cCPPs may include any combination of at least two arginines and at least two hydrophobic amino acids. In some embodiments, the cCPPs may include any combination of two to three arginines and at least two hydrophobic amino acids.

In some embodiments, the CPP used in polypeptide conjugates described herein $$(AA_u)_m\text{-}AA_1\text{-}AA_2\text{-}AA_3\text{-}AA_4\text{-}(AA_z)_n$$

has a structure comprising Formula 1:1
wherein:
each of $AA_1$, $AA_2$, $AA_3$, and $AA_4$, are independently selected from a D or L amino acid,
each of $AA_u$ and $AA_z$, at each instance and when present, are independently selected from a D or L amino acid, and
m and n are independently selected from a number from 0 to 6.

In some embodiments of the Formula 1, at least two of $AA_u$ (when present), $AA_1$, $AA_2$, $AA_3$, $AA_4$, and $AA_5$ (when present), are independently arginine. In some embodiments, at least two of $AA_u$ (when present), $AA_1$, $AA_2$, $AA_3$, $AA_4$, and $AA_z$ (when present), are independently an amino acid having a hydrophobic side chain. In some embodiments, at least two of $AA_u$ (when present), $AA_1$, $AA_2$, $AA_3$, $AA_4$, and $AA_z$ (when present), are independently arginine and at least two of $AA_u$ (when present), $AA_1$, $AA_2$, $AA_3$, $AA_4$, and $AA_z$ (when present), are independently an having a hydrophobic side chain.

In some embodiments, each amino acid having a hydrophobic side chain is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each amino acid having a hydrophobic side chain is independently an amino acid having a hydrophobic aromatic side chain. In some embodiments, the amino acid having a hydrophobic aromatic side chain is naphthylalanine, phenylglycine, homophenylalanine, phenylalanine, tryptophan, or tyrosine, each of which is optionally substituted with one or more substituents. In particular embodiments, the amino acid having a hydrophobic side chain is piperidine-2-carboxylic acid, naphthylalanine, tryptophan, or phenylalanine, each of which is optionally substituted with one or more substituents.

The optional substituent can be any atom or group which does not significantly reduce the cytosolic delivery efficiency of the CPP or cCPP, e.g., a substituent that does not reduce relative cytosolic delivery efficiency to less than that of c(FΦRRRRQ) (SEQ ID NO: 9). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a CPP relative to amino acids having a lower hydrophobicity value. In some embodiments, each hydrophobic amino acid independently has a hydrophobicity value which is greater than that of glycine. In other embodiments, each hydrophobic amino acid independently is hydrophobic amino acid having a hydrophobicity value which is greater than that of alanine. In still other embodiments, each hydrophobic amino acid independently has a hydrophobicity value which is greater or orequal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev, of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

Hydrophobicity Values of Amino Acids

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the CPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to an amino acid having a hydrophobic side chain. In some embodiments, the arginine has the same chirality as the amino acid having a hydrophobic side chain. In some embodiments, at least two arginines are adjacent to each other. In still other embodiments, three arginines are adjacent to each other. In some embodiments, at least two amino acids each having a hydrophobic side chain are adjacent to each other. In other embodiments, at least three amino acids each having a hydrophobic side chain are adjacent to each other. In other embodiments, the CPPs described herein comprise at least two consecutive amino acids each having a hydrophobic side chain and at least two consecutive arginines. In further embodiments, one hydrophobic amino acid is adjacent to one of the arginines. In still other embodiments, the CPPs described herein comprise at least three consecutive amino acids each having a hydrophobic side chain and there consecutive arginines. In further embodiments, one hydrophobic amino acid is adjacent to one of the arginines. These various combinations of amino acids can have any arrangement of D and L amino acids, e.g., the sequences described above. As used herein, adjacent refers to amino acids that are coupled to each other through a peptide bond.

In some embodiments, any four adjacent amino acids in the CPPs described herein can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently an amino acid having a hydrophobic side chain. Accordingly, in some embodiments, the CPPs used in the polypeptide conjugates described herein have a structure according any of Formula 2A-2D: $(AA_u)_m$-$AA_{H2}$-$AA_{H1}$-R-r-$(AA_z)_n$  $(AA_u)_m$-r-R-$AA_{H1}$-$AA_{H2}$-$(AA_z)_n$ $(AA_u)_m$-$AA_{H2}$-$AA_{H1}$-r-R-$(AA_z)_n$ 2A 2B 2C $(AA_u)_m$-R-r-$AA_{H1}$-$AA_{H2}$-$(AA_z)_n$ and 2D wherein:
each of $AA_{H1}$ and $AA_{H2}$ are independently an amino acid having a hydrophobic side chain;
at each instance and when present, each of $AA_u$ and $AA_z$ are independently any amino acid; and
m and n are independently selected from a number from 0 to 6.

In some embodiments, the total number of amino acids (including r, R, $AA_{H1}$, $AA_{H2}$), in the CPPs of Formula 2A to 2D are in the range of 6 to 10. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments of Formula 2A-2D, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each amino acid having a hydrophobic side chain is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each amino acid having a hydrophobic side chain is independently an amino acid having a hydrophobic side chain. In some embodiments, the aromatic hydrophobic amino acid is naphthylalanine, phenylglycine, homophenylalanine, phenylalanine, tryptophan, or tyrosine, each of which is optionally substituted with one or more substituents. In particular embodiments, the amino acid having a hydrophobic side chain is piperidine-2-carboxylic acid, naphthylalanine, tryptophan, or phenylalanine, each of which is optionally substituted with one or more substituents.

In some embodiments of Formula 2A-2D, each of $AA_{H1}$ and $AA_{H2}$ are independently an amino acid having a hydrophobic side chain with a hydrophobicity value which is greater than that of glycine. In other embodiments, each of $AA_{H1}$ and $AA_{H2}$ are independently an amino acid having a hydrophobic side chain with a hydrophobicity value which is greater than that of alanine. In still other embodiments, each of $AA_{H1}$ and $AA_{H2}$ are independently an amino acid having a hydrophobic side chain with a hydrophobicity value which is greater than that of phenylalanine, e.g., as measured using the hydrophobicity scales described above, including Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of an amino acid having a hydrophobic side chain on the N- or C-terminal of a D-Arg or L-Arg, or a combination thereof, has also found to improve the cytosolic uptake of the CPP (and the attached cargo). For example, in some embodiments, the CPPs (including cCPPs) disclosed herein may include $AA_{H1}$-D-Arg or D-Arg-$AA_{H1}$. In other embodiments, the CPPs disclosed herein may include $AA_{H1}$-L-Arg or L-Arg-$AA_{H1}$.

The size of the hydrophobic chain of the amino acid on the N- or C-terminal of the D-Arg or an L-Arg, or a combination thereof (i.e., $AA_{H1}$), may be selected to improve cytosolic delivery efficiency of the CPP. For example, a larger hydrophobic chain on an amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine.

In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$_2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AA_{H1}$.

By way of example, and not by limitation, a cCPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical cCPP having a Nal-Phe-Arg motif; and a phe-Nal-Arg motif exhibits improved cytosolic delivery efficiency compared to an otherwise identical cCPP having a nal-Phe-Arg motif.

As used herein, "hydrophobic surface area" or "SASA" refers to the surface area (reported as square Ångstroms; Å$^2$) of an amino acid side chain that is accessible to a solvent. In particular embodiments, SASA is calculated using the 'rolling ball' algorithm developed by Shrake & Rupley (*J. Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635, which is herein incorporated by reference in its entirety for all purposes.

TABLE 3

SASA Values of Amino Acid Side Chains

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the CPP does not include an amino acid with a hydrophobic side chain on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the CPP does not include an amino acid having a hydrophobic side chain which is larger (as described herein) than at least one of $AA_{H1}$ or $AA_{H2}$. In further embodiments, the CPP does not include an amino acid with a hydrophobic side chain having a surface area greater than $AA_{H1}$. For example, in embodiments in which at least one of $AA_{H1}$ or $AA_{H2}$ is phenylalanine, the cPP does not further include a naphthylalanine (although the CPP include at least one amino acid with a hydrophobic side chain that is smaller than $AA_{H1}$ and $AA_{H2}$, e.g., leucine). In still other embodiments, the CPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the CPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-Arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the CPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_{H}$ can be D-nal, D-trp, or D-phe. In another non-limiting example, when arginine is L-Arg, $AA_H$ can be L-Nal, L-Trp, or L-Phe.

In some embodiments, the CPPs (including cCPPs) described herein include three arginines. Accordingly, in some embodiments, the CPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the CPPS have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the CPPs described herein include at least three amino acids having a hydrophobic side chain. Accordingly, in some embodiments, the CPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any amino acid having a hydrophobic side chain described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SASA of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the CPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-$AA_{H1}$ and L-$AA_{H2}$ is L-Nal. In other particular embodiments, L-$AA_{H1}$ is L-Nal.

As discussed above, the disclosure provides for various modifications to a cyclic peptide sequence which may improve cytosolic delivery efficiency. In some embodiments, improved cytosolic uptake efficiency can be measured by comparing the cytosolic delivery efficiency of the polypeptide conjugate or complex of the present disclosure having the modified sequence to a proper control sequence. In some embodiments, the control sequence does not include a particular modification (e.g., matching chirality of R and $AA_{H1}$) but is otherwise identical to the modified sequence. In other embodiments, the control has the following sequence: cyclic(FΦRRRRQ)

As used herein cytosolic delivery efficiency refers to the ability of a polypeptide conjugate or complex of the present disclosure to traverse a cell membrane and enter the cytosol. In embodiments, cytosolic delivery efficiency of the CPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a polypeptide conjugate or complex of the present disclosure over the concentration of the polypeptide conjugate or complex of the present disclosure in the growth medium. Relative cytosolic delivery efficiency refers to the concentration of a polypeptide conjugate or complex of the present disclosure in the cytosol compared to the concentration of a control polypeptide conjugate or complex of the present disclosure in the cytosol. Quantification can be achieved by fluorescently labeling the polypeptide conjugate or complex of the present disclosure (e.g., with a FTIC dye) and measuring the fluorescence intensity using techniques well-known in the art.

In particular embodiments, relative cytosolic delivery efficiency is determined by comparing (i) the amount of a polypeptide conjugate or complex of the present disclosure internalized by a cell type (e.g., HeLa cells) to (ii) the amount of the polypeptide conjugate or complex of the present disclosure internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the polypeptide conjugate or complex of the present disclosure internalized by the cell is quantified using methods known in the art, e.g., fluorescence microscopy. Separately, the same concentration of the control is incubated in the presence of the cell type over the same period of time, and the amount of the control internalized by the cell is quantified.

Non-limiting examples of suitable cyclic cell penetrating peptide are provided in Table 4.

TABLE 4

Examples of Cyclic Cell-Penetrating Peptides (cCPPs)

| ID | cCPP Sequence | SEQ ID NO |
|---|---|---|
| PCT 1 | cyclo(FΦRRRQ) | 1 |
| PCT 2 | cyclo(FΦRRRC) | 2 |
| PCT 3 | cyclo(FΦRRRU) | 3 |
| PCT 4 | cyclo(RRRΦFQ) | 4 |
| PCT 5 | cyclo(RRRRΦF) | 5 |

TABLE 4-continued

Examples of Cyclic Cell-Penetrating Peptides (cCPPs)

| ID | cCPP Sequence | SEQ ID NO |
|---|---|---|
| PCT 6 | cyclo(FΦRRRR) | 6 |
| PCT 7 | cyclo(FϕrRrRq) | 7 |
| PCT 8 | cyclo(FϕrRrRQ) | 8 |
| PCT 9 | cyclo(FΦRRRRQ) | 9 |
| PCT 10 | cyclo(fΦRrRrQ) | 10 |
| PCT 11 | cyclo(RRFRΦRQ) | 11 |
| PCT 12 | cyclo(FRRRRΦQ) | 12 |
| PCT 13 | cyclo(rRFRΦRQ) | 13 |
| PCT 14 | cyclo(RRΦFRRQ) | 14 |
| PCT 15 | cyclo(CRRRRFWQ) | 15 |
| PCT 16 | cyclo(FfΦRrRrQ) | 16 |
| PCT 17 | cyclo(FFΦRRRRQ) | 17 |
| PCT 18 | cyclo(RFRFRΦRQ) | 18 |
| PCT 19 | cyclo(URRRRFWQ) | 19 |
| PCT 20 | cyclo(CRRRRFWQ) | 20 |
| PCT 21 | cyclo(FΦRRRRQK) | 21 |
| PCT 22 | cyclo(FΦRRRRQC) | 22 |
| PCT 23 | cyclo(fΦRrRrRQ) | 23 |
| PCT 24 | cyclo(FΦRRRRRQ) | 24 |
| PCT 25 | cyclo(RRRRΦFDΩC) | 25 |
| PCT 26 | cyclo(FΦRRR) | 26 |
| PCT 27 | cyclo(FWRRR) | 27 |
| PCT 28 | cyclo(RRRΦF) | 28 |
| PCT 29 | cyclo(RRRWF) | 29 |
| SAR 1 | cyclo(FΦRRRRQ) | 30 |
| SAR 19 | cyclo(FFRRRQ) | 31 |
| SAR 20 | cyclo(FFrRrQ) | 32 |
| SAR 21 | cyclo(FFRrRQ) | 33 |
| SAR 22 | cyclo(FRFRRQ) | 34 |
| SAR 23 | cyclo(FRRFRQ) | 35 |
| SAR 24 | cyclo(FRRRFQ) | 36 |
| SAR 25 | cyclo(GΦRRRQ) | 37 |
| SAR 26 | cyclo(FFFRAQ) | 38 |
| SAR 27 | cyclo(FFFRRQ) | 39 |
| SAR 28 | cyclo(FFRRRRQ) | 40 |
| SAR 29 | cyclo(FRRFRRQ) | 41 |
| SAR 30 | cyclo(FRRRFRQ) | 42 |

TABLE 4-continued

Examples of Cyclic Cell-Penetrating Peptides (cCPPs)

| ID | cCPP Sequence | SEQ ID NO |
|---|---|---|
| SAR 31 | cyclo(RFFRRRQ) | 43 |
| SAR 32 | cyclo(RFRRFRQ) | 44 |
| SAR 33 | cyclo(FRFRRRQ) | 45 |
| SAR 34 | cyclo(FFFRRRQ) | 46 |
| SAR 35 | cyclo(FFRRRFQ) | 47 |
| SAR 36 | cyclo(FRFFRRQ) | 48 |
| SAR 37 | cyclo(RRFFFRQ) | 49 |
| SAR 38 | cyclo(FFRFRRQ) | 50 |
| SAR 39 | cyclo(FFRRRFQ) | 51 |
| SAR 40 | cyclo(FRRFFRQ) | 52 |
| SAR 41 | cyclo(FRRFRFQ) | 53 |
| SAR 42 | cyclo(FRFRFRQ) | 54 |
| SAR 43 | cyclo(RFFRFRQ) | 55 |
| SAR 44 | cyclo(GΦRRRRQ) | 56 |
| SAR 45 | cyclo(FFFRRRRQ) | 57 |
| SAR 46 | cyclo(RFFRRRRQ) | 58 |
| SAR 47 | cyclo(RRFFRRRQ) | 59 |
| SAR 48 | cyclo(RFFFRRRQ) | 60 |
| SAR 49 | cyclo(RRFFFRRQ) | 61 |
| SAR 50 | cyclo(FFRRFRRQ) | 62 |
| SAR 51 | cyclo(FFRRRRFQ) | 63 |
| SAR 52 | cyclo(FRRFFRRQ) | 64 |
| SAR 53 | cyclo(FFFRRRRRQ) | 65 |
| SAR 54 | cyclo(FFFRRRRRRQ) | 66 |
| SAR 55 | cyclo(FΦRrRrQ) | 67 |
| SAR 56 | cyclo(XXRRRRQ) | 68 |
| SAR 57 | cyclo(FfFRrRQ) | 69 |
| SAR 58 | cyclo(fFfrRrQ) | 70 |
| SAR 59 | cyclo(fFfRrRQ) | 71 |
| SAR 60 | cyclo(FfFrRrQ) | 72 |
| SAR 61 | cyclo(fFΦrRrQ) | 73 |
| SAR 62 | cyclo(fΦfrRrQ) | 74 |
| SAR 63 | cyclo(ΦFfrRrQ) | 75 |
| SAR 64 | cyclo(FΦrRrQ) | 76 |
| SAR 65 | cyclo(fΦrRrQ) | 77 |
| SAR 66 | Ac-(Lys-fFRrRrD) | 78 |
| SAR 67 | Ac-(Dap-fFRrRrD) | 79 |

TABLE 4-continued

Examples of Cyclic Cell-Penetrating Peptides (cCPPs)

| ID | cCPP Sequence | SEQ ID NO |
|---|---|---|
| SAR 68 | CWWRRRRC (S—S) | 80 |
| SAR 69 | CWWVRRRC (S—S) | 81 |
| SAR 70 | CFWRRRRC (S—S) | 82 |
| SAR 71 | CWWWRRRC (S—S) | 83 |
| Pin1 15 | cyclo(Pip-Nal-Arg-Glu-arg-arg-glu) | 84 |
| Pin1 16 | cyclo(Pip-Nal-Arg-Arg-arg-arg-glu) | 85 |
| Pin1 17 | cyclo(Pip-Nal-Nal-Arg-arg-arg-glu) | 86 |
| Pin1 18 | cyclo(Pip-Nal-Nal-Arg-arg-arg-Glu) | 87 |
| Pin1 19 | cyclo(Pip-Nal-Phe-Arg-arg-arg-glu) | 88 |
| Pin1 20 | cyclo(Pip-Nal-Phe-Arg-arg-arg- Glu) | 89 |
| Pin1 21 | cyclo(Pip-Nal-phe-Arg-arg-arg- glu) | 90 |
| Pin1 22 | cyclo(Pip-Nal-phe-Arg-arg-arg- Glu) | 91 |
| Pin1 23 | cyclo(Pip-Nal-nal-Arg-arg-arg- Glu) | 92 |
| Pin1 24 | cyclo(Pip-Nal-nal-Arg-arg-arg- glu) | 93 |
| Rev-13 | [Pim-RQRR-Nlys]GRRR[b] | 94 |
| hLF | KCFQWQRNMRKVRGPPVSC (disulfide) | 95 |
| cTat | [KrRrGrKkRrE][c] | 96 |
| cR10 | [KrRrRrRrRrRE][c] | 97 |
| L-50 | [RVRTRGKRRIRRpP] | 98 |
| L-51 | [RTRTRGKRRIRVpP] | 99 |
| [WR]4 | [WRWRWRWR] | 100 |
| MCoTI-II | [GGVCPKILKKCRRDSDCPGACICRGNGYCGSGSD] | 101 |
| Rotstein et al. Chem. Eur. J. 2011 | [P-Cha-r-Cha-r-Cha-r-Cha-r-G][d] | 102 |
| Lian et al. J. Am. Chem. Soc. 2014 | Tm(SvP-F$_2$Pmp-H)-Dap-(FΦRRRR-Dap)][f] | 103 |
| Lian et al. J. Am. Chem. Soc. 2014 | [Tm(a-Sar-D-pThr-Pip-ΦRAa)-Dap-(FΦRRRR-Dap)][f] | 104 |
| IA8b | [CRRSRRGCGRRSRRCG][g] | 105 |
| Dod-[R$_5$] | [K(Dod)RRRR] | 106 |

TABLE 4-continued

Examples of Cyclic Cell-Penetrating Peptides (cCPPs)

| ID | cCPP Sequence | SEQ ID NO |
|---|---|---|
| LK-3 | LKKLCKLLKKLCKLAG LKKLȻKLLKKLȻKLAG | 107 |
| | RRRR-[KRRRE]ᵉ | 108 |
| | RRR-[KRRRRE]ᵉ | 109 |
| | RR-[KRRRRRE]ᵉ | 110 |
| | R-[KRRRRRRE]ᵉ | 111 |
| [CR]₄ | [CRCRCRCR] | 112 |
| cyc3 | [Pra-LRKRLRKFRN-AzK]ʰ | 113 |
| PMB | T-Dap-[Dap-Dap-f-L-Dap-Dap-T] | 114 |
| GPMB | T-Agp-[Dap-Agp-f-L-Agp-Agp-T] | 115 |
| cCPP1 | cyclo(FΦRRRRQ) | 116 |
| cCPP12 | cyclo(FfΦRrRrQ) | 117 |
| cCPP9 | cyclo(fΦRrRrQ) | 118 |
| cCPP11 | cyclo(fΦRrRrRQ) | 119 |
| cCPP18 | cyclo(FϕrRrRq) | 120 |
| cCPP13 | cyclo(FϕrRrRQ) | 121 |
| cCPP6 | cyclo(FΦRRRRRQ) | 122 |
| cCPP3 | cyclo(RRFRΦRQ) | 123 |
| cCPP7 | cyclo(FFΦRRRRQ) | 124 |
| cCPP8 | cyclo(RFRFRΦRQ) | 125 |
| cCPP5 | cyclo(FΦRRRQ) | 126 |
| cCPP4 | cyclo(FRRRRΦQ) | 127 |
| cCPP10 | cyclo(rRFRΦRQ) | 128 |
| cCPP2 | cyclo(RRΦFRRQ) | 129 |

Φ, L-2-naphthylalanine; ϕ, D-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; F2Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinylpropionic acid; ᵇCyclization between Pim and Nlys; ᶜCyclization between Lys and Glu; ᵈMacrocyclization by multicomponent reaction with aziridine aldehyde and isocyanide; ᵉCyclization between the main-chain of Gln residue; ᶠN-terminal amine and side chains of two Dap residues bicyclized with Tm; ᵍThree Cys side chains bicyclized with tris (bromomethyl) benzene; ʰCyclization by the click reaction between Pra and Azk.

Additionally, the cCPP used in the polypeptide conjugates and methods described herein can include any sequence disclosed in: U.S. application Ser. No. 15/312,878; U.S. application Ser. No. 15/360,719; U.S. App. No. 62/438,141; and U.S. App. No. 62/507,483, each of which is incorporated by reference in its entirety for all purposes.

Group that Binds to the Cargo by Electrostatic Interactions (P)

The polypeptide conjugate of the present disclosure comprises
- a) a group that binds to a nucleic acid sequence ("cargo") by electrostatic interactions (P) comprising at least one peptide or polyamine; and
- b) at least one cell-penetrating peptide (CPP);
- wherein each peptide comprises at least three monomers selected from arginine, arginine-analog, lysine, lysine-analog, histidine, or histidine-analog; wherein the P is conjugated to the CPP through a bond or at least one linker (L); and
- wherein the polypeptide conjugate is optionally charged.

In one embodiment, the group that electrostatically interacts with the cargo (P) comprises a polyarginine peptide (pArg). In some embodiments, the polyarginine peptide comprises three arginine monomers or arginine-analog monomers. In some embodiments, the polyarginine peptide comprises four arginine monomers or arginine-analog monomers. In some embodiments, the polyarginine peptide comprises five arginine monomers or arginine-analog monomers. In some embodiments, the polyarginine peptide comprises 3 to 50 arginine monomers or arginine-analog monomers.

In some embodiments, P comprises polyarginine peptide comprising 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ariginine monomers or arginine-analog monomers.

In some embodiments, P comprises a polyarginine peptide having the following repeating units where n is an integer selected from 1 to 100 and the polyarginine peptide can have one additional arginine monomer to make an odd-numbered chain.

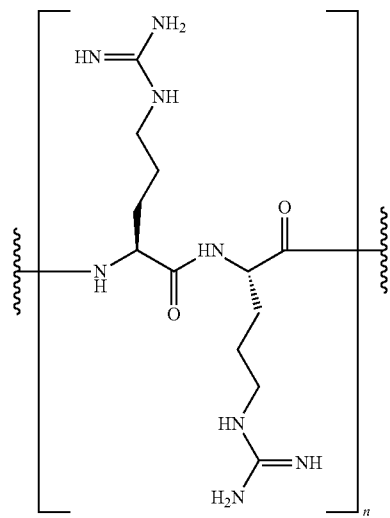

In some embodiments, P comprises a polyarginine peptide having the following repeating units where n is an integer selected from 1 to 50. In some embodiment, n is 1, 2, 3, 4, or 5.

prises three lysine monomers or lysine-analog monomers. In some embodiments, the polylysine peptide comprises four lysine monomers or lysine-analog monomers. In some embodiments, the polylysine peptide comprises five lysine monomers or lysine-analog monomers. In some embodiments, the polylysine peptide comprises 3 to 50 lysine monomers or lysine-analog monomers.

In some embodiments, P comprises polylysine peptide comprising 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 lysine monomers or lysine-analog monomers.

In one embodiment, the group that electrostatically interacts with the cargo (P) comprises a polyhistidine peptide (pHis). In some embodiments, the polyhistidine peptide comprises three histidine monomers or histidine-analog monomers. In some embodiments, the polyhistidine peptide comprises four histidine monomers or histidine-analog monomers. In some embodiments, the polyhistidine peptide comprises five histidine monomers or histidine-analog monomers. In some embodiments, the polyhistidine peptide comprises 3 to 50 histidine monomers or histidine-analog monomers.

In some embodiments, P comprises polyhistidine peptide comprising 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 histidine monomers or histidine-analog monomers.

In one embodiment, the group that electrostatically interacts with the cargo (P) comprises a peptide comprises monomers selected from arginine, arginine-analog, lysine, lysine-analog, histidine, histidine-analog, or mixtures thereof. In some embodiments, the peptide comprises three monomers selected from arginine, arginine-analog, lysine, lysine-analog, histidine, or histidine-analog. In some embodiments, the peptide comprises four monomers selected from arginine, arginine-analog, lysine, lysine-analog, histidine, or histidine-analog. In some embodiments, the peptide comprises five monomers selected from arginine, arginine-analog, lysine, lysine-analog, histidine, or histidine-analog. In some embodiments, the peptide comprises 3 to 50 monomers selected from arginine, arginine-analog, lysine, lysine-analog, histidine, or histidine-analog.

In one embodiment, the group that electrostatically interacts with the cargo (P) comprises a polylysine peptide (pLys). In some embodiments, the polylysine peptide com-

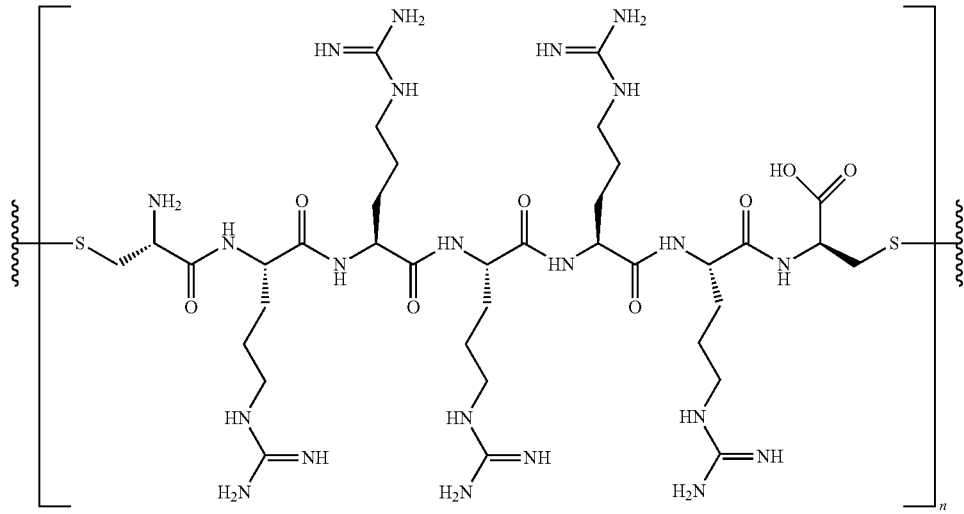

In some embodiments, P comprises a peptide comprising 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 monomers selected from arginine, arginine-analog, lysine, lysine-analog, histidine, or histidine-analog. In some embodiments, arginine, arginine-analog, lysine, lysine-analog, histidine, or histidine-analog monomers can be in any order, D or L, or permutation thereof. In some embodiment, the monomers alternate D and L in the peptide sequence.

In some embodiments, P comprises a polyamine selected from a spermidine polymer or a spermine polymer. In some embodiments, P comprises a polyamine structure:

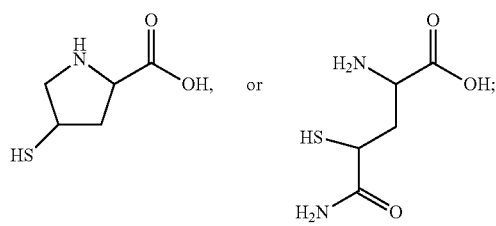

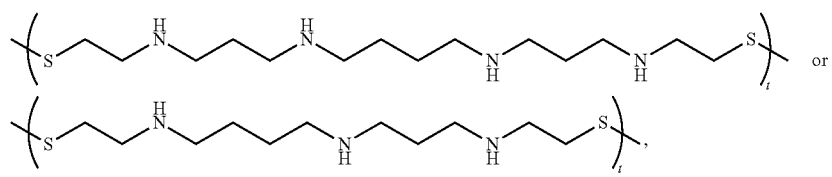

wherein t is an integer selected from 1-50, or a charged species thereof.

In some embodiments, P further comprises at least one cysteine monomer or a cysteine-analog monomer. In some embodiments, P further comprises at least two cysteine monomers or cysteine-analog monomers.

In some embodiments, P further comprises at least one group selected from:

wherein the bond to the hydrogen on one at least one of the N- or C-termini is replaced by a bond to the peptide or polyamine; and wherein the bond to the hydrogen on the thiol group is replaced by a bond to the CPP.

In some embodiments, P further comprises at least one group selected from:

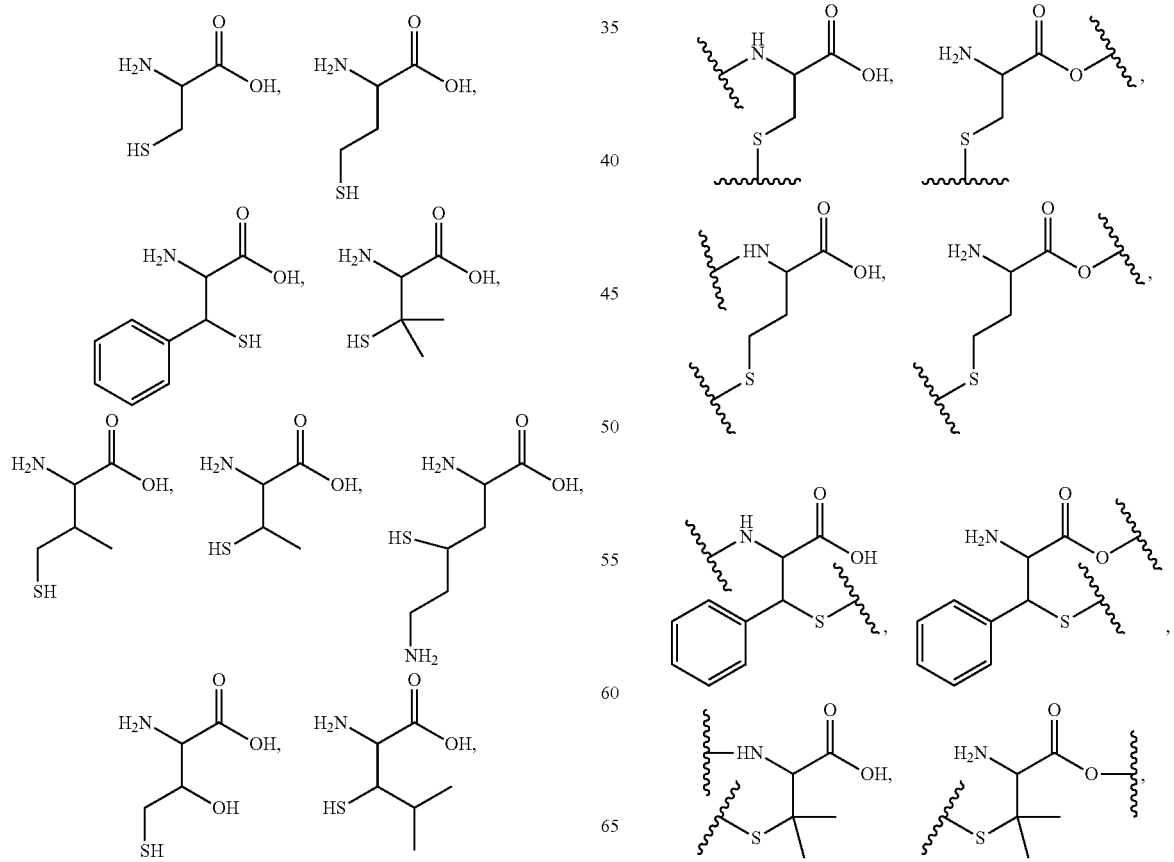

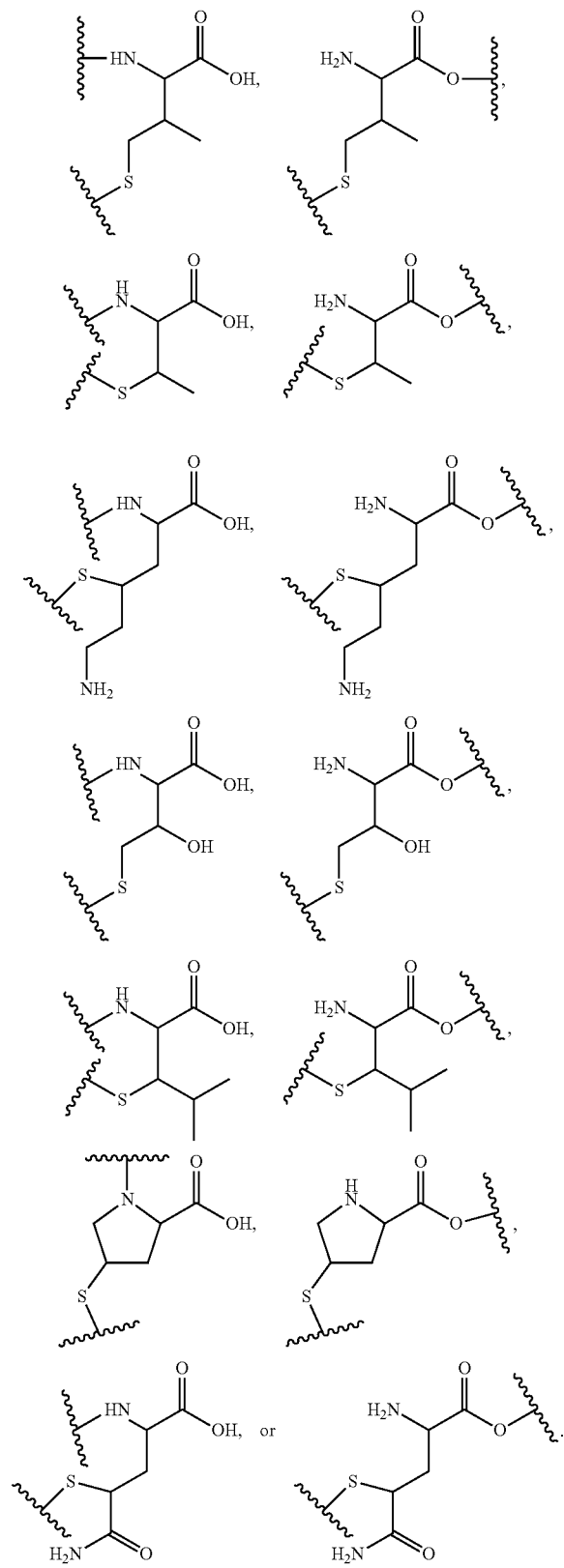

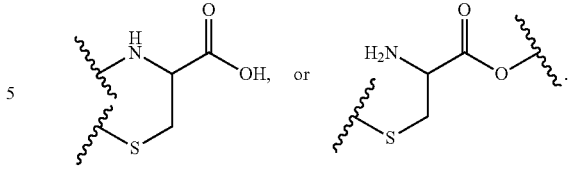

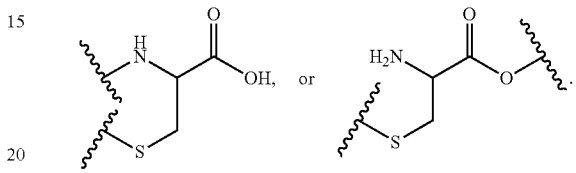

In some embodiments, at least one of the P (including P¹ and P²) in the polypeptide conjugate as disclosed herein further comprises In other embodiments, at least one of the P in the polypeptide conjugate as disclosed herein further comprises at least two groups selected form In some embodiments, P (including P¹ and P²) further comprises one or more 3-alanine monomers. In one embodiment, P (including P¹ and P²) further comprises at least one amino acid monomer (e.g., such as those shown in Table 4). In one embodiment, P (including P¹ and P²) further comprises a thioether moiety (—S—). In some embodiments, P is pArg further comprising one or more β-alanine monomers.

In some embodiments, P (including P¹ and P²) comprises -Cys-(Arg)$_x$-Cys-(SEQ ID NO: 131), -Cys-βAla-(Arg)$_x$-Cys- (SEQ ID NO: 132), -Cys-(Arg)$_x$-βAla-Cys-(SEQ ID NO: 133), -Cys-βAla-(Arg)$_x$-βAla-Cys- (SEQ ID NO: 134), -Cys-(polyamine)$_x$-Cys-, -Cys-βAla-(polyamine)$_x$-Cys-, -Cys-(polyamine)$_x$-βAla-Cys-, -Cys-βAla-(polyamine)$_x$-βAla-Cys- (SEQ ID NO: 135), —S-(polyamine)$_x$-S—, wherein x=3, 4, 5, 6, 7, or 8.

In some embodiments, "—" between different groups of P (including [P]$_n$, [P]$_m$ and [P]$_o$) represents a bond between two sulfur atoms (a disulfide bond).

In some embodiments, P, P¹, or P², at each occurrence, are same or different.

In some embodiments, P is charged. In some embodiments, P is positively charged. In some embodiments, P is positively charged and interact with negatively charged nucleic acids by non-covalent interactions. In some embodiments, P is positively charged and interact with negatively charged nucleic acids by electrostatic interactions.

In some embodiments, P binds (by electrostatic interactions) to a cargo to form 1:1 (mol:mol) complex. Without being bound to any theory, the complex formed between P and the cargo (e.g., nucleic acid) can protect the cargo and P from enzymatic degradation during storage or in vivo circulation.

In some embodiments, P is biodegradable. In some embodiments, P can undergo reductive cleavage inside the cytosol. In some embodiments, the reductive cleavage is by cleavage of the disulfide bonds. In some embodiment, the degradation is by proteolytic degradation. In some embodiments, P can release the cargo inside the cytosol.

Linkers (L)

In some embodiments, the polypeptide conjugate comprises a linker (L) that connects the CPP to the P. In some embodiment of the polypeptide conjugate as disclosed herein, at least one L comprises a divalent optionally substituted group selected from amino acid, alkylene, alkenylene, alkynylene, aryl, cycloalkyl, cycloalkenyl, cycloalkynyl, heterocyclyl, heteroaryl, —($R^1$—X—$R^2$)z-, or combinations thereof; wherein each of $R^1$ and $R^2$ are independently selected from a bond, alkylene, alkenylene, alkynylene, carbocyclyl, and heterocyclyl, wherein $R^1$ and $R^2$ are not both a bond;

each X is independently N, S, and O; and z is an integer selected from 1 to 20.

In some embodiments of the polypeptide conjugate as disclosed herein, at least one L comprises a divalent polyethylene glycol moiety. In some embodiments, at least one L comprises an optionally substituted —(O—$CH_2CH_2$)z- or an optionally substituted —($CH_2CH_2$—O)z-. In some embodiments, at least one L comprises a divalent 8-amino-3,6-dioxaoctanoic acid residue. In other embodiments, at least one L comprises a divalent 8-amino-3,6,9-trioxaundecanoic acid residue.

In some embodiments, L comprises one or more groups selected from:

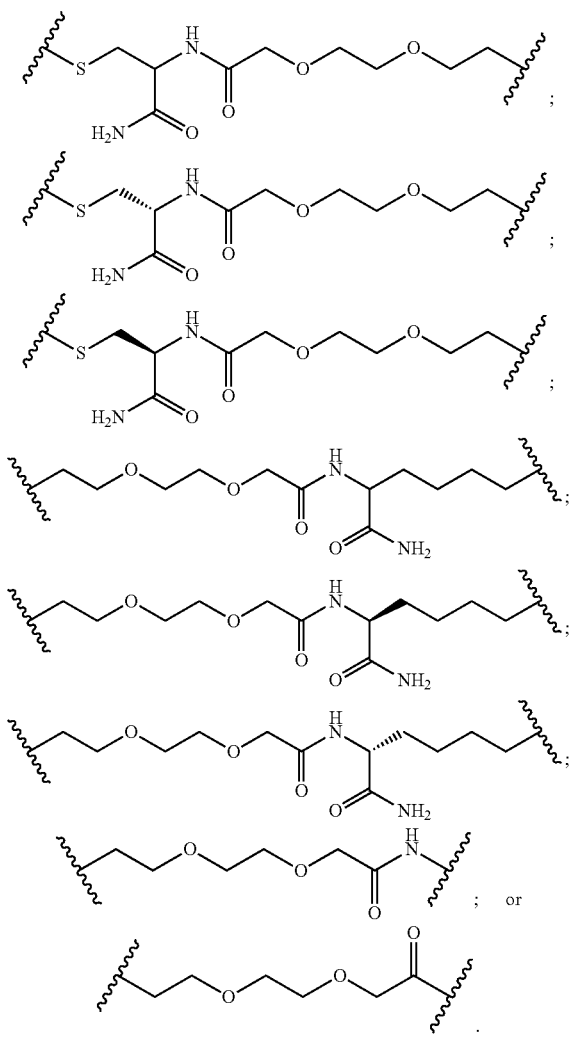

In some embodiments, at least one L comprises a physiological cleavable group (PCG). In some embodiments, each PCG is, independently, selected from —S—S—, carbonate (—O—C(O)O—), thiocarbonate (—O—C(S)O—), thioester (—C(S)O—), sulfoxide (—S(O)—), hydrazine (—$H_2$N—$NH_2$—), or protease-cleavable dipeptide linker. In other embodiments, each PCG comprises at least one —S—S—.

In some embodiments, L comprises two or more PCGs. Non-limiting examples of such L include dendrimers (e.g., cyclotriphosphazene, polypropylenimine, polylysine, and polyamidoamine dendrimers having appropriate terminal groups to form a PCG), dendrons (e.g., 2-bis(hydroxymethyl)propanyl-based dendrons having appropriate terminal groups to form a PCG), and hyperbranched polymers (e.g., hyperbranched bis-MPA polyester ving appropriate terminal groups to form a PCG).

In some embodiments of any one of the polypeptide conjugate as disclosed herein, at least one of the "—" between L (including $L^1$ and $L^2$) and P (including $[P]_n$, $[P^1]_p$, $[P^2]_q$ and $([P]_m)_s$) represents a bond between two sulfur atoms (disulfide bond). In other embodiments, the "—" between L and P each represents a bond between two sulfur atoms (disulfide bond).

In some embodiments, L, $L^1$, or $L^2$, at each occurrence, are same or different.

Complex

The present disclosure also relates to a complex comprising any one of the polypeptide conjugate as disclosed herein and a nucleic acid sequence (also referred to as cargo).

In some embodiments, the cargo is charged. In some embodiments, the cargo is negatively charged. In some embodiments, the negatively charged cargo interacts with positively charged P by non-covalent interactions. In some embodiments, the negatively charged cargo interacts with positively charged P by electrostatic interactions.

In some embodiments, the cargo is a nucleic acid. In some embodiments, the cargo is a nucleic acid sequence. In some embodiment, the nucleic acid or the nucleic acid sequence is therapeutically active or therapeutically effective.

In some embodiments, the cargo comprises therapeutically active agent for a gene therapy. In some embodiments, the cargo comprises splice-switching oligonucleotides, microRNAs, anti-microRNAs, antisense oligonucleotides, small interfering DNAs, plasmid DNAs, small interfering RNAs and/or mRNAs.

In some embodiments, the cargo comprises therapeutically active agent for a gene-editing.

In some embodiments, the cargo can enhance target gene expression or modulate/or switch mRNA splicing to express desired gene products.

The present disclosure also relates to a cell comprising any one of the polypeptide conjugate as disclosed herein. The present disclosure also relates to a cell comprising a complex comprising any one of the polypeptide conjugate as disclosed herein and a nucleic acid sequence.

Polypeptide Conjugate as a Delivery Device

The present disclosure also relates to a method of delivering the cargo (e.g., a nucleic acid sequence) to a cell, comprising contacting the cell with any one of the polypeptide conjugate complex as disclosed herein.

The present disclosure also relates to a method of delivering the cargo to a cell of a subject in need thereof, comprising administering any one of the polypeptide conjugate complex as disclosed herein.

The present disclosure also relates to a method of treating a disease or condition in a patient in need thereof, comprising administering any one of the polypeptide conjugate complex as disclosed herein to the patient. The disease or condition may be any disease or condition that can be treated by gene replacement or gene therapy. In some embodiment, the disease or condition is cancer, genetic diseases, autoimmunity, inflammatory diseases, neurodegenerative diseases, or infectious diseases.

EXAMPLES

Example 1. Polypeptide Conjugate with Two Terminal cCPPs

Design and Synthesis. A non-covalent complex between cyclic CPP-based delivery vector and a nucleic acid (NA) cargo of interest instead of covalent attachment was selected for a number of reasons. First, in a covalent CPP-nucleic acid conjugate, the negatively charged nucleic acid may interact with the positively charged CPP (either intramolecularly or intermolecularly) and mutually interfere with each other's function. Second, in a covalent adduct, the nucleic acid cargo is unprotected from nuclease action and may have limited in vivo stability. Third, production of a covalent conjugate is more complex, requiring chemical synthesis of each component followed by biorthogonal conjugation, whereas a non-covalent complex can be formed by simply mixing the two components. However, it was also desired to avoid the formation of nanoparticles, which are largely limited to biodistribution into the liver and kidney (see Juliano, R. L. *Nucleic Acids Res.*, 2016, 44(14): 6518-6548; Shi, B. et al., *J Histochem Cytochem.*, 2011, 59(8): 727-740). With these considerations in mind, a novel NA delivery system was designed consisting of a biodegradable polyarginine sequence flanked by two cyclic CPPs, which are copolymerized through the formation of a series of disulfide bonds (FIG. 1). The polyarginine moiety was expected to bind tightly to a NA cargo (e.g., siRNA) through electrostatic interactions to form a 1:1 (mol/mol) complex, while the two terminal CPPs would be exposed for binding to the cell membrane and ensuring cellular entry of the complex. Non-covalent complexation could allow the same vector to deliver different siRNA sequences (and potentially other NAs).

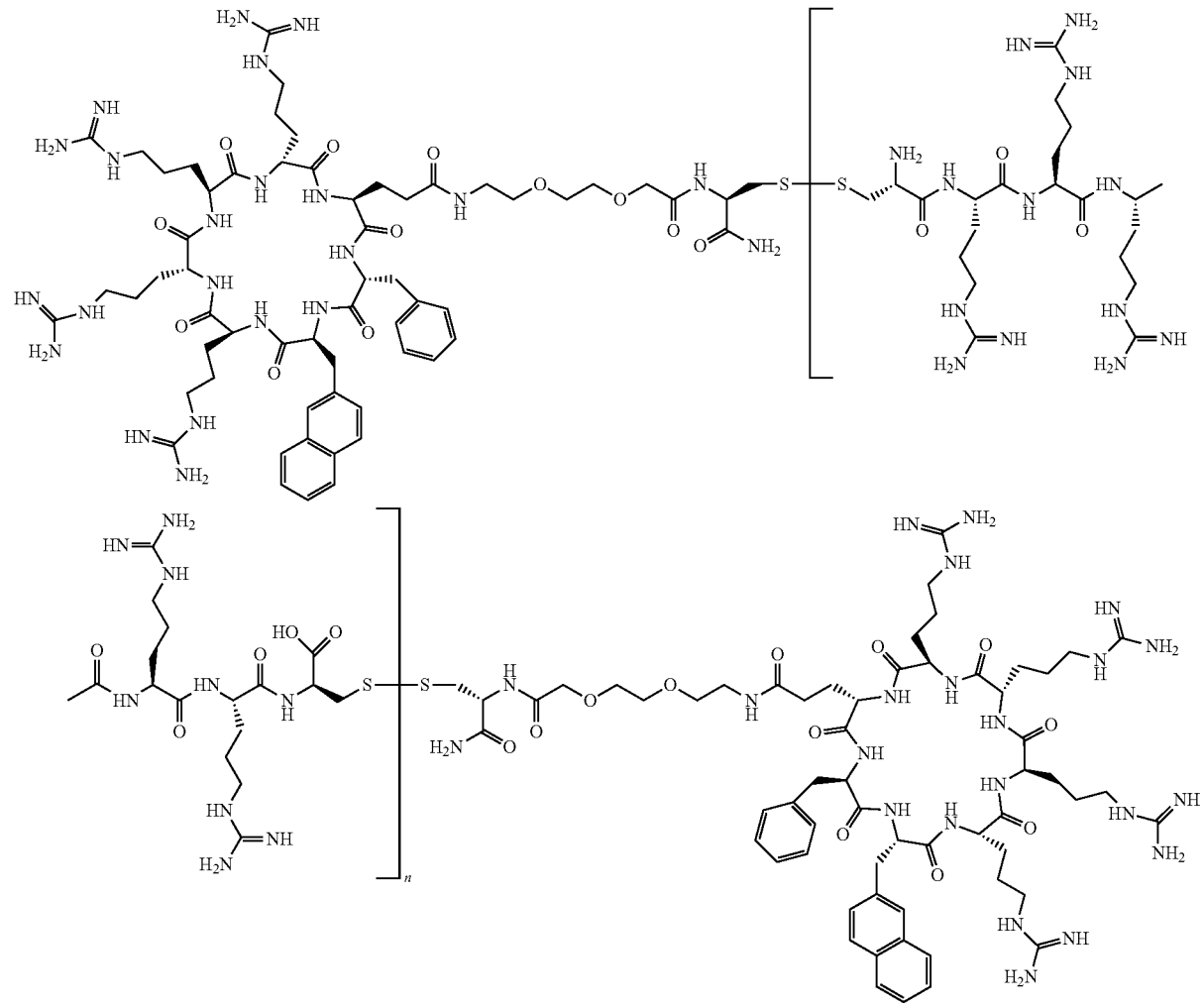

CPP9 (see Table 4), which has a cytosolic delivery efficiency of 62%, was selected for this study. To minimize any mutual interference between the CPP and the cargo, a long, flexible linker (miniPEG) was attached to the Gln side chain and a cysteine was added to the other end of the linker. The polyarginine sequence was formed by polymerization of Cys-Arg-Arg-Arg-Arg-Arg-Cys (SEQ ID NO: 136) ($CR_5C$) through the formation of disulfide bonds. A pentaarginine was selected because longer polyarginines (e.g., $R_{10}$), without bound to any theory, would bind more tightly to NAs and may not effectively release the cargo inside the cell.

Peptides CR$_5$C (SEQ ID NO: 136) and cyclo(fΦRrRrQ)-miniPEG-Cys (SEQ ID NO: 141) were synthesized manually on Rink amide resin (0.54 mmol/g) using standard Fmoc chemistry. The typical coupling reaction contained 5 eq of Fmoc-amino acid, 5 eq HATU and 10 eq DIPEA in DMF with mixing for 1 h. The N-terminal Fmoc group was removed by 20% piperidine in DMF. For cyclo(fΦRrRrQ) peptide (SEQ ID NO: 118), after the entire sequence was completed but prior to Fmoc deprotection, the allyl group on the C-terminal Glu was removed by treatment with 0.1 eq Pd(PPh$_3$)$_4$ and 10 eq phenylsilane in DCM (3×15 min). The N-terminal Fmoc was then removed and the peptide was cyclized by treatment with 5 eq PyBOP, 5 eq HOBt and 10 eq DIPEA in DMF for 3 h. The peptides were cleaved from the resin and side chain deprotected by treatment with 90/2.5/2.5/2.5/2.5 (v/v) TFA/TIPS/DMB/DCM/EDT/water for 3 h. The peptides were triturated with cold ethyl ether and purified by reversed-phase HPLC. The purity of peptides (>95%) was confirmed with an analytical reversed-phase HPLC and the identity of peptides was confirmed by MALDI-TOF mass spectrometry.

Three different polymerization reactions were carried out by mixing 5, 10 or 20 equivalents of CRSC and 1 equivalent of CPP9-miniPEG-Cys in PBS (pH 7.4) containing 30% DMSO and stirring the mixture for 24 h. The reaction products were dialyzed against a semipermeable membrane (MWCO: 10 kDa) to remove DMSO and low-MW species. The resulting polymers were lyophilized. The expected MWs of the polymers are listed in Table 5.

TABLE 5

Theoretical molecular weight (MW) of CRC polymers

| Polymer | Mole ratio of CR5C per CPP9 | Theoretical MW (kDa) |
|---|---|---|
| CRC5 | 5 | 12.7 |
| CRC10 | 10 | 26.9 |
| CRC15 | 20 | 42.8 |

Figure 2:
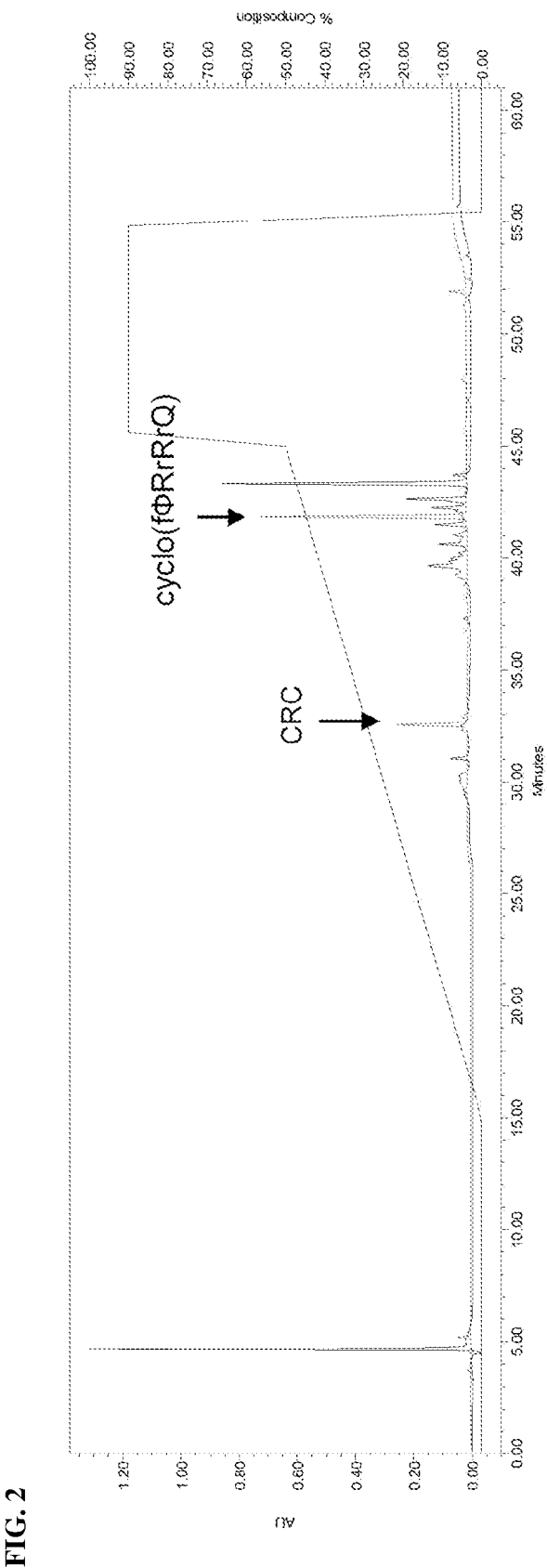
FIG. 2 shows an analytical HPLC (high-performance liquid chromatography) trace of polypeptide conjugate synthesized in Example 1 The arrows to CRC and cyclo (fΦRrRrQ) (SEQ ID NO: 118) points to HPLC trace of conjugate after reduction with 10 mM DTT (dithiothreitol).

Polymer Characterization by Analytical HPLC. Analytical HPLC of the CRC5 polymer (from 5:1 CR$_5$C and CPP9) revealed a mixture of many species, with the most abundant species having a retention time of 43.3 min (FIG. 2). Treatment of the CRC5 polymer with 10 mM DTT converted the polymer into a mixture of predominantly two species, with retention times corresponding to those of CR$_5$C and CPP9-miniPEG-Cys, suggesting that the CRC5 polymer was indeed formed, but contained a mixture of polymers of different numbers of CR$_5$C units.

Figure 3:
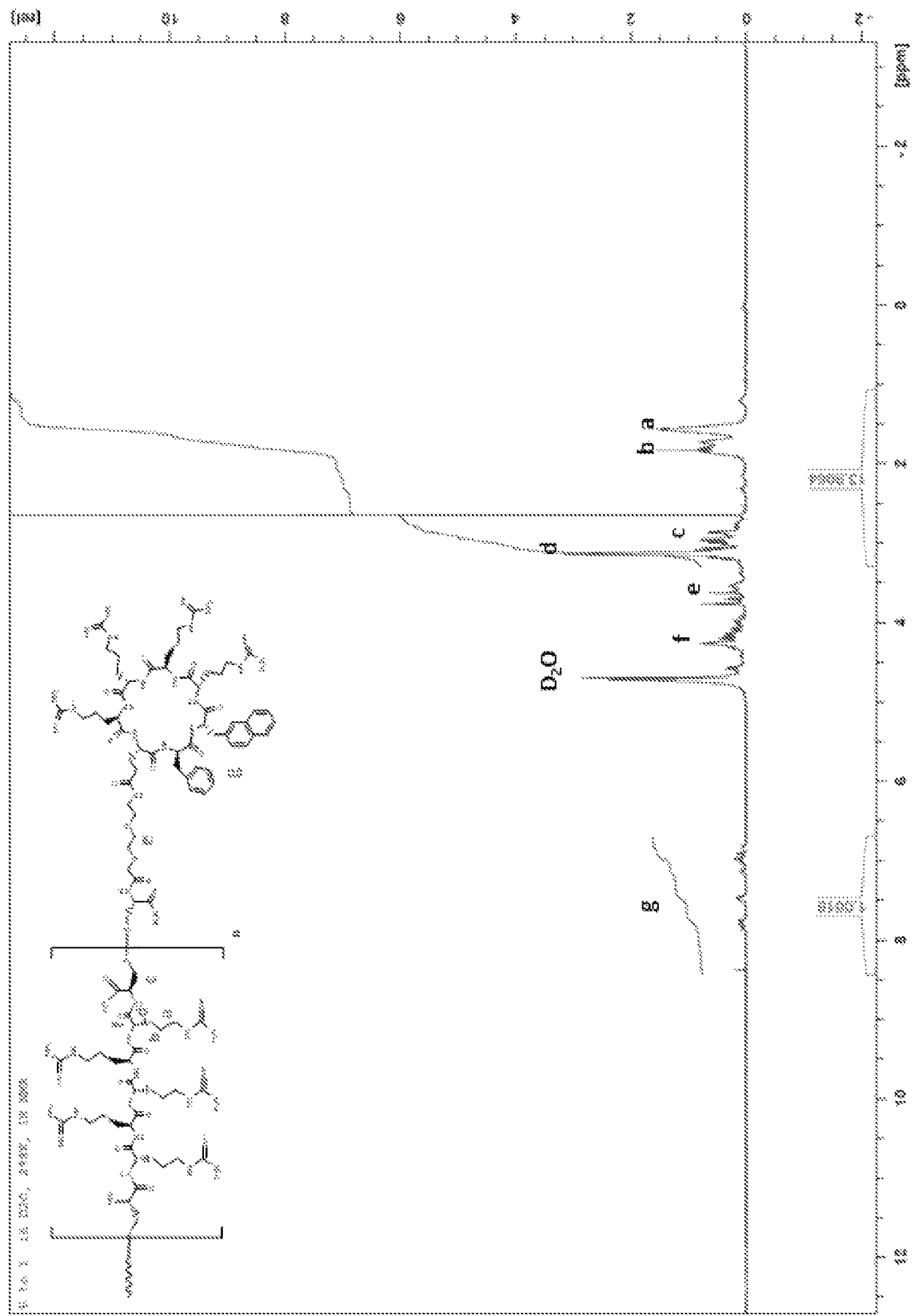
FIG. 3 shows $^1$H NMR (nuclear magnetic resonance) spectrum of the polypeptide conjugate synthesized in Example 1.

Estimation of MW by 1H-NMR. The 1H-NMR spectra of CRC5 and CRC10 polymers (5 mM concentration in 100% D$_2$O) were recorded at 600 MHz (Bruker, MA, USA). FIG. 3 shows the $^1$H-NMR spectrum of CRC5. Resonances at δ1.4-1.6 (signal a), δ1.6-1.9 (signal b) and δ3.1-3.3 (signal d) were assigned to the —CH$_2$— groups in the arginine side chain. The signals at δ2.8-3.1 (signal c) were assigned to the —CH$_2$— group of cysteine. The signals at δ3.6-3.9 (signal e) were derived from the miniPEG linker. The signals at δ4.0-4.4 (signal f) were from the C$_\alpha$-H's of amino acids. Signals at δ6.7-8.4 (g) are assigned to the aromatic protons from phenylalanine and naphthylalanine. The average number of repeating units (CR$_5$C) in the polymers (n) and the MW of the polymers were estimated by comparing the integrated signal intensities of the arginine side chains (signals a, b, c, d) and the aromatic protons (signal g). For the CRC5 polymer, n was found to be 8, corresponding to a MW of 10.6 kDa. For the CRC10 polymer, n was found to be 20 and the average MW was 22.6 kDa. These values are similar to the theoretical values (Table 5).

Figure 4A:
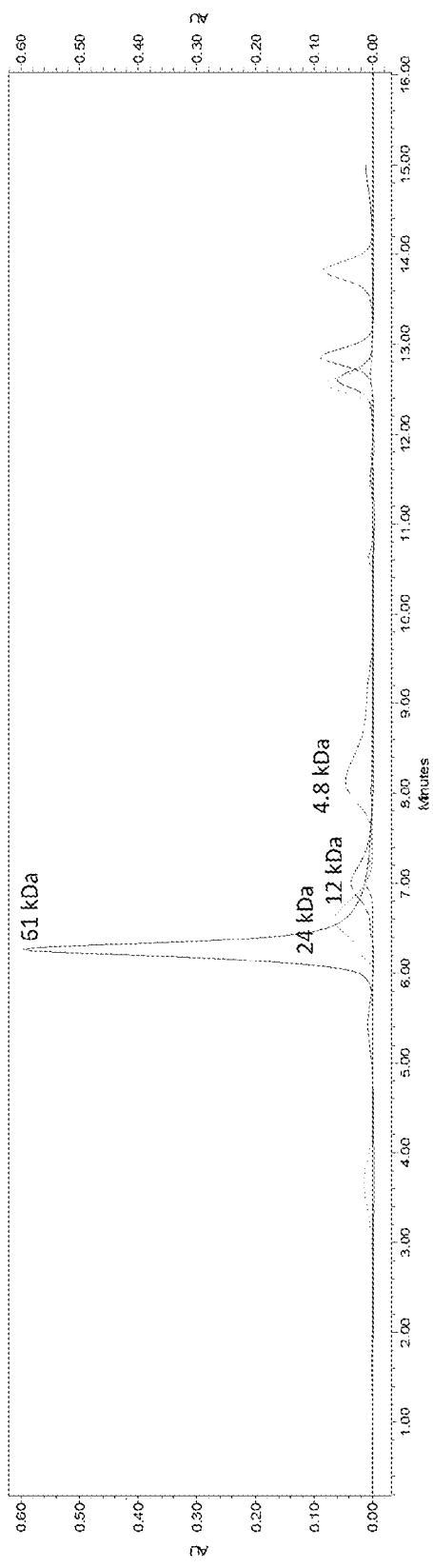
FIG. 4A shows gel-filtration chromatography traces of poly-L-lysine standard.
Figure 4B:
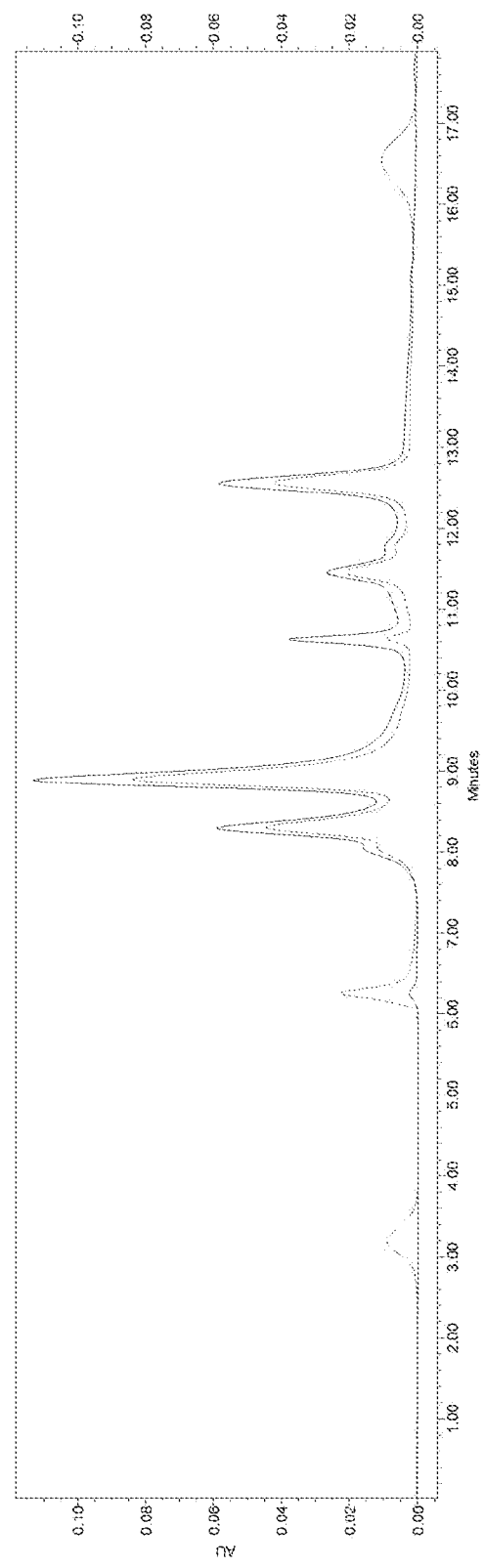
FIG. 4B shows gel-filtration chromatography traces of the polypeptide conjugate synthesized in Example 1 (CRC5— top line at t=9 min: CRC10 bottom line at t=9 min).

Estimation of MW by Gel-Filtration Chromatography (GPC). The MW distribution of the polymers (in 0.1 M NaCl) was assessed by GPC on a Waters 600 HPLC system (Waters, MA, USA) equipped with a TSKgel G3000PWxl-CP column (Tosoh Biosciences, CA, USA) and UV detection at 214 nm. Poly-L-lysine (PLL) of varying MWs (4.8, 12, 24 and 61 kDa) were used as MW standards (FIG. 4A). Comparison of the GPC chromatogram of CRC5 to PLL suggested that 1-2% of the reaction mixture corresponded to a species with MW ~60 kDa (peak at ~6.2 min). The predominant species, however, had retention times of 8.3 and 9.0 min, corresponding to MW of 4-5 kDa and 2-4 kDa, respectively (FIG. 4B, top line at t=9 min). A similar MW distribution was observed for the CRC10 polymer. However, the ~60 kDa species (peak at ~6.2 min) was present at a higher percentage (~15% of the total) than in CRC5 (FIG. 4B, bottom line at t=9 min). A species with very high MW (retention time=3.2 min) was also observed. It should be noted that neither the NMR method described above nor the GPC analysis can provide an accurate measurement of the MWs. More accurate MW determination will require prior separation of the polymer mixture into individual species and NMR analysis of the individual species.

Figure 5A:
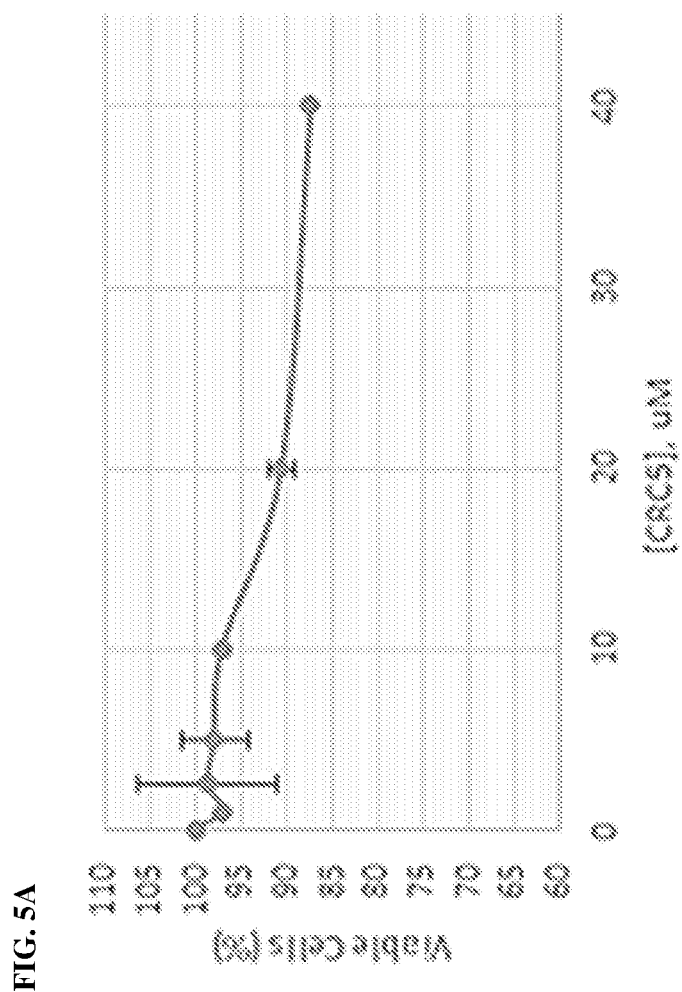
FIG. 5A shows the effect of CRC5 polymer synthesized in Example 1 on HeLa cells as assayed by the MTT (3-(4,5-dimethylthiazol-2-yl)-2,5-diphenyltetrazolium bromide) test.
Figure 5B:
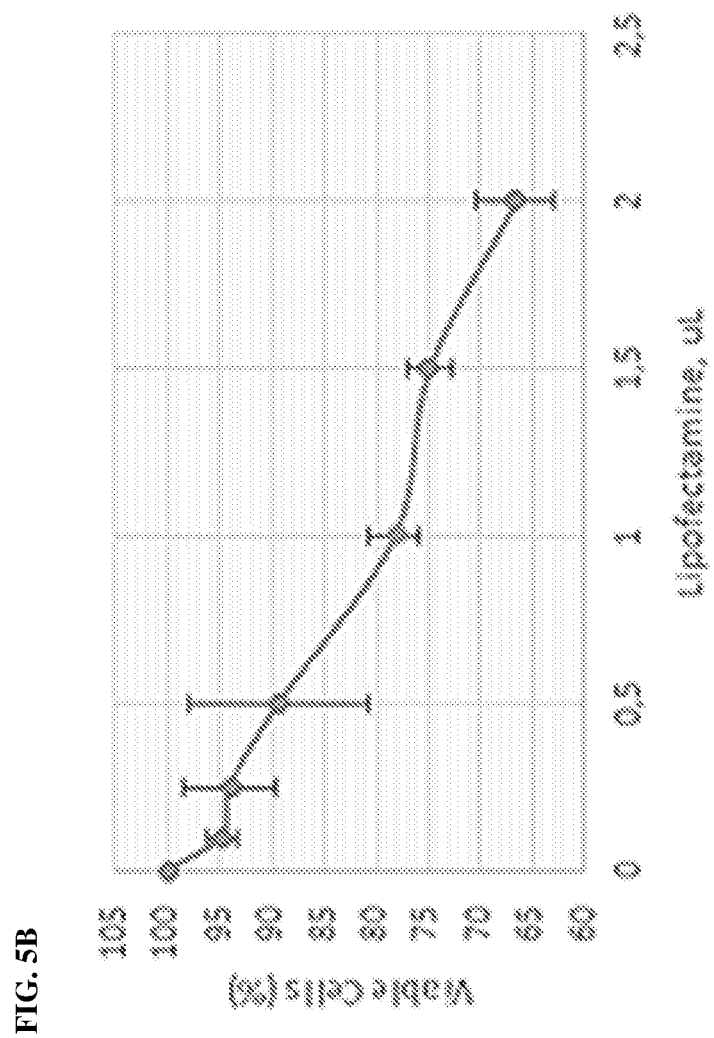
FIG. 5 shows the effect of lipofectamine on HeLa cells as assayed by the MTT

Cytotoxicity. The cytotoxicity of CRC5 polymer on HeLa cells was evaluated using the MTT assay. HeLa cells (3×10$^l$ cells per well) in 100 μL of DMEM containing 10% FBS were seeded in 96-well plate and incubated for 24 h. Then cells were treated with varying concentrations (0-40 M) of CRC5 and incubated at 37° C. with 5% CO$_2$ for 72 h. An MTT stock solution (10 μL; 5 mg/mL) was added into each well. The plate was incubated at 37° C. for 4 h. Then 100 μL of SDS-HC solubilizing buffer was added into each well, and the resulting solution was mixed thoroughly. The plate was incubated at 37° C. overnight. The absorbance of the formazan product was measured at 570 nm on a Tecan M1000 plate reader. CRC5 was relatively non-toxic to HeLa cells, causing ≤15% reduction in viability over the concentration range of 0 to 40 M (or 0-500 g/mL; FIG. 5A). In contrast, addition of 2 μL of the commercial lipofectamine solution (which is the recommended amount for transfection experiments) reduced the viability of HeLa cells by 35% (FIG. 5B).

siRNA Binding. The ability of CRC5 and CRC10 to bind siRNA targeting the firefly luciferase gene (siLuc) was tested by the gel retardation method using various N/P ratios, which correspond to the ratio between positively charged amino groups in the polymer (N stands for nitrogen in amino group) to negatively charged phosphate groups in the nucleic acid (P stands for phosphorous in phosphate group). The CRC polymer/siRNA complexes were formed with a fixed concentration of siRNA and increasing concentrations of CRC polymer to N/P ratios of 1:1 to 50:1. Free siRNA was used as a control. The samples were separated by electrophoresis on 1% agarose gel containing ethidium bromide at 70 V for 30 min in Tris-acetate-EDTA (TAE) buffer. While free siLuc RNA gave a discrete band on the gel, addition of the CRC polymers progressively decreased the intensity of the free RNA band and resulted in the formation of apparently an RNA/polymer complex that failed to migrate out of the sample loading well. Complete conversion of free siRNA into the RNA/polymer complex was observed at an N/P ratio of 10 for CRC5, while the corresponding ratio was 5 for CRC10. As expected, treatment of a preformed siLuc/CRC5 complex with 10 mM DTT resulted in a discrete band with the same mobility as the free RNA.

Figure 6:
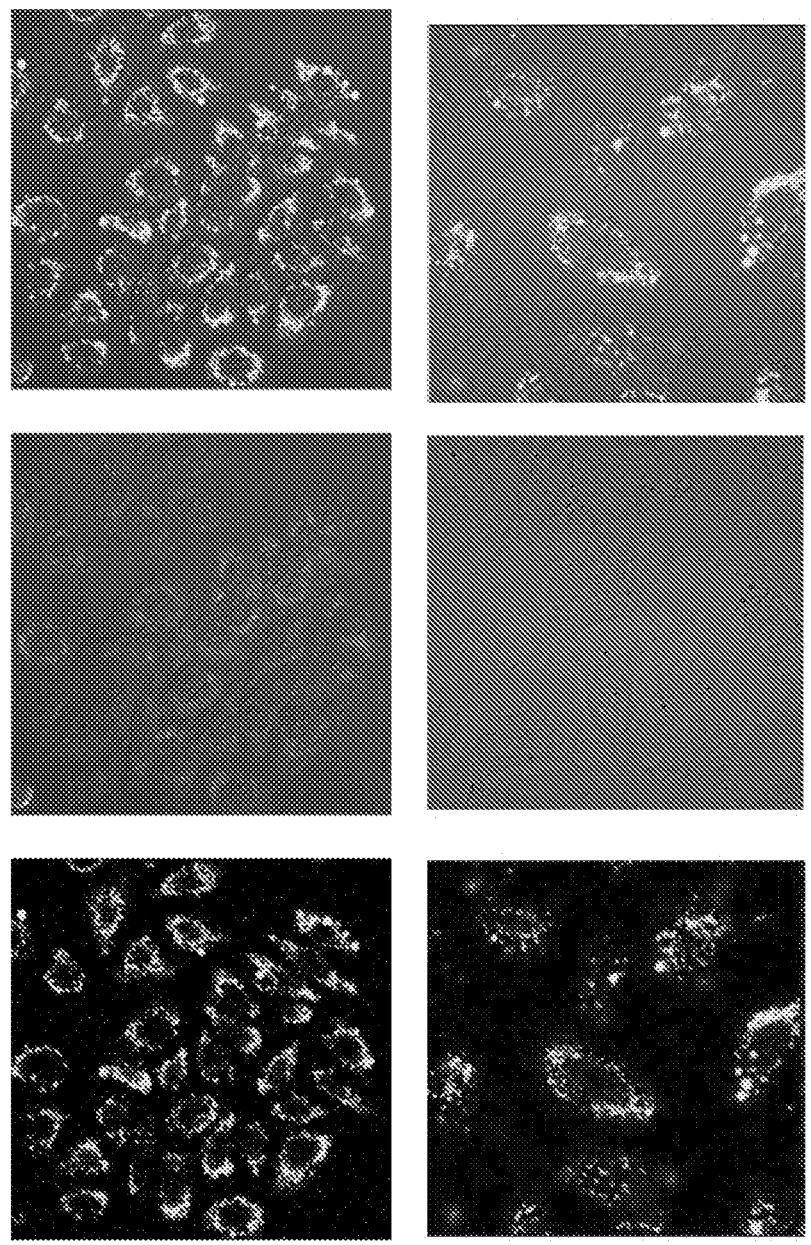
FIG. 6 shows live-cell confocal microscope images of HeLa cells treated with the CRC5/5'-FAM-siLuc complex (Example 1) at 3 M siRNA in OptiMEM (top) or at 1 μM siRNA in DMEM with 1% FBS, 1% Abs (bottom). Left, GFP channel; Center, DIC; and right, overlap of the above.

Cellular Uptake. To monitor the intracellular uptake of the CRC5/siLuc complex, 5'-fluorescein (FAM)-labelled siLuc (1 or 3 μM) was mixed with CRC5 to give an N/P ratio of 10 in OptiMEM or DMEM with 1% FBS and 1% Abs. HeLa cells were seeded in a 35 mm glass-bottomed microwell dish at a density of $3 \times 10^4$ cells/mL and cultured overnight. Cells were washed twice with DPBS and treated with the CRC5/5'-FAM-siRNA complex for 2 h. After removal of the medium, the cells were gently washed with DPBS twice and imaged on a Nikon A1R live-cell confocal microscope equipped with a 100× oil objective or a Visitech Infinity 3 Hawk 2D-array live cell confocal microscope equipped with 60× oil objective. Data were analyzed using NISElemenets AR or MetaMorph Premier. A mix of diffuse and punctate fluorescence was observed inside the cytoplasm of all treated cells, indicating that the CRC5/siLuc complex was able to enter the cells and at least partially escaped from the endosomes into the cytosol (FIG. 6). In FIG. 6, live-cell confocal microscopic images of HeLa cells treated with the CRC5/5'-FAM-siLuc complex at 3 μM siRNA in OptiMEM (top) or at 1 μM siRNA in DMEM with 1% FBS, 1% Abs (bottom). Left, GFP channel; Center, DIC; and right, overlap of the above.

Knockdown of Luciferase Expression. The ability of CRC polymers to deliver siRNA intracellularly was tested on a HeLa cell line stably transfected with a firefly luciferase gene (HeLa-Luc). The siLuc sequences used were: sense 5'-CUUACGCUGAGUACUUCGAdTdT-3' (SEQ ID NO: 137) and antisense 5'-UCGAAGUA-CUCAGCGUAAGdTdT-3' (SEQ ID NO: 138). Hela-Luc cells were seeded onto 96-well plate at a density of $1.5 \times 10^4$ cells/well in 100 μL of DMEM containing 10% FBS and cultured overnight. CRC5/siLuc complexes were formed by mixing CRC5 with siLuc in 20 mM HEPES, pH 7.4 followed by 15 min incubation. Complexes were then mixed with OptiMEM, added to cells and incubated at 37° C. for 24 or 48 h. Free siLuc, CRC5, Lipofectamine2000/siLuc, and pCRC/siLuc were used as controls. pCRC is a polymer of CRSC without CPP9 at the two termini. Lipofectamine2000 was complexed with siRNA according to the manufacturer's protocol. A luciferase assay kit (OZ Biosciences) was used to quantitate the luciferase gene silencing level according to manufacturer's protocol. Luminescence was measured on a Tecan Infinite M1000 plate reader.

Figure 7:
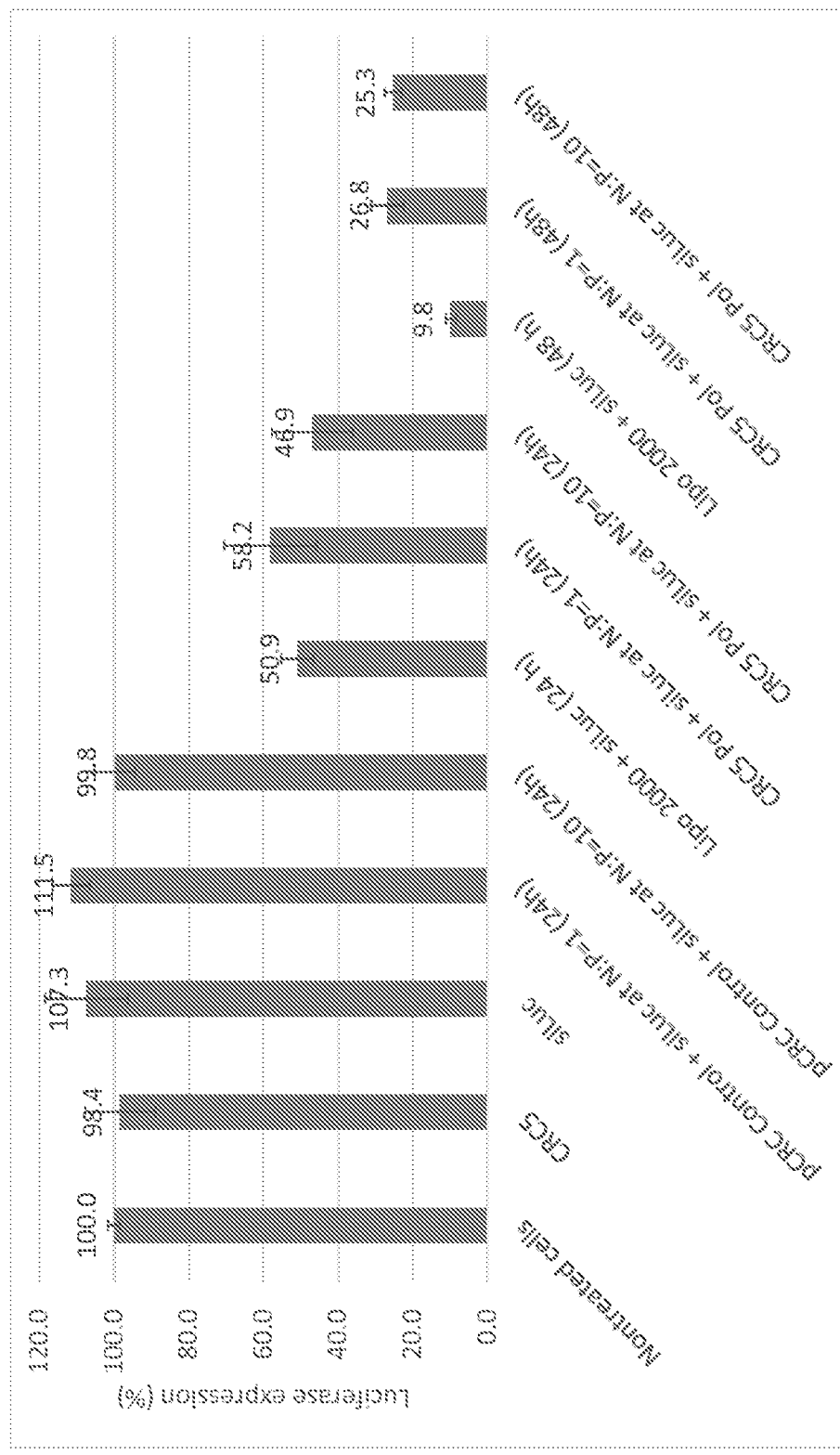
FIG. 7 shows knockdown of luciferase expression in HeLa-Luc cells by CRC5/siLuc complexes (Example 1, 75 nM), the individual components, and lipofectamine/siLuc complex at 24 h and 48 h after treatment.
Figure 9:
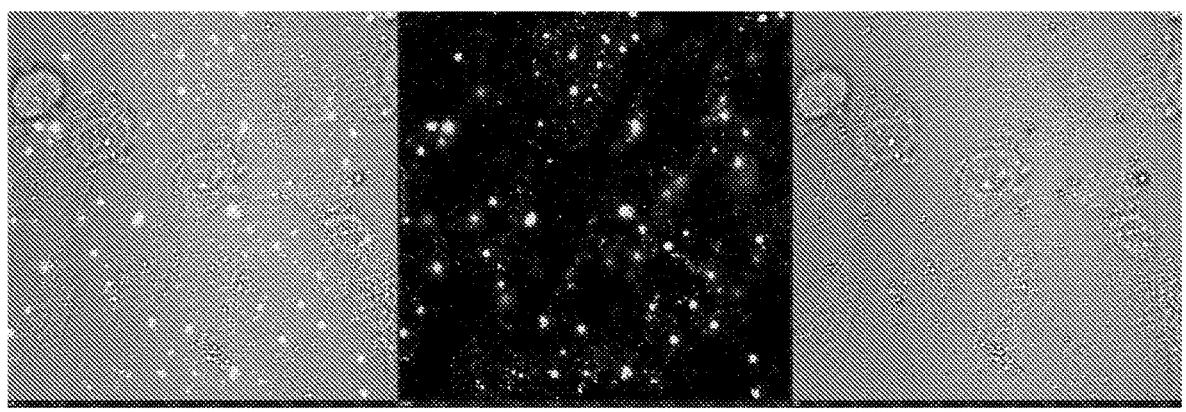
FIG. 9 shows live-cell confocal microscope images of HeLa cells treated with the CPP9-$(R_5)_2$/5'-FAM-siLuc complex (Example 2) at 3 M siRNA. Center, GFP channel; Right, DIC; and left, overlap of the above.

Treatment of HeLa-Luc cells with free siLuc, CRC5 alone, or the pCRC/siLuc complex did not reduce the luciferase expression (FIG. 9). On the other hand, the CRC5/siLuc complex substantially decreased the luciferase activity (50-75%) at all N/P ratios tested, with the highest silencing efficiency (75%) observed at an N/P ratio of 10 ([siLuc]=75 nM or 1 g/mL and 6.6 g/mL CRC5) and after 48 h of incubation. In fact, the gene silencing efficiency of the CRC5/siLuc complex was comparable to that of Lipofectamine2000/siLuc. However, as described above, CRC5 has much lower cytotoxicity than Lipofectamine. At their effective concentrations for siRNA delivery, lipofectamine 2000 (2 μL, the actual concentration of which is undisclosed by the commercial supplier) reduced the viability of HeLa-Luc cells by 35%, whereas CRC5 (6.6 μg/mL or ~0.5 μM) showed no detectable cytotoxicity (FIG. 7).

Example 2. Polypeptide Conjugate with One cCPP Terminal

Design and Synthesis. While the CRC polymers described in Example 1 are effective for siRNA delivery and simple to prepare, they are mixtures of different species, the precise MWs and structures of which can be more difficult to characterize.

In this example, a cyclic CPP was covalently linked to a 3,5-bis(mercaptomethyl)benzoyl (Bmb) moiety through a long, flexible linker, miniPEG-lysine (Scheme 1). CPP12, which has cytosolic delivery efficiency of 121%, was selected for this design (see Qian, 2016). Two polyarginine peptides (R5, R10, or R15) are conjugated to the Bmb scaffold through disulfide bonds. We envisioned that the two polyarginine peptides would bind tightly to double-stranded siRNA via electrostatic interactions, leaving the cyclic CPP exposed for cellular uptake. Upon entering the cytosol, the disulfide bonds would be cleaved by GSH, releasing the siRNA for biological function.

Scheme 1. Nucleic acid delivery vector B. A) Schematic representation of the between the binding interaction polyarginine segments and siRNA and decomposition/dissociation of the vector/siRNA complex in the presence of GSH. B) Structure of delivery vector CPP12-(Rn)2.

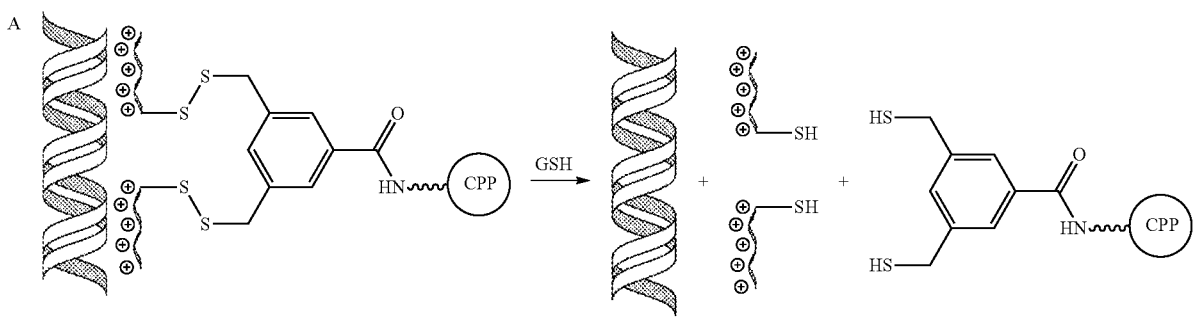

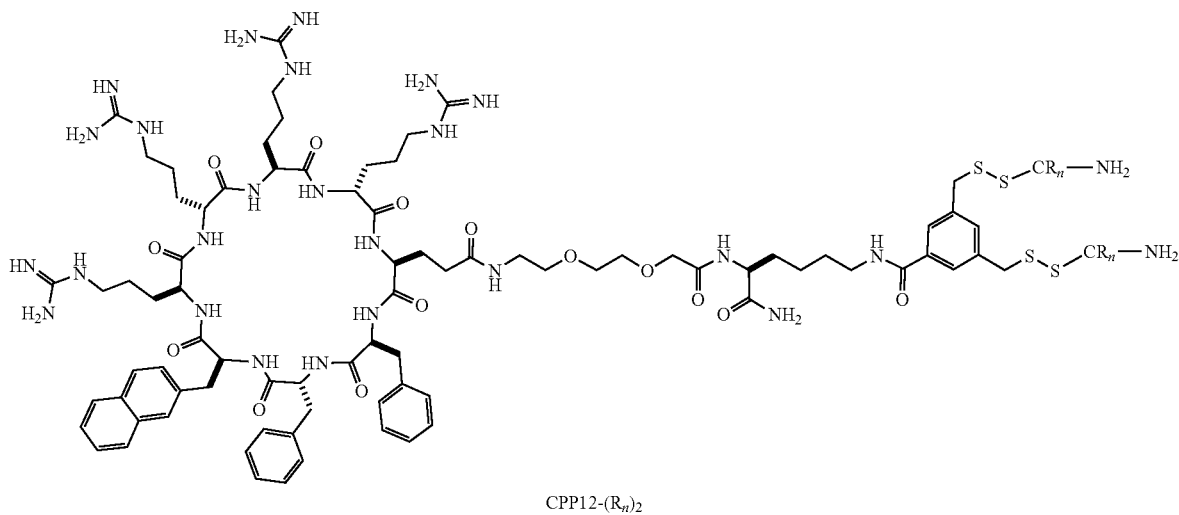

CPP12-(R$_n$)$_2$ n = 5, 10, or 15

Figure 8:
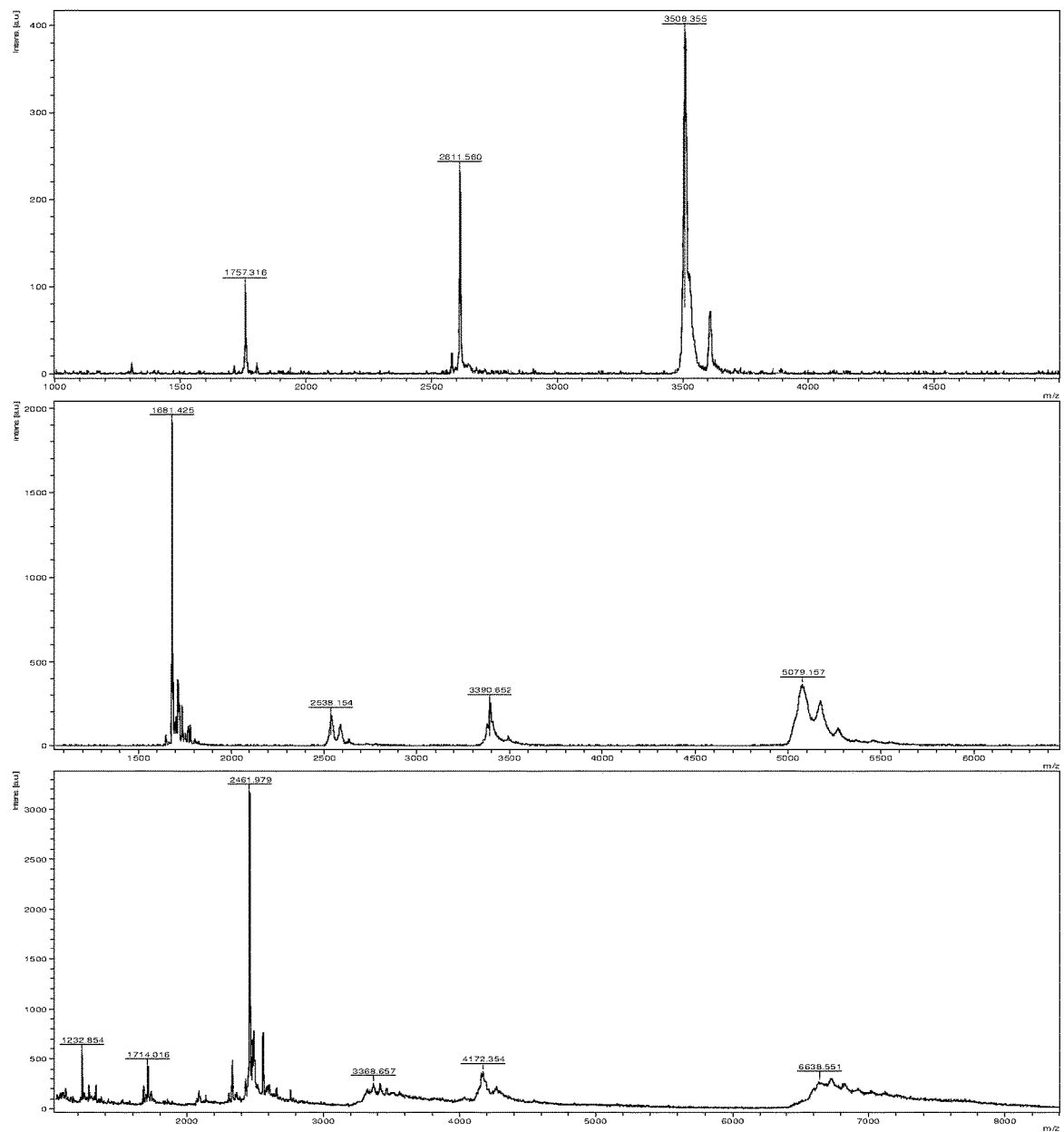
FIG. 8 shows MALDI-TOF MS spectra of CPP12-$(R_5)_2$ (top), CPP12-$(R_{10})_2$ (middle), and CPP12-$(R_{15})_2$ (bottom).

The cCPP-polyarginine conjugate was prepared by first synthesizing CPP12-miniPEG-Lys(Mtt)-NH$_2$ on Rink amide resin. The Mtt group on the lysine side chain was selectively removed by treatment with 2% TFA and bis(trityl)-protected Bmb was coupled to the lysine side chain with Oxyma/DIC/DIPEA as coupling reagents. The resulting peptide, CPP12-miniPEG-Lys(Bmb)-NH$_2$, was cleaved from the resin and side chain deprotected using the standard conditions and purified by reversed-phase HPLC. The freshly eluted peptide was treated with an excess of 2,2'-dithiodipyridine to protect (and activate) the two thiol groups of Bmb. Meanwhile, the polyarginine peptides CR$_n$, where n=5, 10 or 15, were synthesized on the solid phase with a cysteine residue added at the N-terminus. After deprotection, cleavage, and HPLC purification, the CR$_1$ peptide was mixed with the thiopyridylated CPP12 at neutral pH to afford the conjugates CPP12-(R$_n$)$_2$. The identity of the vectors was confirmed by MALDI-TOF mass spectrometry (Table 6, FIG. 8). In FIG. 8: MALDI-TOF MS spectra of CPP12-(R$_5$)$_2$ (top), CPP12-(R$_{10}$)$_2$ (middle), and CPP12-(R$_{15}$)$_2$ (bottom).

TABLE 6

MW of CPP12-(R$_n$)$_2$ polymers

Figure 12:
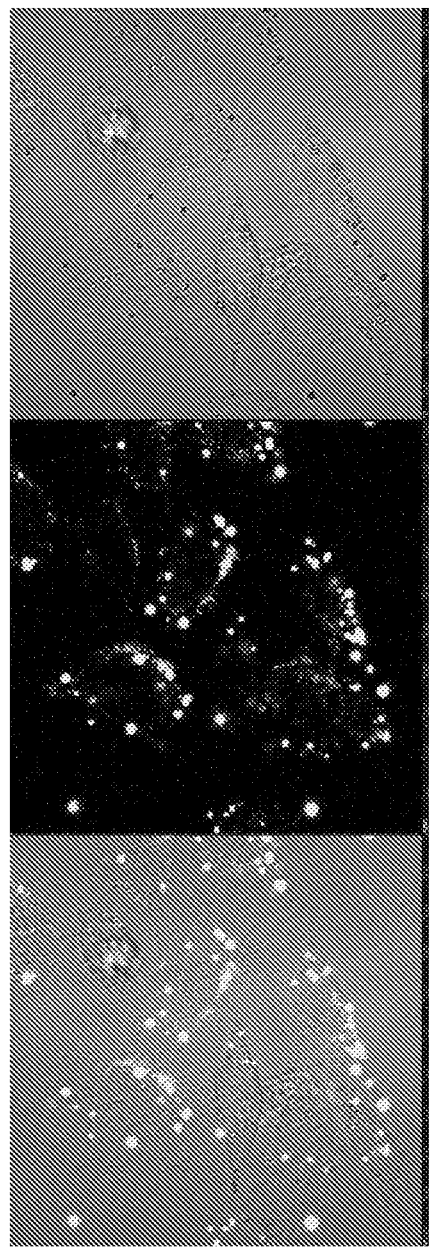
FIG. 12 shows live-cell confocal microscope images of HeLa cells treated with the (CPP9-$R_5)_2$/5'-FAM-siLuc complex (Example 3) at 3 μM siRNA. Center, GFP channel; Right, DIC; and left, overlap of the above.

| Polymer | MW | |
|---|---|---|
| | calculated | observed |
| CPP12-(R$_5$)$_2$ | 3510 | 3508 |
| CPP12-(R$_{10}$)$_2$ | 5076 | 5079 |
| CPP12-(R$_{15}$)$_2$ | 6636 | 6638 | siRNA Binding. CPP12-(R$_5$)$_2$, CPP12-(R$_{10}$)$_2$ and CPP12-(R$_{15}$)$_2$ were tested for binding to siLuc by the gel retardation method using various N/P ratios as described above. The CPP12-(R$_n$)$_2$/siRNA complexes were formed with a fixed concentration of siRNA and increasing concentrations of CPP12-(R$_n$)$_2$ to give N/P ratios of 0.5:1 to 10:1. Free siRNA was used as a control. Complete conversion of free siRNA into the RNA/polymer complex was observed at an N/P ratio of 5 for CPP12-(R$_5$)$_2$ and N/P ratio of 3 for CPP12-(R$_{10}$)$_2$ and CPP12-(R$_{15}$)$_2$. Treatment of the preformed siLuc/CPP12-(R$_5$)$_2$ complex with 10 mM DTT resulted in a discrete band with the same mobility as the free RNA (FIG. 12, top right). On the other hand, similar treatment of the siLuc/CPP12-(R$_{10}$)$_2$ and siLuc/CPP12-(R$_{15}$)$_2$ complexes with 10 mM DTT did not result in a discrete RNA band (FIG. 12, middle and bottom right), indicating that R$_{10}$ and R$_{15}$ remain bound to siRNA after DTT treatment.

Cellular Uptake. 5'-FAM-labelled siLuc (3 µM) was mixed with CPP12-(R$_5$)$_2$ at an N/P ratio of 5 in OptiMEM medium. HeLa cells were treated with the CPP12-(R$_5$)$_2$/5'-FAM-siRNA complex for 2 h. Cells were washed and imaged by confocal microscopy as described above. Interestingly, CPP12-(R$_5$)$_2$ and 5'-FAM-siRNA formed large, insoluble particles of nanometer sizes (FIG. 9). In FIG. 9: center, GFP channel; right, DIC; and left, overlap of the above. Although some of the labeled siRNA was internalized by the cells, the intracellular fluorescence level was lower than that obtained with the copolymer of Example 1.

Figure 10:
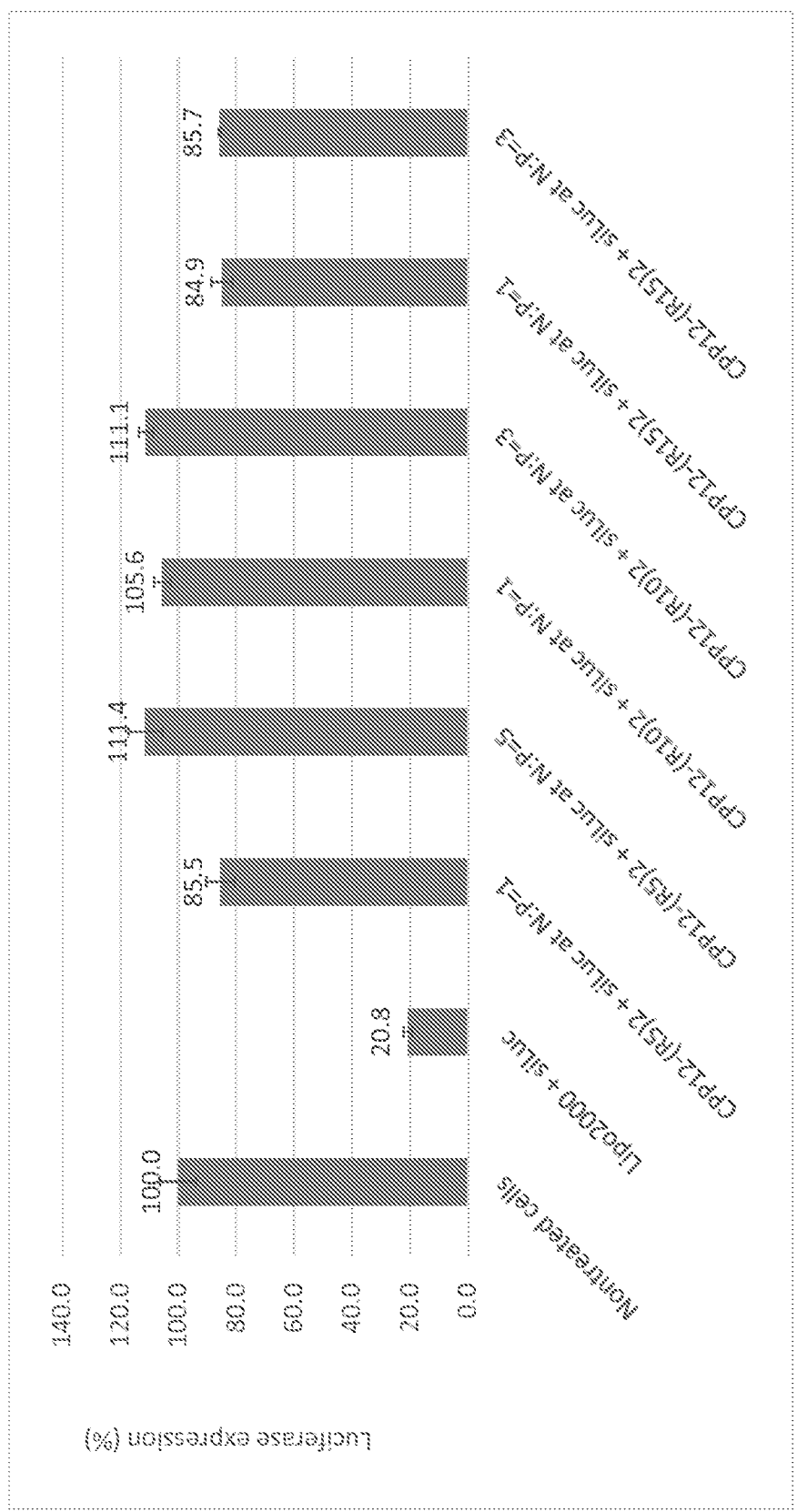
FIG. 10 shows knockdown of luciferase expression in HeLa-Luc cells by CPP12-$(R_n)_2$/siLuc complexes (Example 2, 75 nM) and lipofectamine/siLuc complex at 48 h after treatment.

Knockdown of Luciferase Expression. The ability of CPP12-(R$_n$)$_2$ to deliver siLuc intracellularly was tested on HeLa-Luc cells as described above. CPP12-(R$_n$)$_2$/siLuc complexes were formed at various N:P ratios by mixing CPP12-(R$_n$)$_2$ with siLuc in 20 mM HEPES, pH 7.4 followed by 15 min incubation. The complexes were then mixed with OptiMEM medium, added to cells, and incubated at 37° C. for 48 h. Lipofectamine2000/siLuc was used as a positive control. As shown in FIG. 10, treatment of HeLa-Luc cells with the CPP12-(R$_n$)$_2$/siLuc complexes (75 nM siLuc) at N:P ratios of 1 to 5 only slightly reduced the expression of the luciferase (≤15%), in agreement with their inefficient cellular uptake (FIG. 9).

Example 3. Modification of Peptide Conjugate in Example 2

Figure 11:
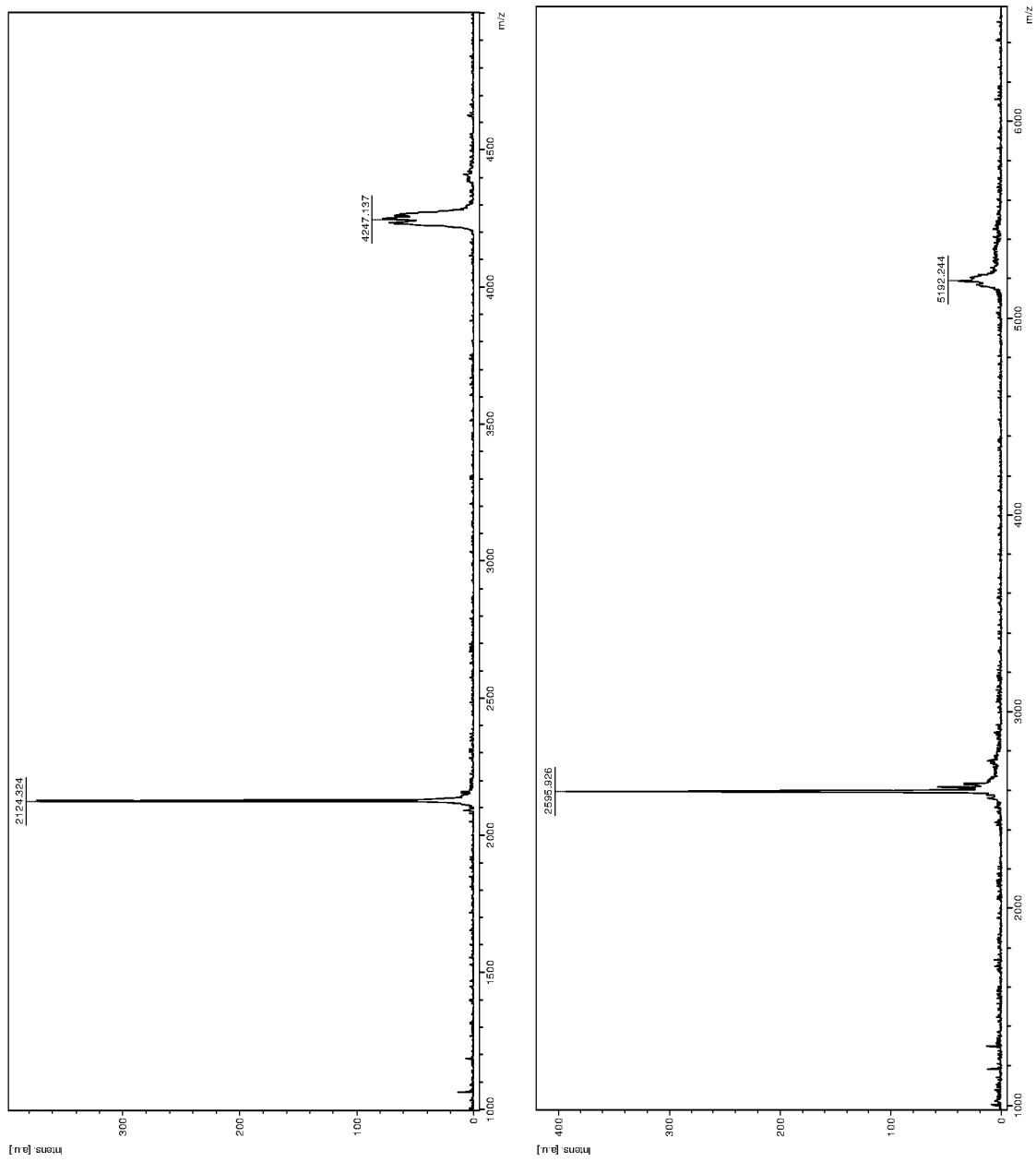
FIG. 11 shows MALDI-TOF MS spectra of (CPP9-$R_5)_2$ (top) and (CPP9-$R_8)_2$ (bottom).

Design and Synthesis. In modifying the peptide conjugate of Example 2, cyclic CPP (e.g., CPP9) was directly attached to a polyarginine peptide (R$_n$) through a miniPEG linker. A cysteine was added to the C-terminus of the peptide. The entire molecule was readily synthesized by standard solid-phase peptide chemistry, cleaved off the solid support, deprotected, and purified by HPLC. Exposure of the peptide to an oxidant (e.g., DMSO) resulted in homodimerization through the formation of a disulfide between the C-terminal cysteines. Again, the $(R_n)_2$ moiety (where n=5 or 8) in the central section is expected to bind to siRNA with high affinity in the oxidizing extracellular environment, whereas the two terminal CPPs would mediate endocytic uptake. Once inside the cytosol, the disulfide bond would be, without bound to any theory, reduced and the siRNA would be released. One advantage of this design was thought to be that the presence of two CPPs should enhance the cellular uptake efficiency of the vector (relative to Example 2). The identity of the synthesized peptide conjugate was determined by MALDI-TOF mass spectrometry (Table 7 and FIG. 11). In FIG. 11, MALDI-TOF mass spectra of (CPP9-$R_5)_2$ (top) and (CPP9-$R_8)_2$ (bottom).

which are clearly visible under the microscope. Internalization of the complex by HeLa cells was also evident and somewhat more efficient than the $1^{st}$-generation vector (FIG. 12). In FIG. 12, Center, GFP channel; Right, DIC; and left, overlap of the above.

Figure 13:
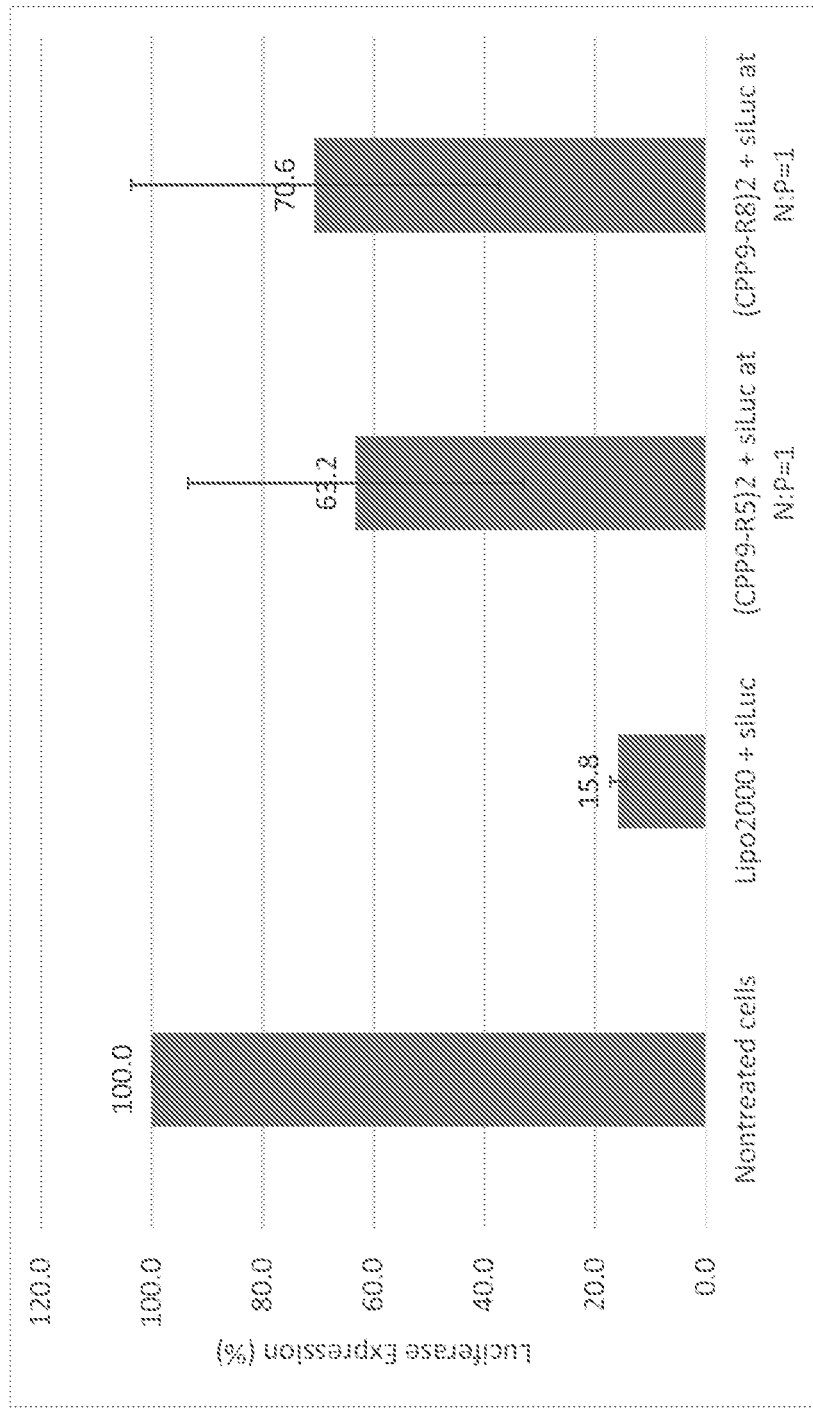
FIG. 13 shows knockdown of luciferase expression in HeLa-Luc cells by CPP9-$R_n)_2$/siLuc complexes (Example 3, 75 nM) and lipofectamine/siLuc complex at 48 h after treatment.

Knockdown of Luciferase Expression. The ability of (CPP9-$R_n)_2$ vectors to deliver siLuc intracellularly was tested on HeLa-Luc cells as described above. (CPP9-$R_n)_2$/siLuc complexes were formed at different N:P ratios by mixing (CPP9-R)$_2$ with siLuc in 20 mM HEPES, pH 7.4 followed by 15 min incubation. Complexes were then mixed with OptiMEM, added to the cells and incubated at 37° C. for 48 h. Lipofectamine2000/siLuc was used as a positive control. Treatment of HeLa-Luc cells with the (CPP9-$R_5)_2$/siLuc and (CPP9-$R_8)_2$/siLuc complexes at N:P ratio of 1:1 (75 nM siLuc) decreased the luciferase activity by 30-35% (FIG. 13). Interestingly, the (CPP9-$R_8)_2$/siLuc complex was

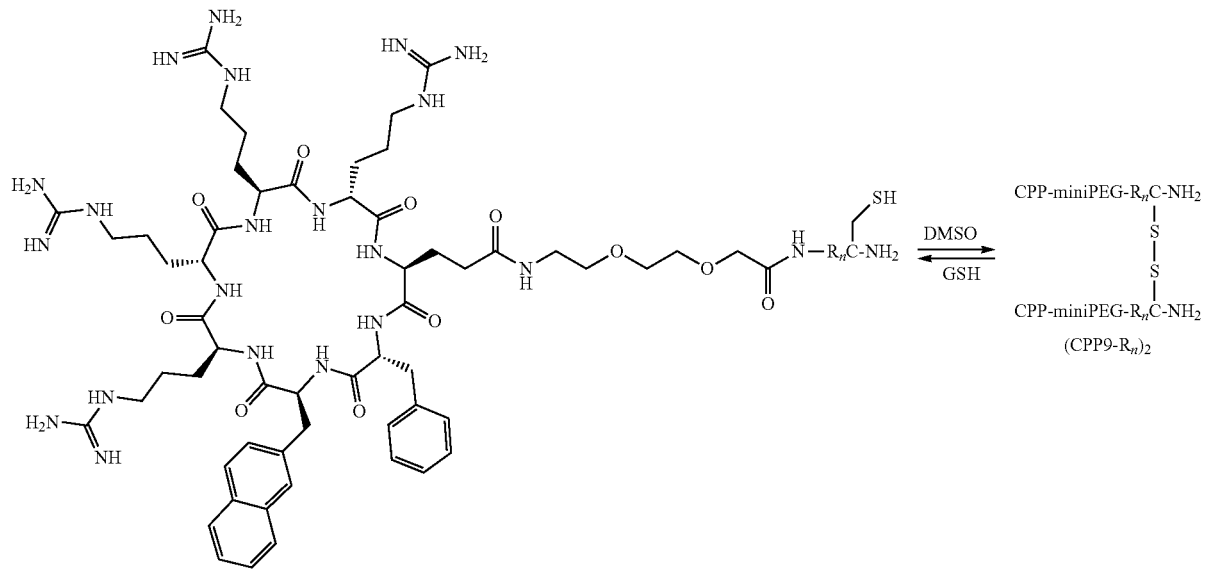

TABLE 7

MW of (CPP9-$R_n)_2$ polymers

| Polymer | MW calculated | MW observed |
|---|---|---|
| (CPP9-$R_5)_2$ | 4250 | 4247 |
| (CPP9-$R_8)_2$ | 5190 | 5192 | siRNA Binding. (CPP9-$R_5)_2$ and (CPP9-$R_8)_2$ were evaluated for binding to siLuc by the gel retardation method at various N/P ratios as described above. The (CPP9-$R_n)_2$/siRNA complexes were formed with a fixed concentration of siRNA and increasing concentrations of CPP12-($R_n)_2$ to give N/P ratios of 0.5:1 to 20:1. Free siRNA was used as a control. Complete conversion of free siRNA into the RNA/polymer complex was observed at an N/P ratio of 3 for (CPP9-$R_5)_2$ and N/P ratio of 1 for (CPP9-$R_8)_2$.

Cellular Entry by Confocal Microscopy. 5'-FAM-labelled siLuc (3 M) was mixed with (CPP9-$R_5)_2$ at an N/P ratio of 2 in OptiMEM. HeLa cells were seeded and washed as described above and treated with the (CPP9-$R_5)_2$/5'-FAM-siRNA complex for 2 h. Cells were washed and imaged as described above. The complex formed insoluble aggregates slightly less effective than the (CPP9-$R_5)_2$/siLuc complex, likely because of the less efficient release of siRNA from the former.

Example 4. Modification of Peptide Conjugate in Example 2

Figure 14:
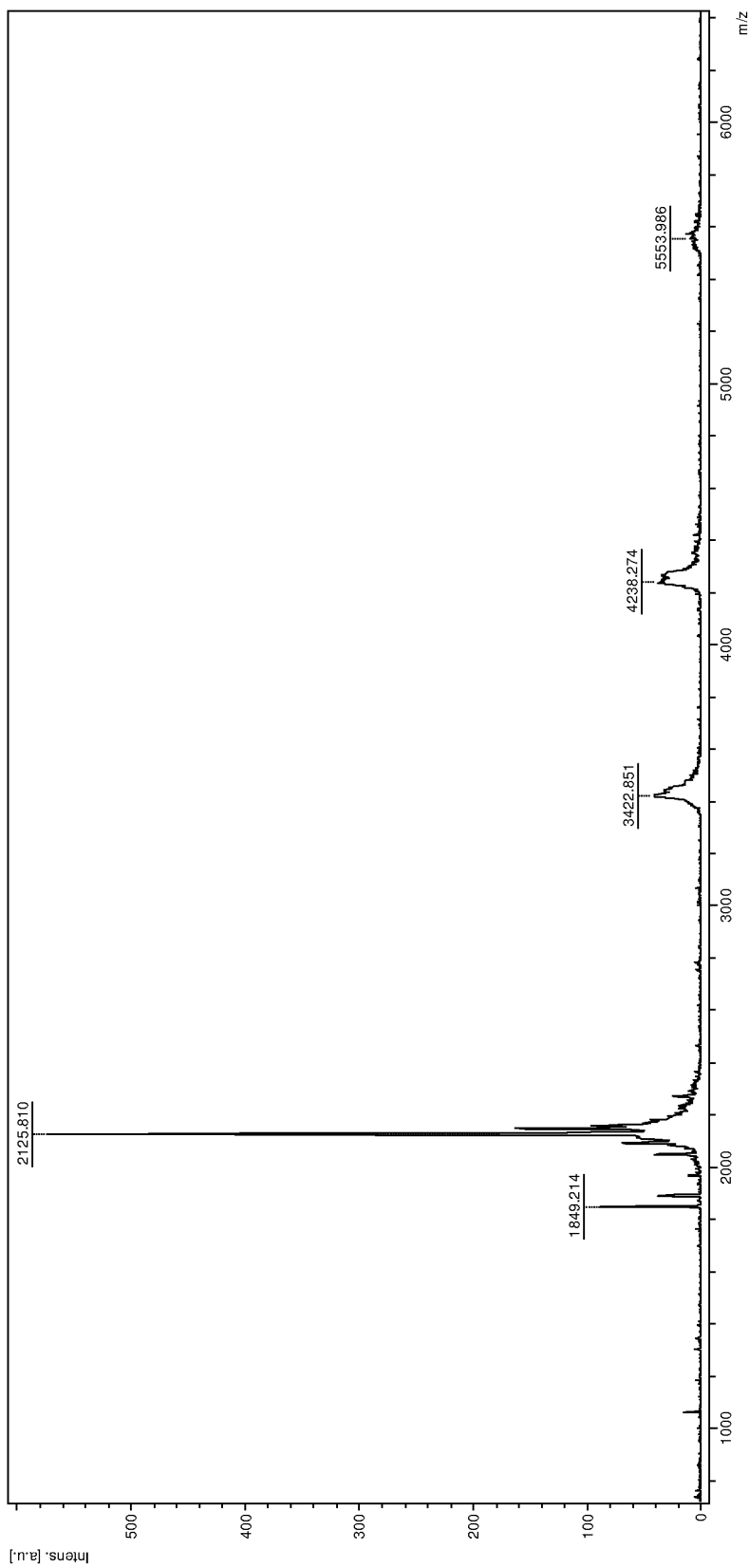
FIG. 14 shows MALDI-TOF MS spectra of the polypeptide conjugate synthesized according to Example 4.

Design and Synthesis. The above Examples suggest that for optimal siRNA delivery efficiency, the polyarginine moiety should have sufficient length to bind to siRNA with high affinity and interact with entire length of the siRNA to prevent it from nuclease action. Once inside the cell, the polymer must be broken down into small fragments that readily dissociate from the siRNA. The polypeptide conjugate of this Example has the general structure of CPP9-$R_5$—S—S—$R_6$—S—S—$R_5$-CPP9 (SEQ ID NO: 144), which consists of two cyclic CPP9-miniPEG-$R_5$ (SEQ ID NO: 142) units covalently linked to an internal $R_6$ (SEQ ID NO: 143) unit through two disulfide bonds. The polypeptide conjugate of this Example is structurally very similar to the copolymers from Example 1, but can be readily synthesized as a single species. Briefly, the CPP9-miniPEG-$R_5$-Cys (SEQ ID NO: 145) unit was synthesized by standard solid-phase peptide chemistry and reacted with dithiodipyridine to give the thiopyrodylated form, which is stable upon storage. The internal $R_6$ unit has a Cys-β-Ala dipeptide on each side to give some flexibility to the polymer structure. Simply mixing a 2:1 ratio (mol/mol) of the CPP9-miniPEG-$R_5$ (SEQ ID NO: 142) and $R_6$ (SEQ ID NO: 143) units at the physiological pH gave the desired polymer as the predominant species, which was purified to homogeneity by reversed-phase HPLC. The identity of polypeptide conjugate of this Example was confirmed by MALDI-TOF mass spectrometry (FIG. 14).

Figure 16:
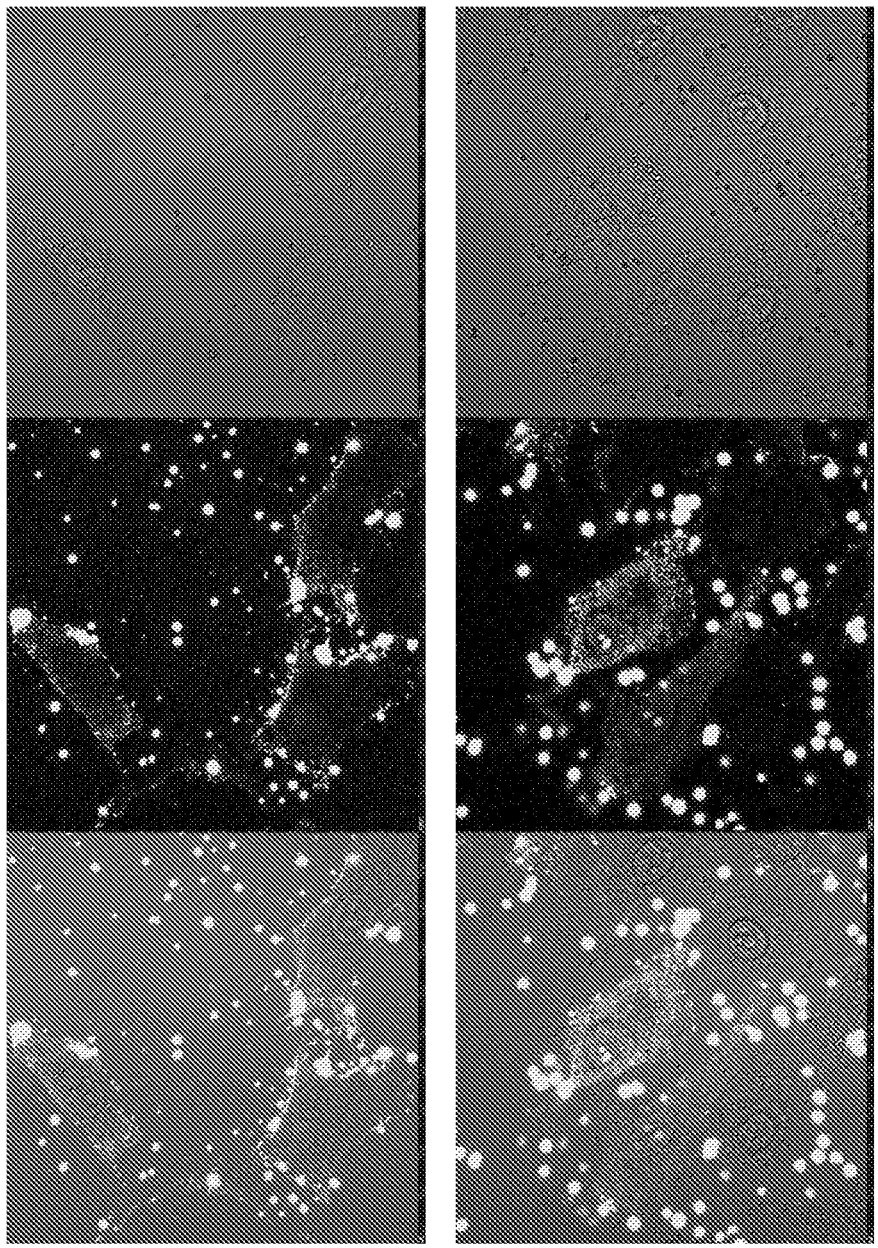
FIG. 16 shows live-cell confocal microscope images of HeLa cells treated with the polypeptide conjugate synthesized according to Example 4/5'-FAM-siLuc complex at 1 μM siRNA in DMEM with 1% FBS (top) or 3 μM siRNA in OptiMEM (bottom). Center, GFP channel; Right, DIC; and left, overlap of the above.

FBS. HeLa cells were treated with the polypeptide conjugate of this Example/5'-FAM-siRNA complex for 2 h. Cells were washed and imaged by live-cell confocal microscopy. Cellular entry of the polypeptide conjugate of this Example/5'-FAM-siRNA complex was more efficient than the Examples 2 or 3, and the diffuse fluorescence throughout the entire cell volume indicate that the complex had escaped from the endosome into the cytosol and nucleus (FIG. 16). Formation of insoluble aggregates was still observed. In FIG. 16, at 1

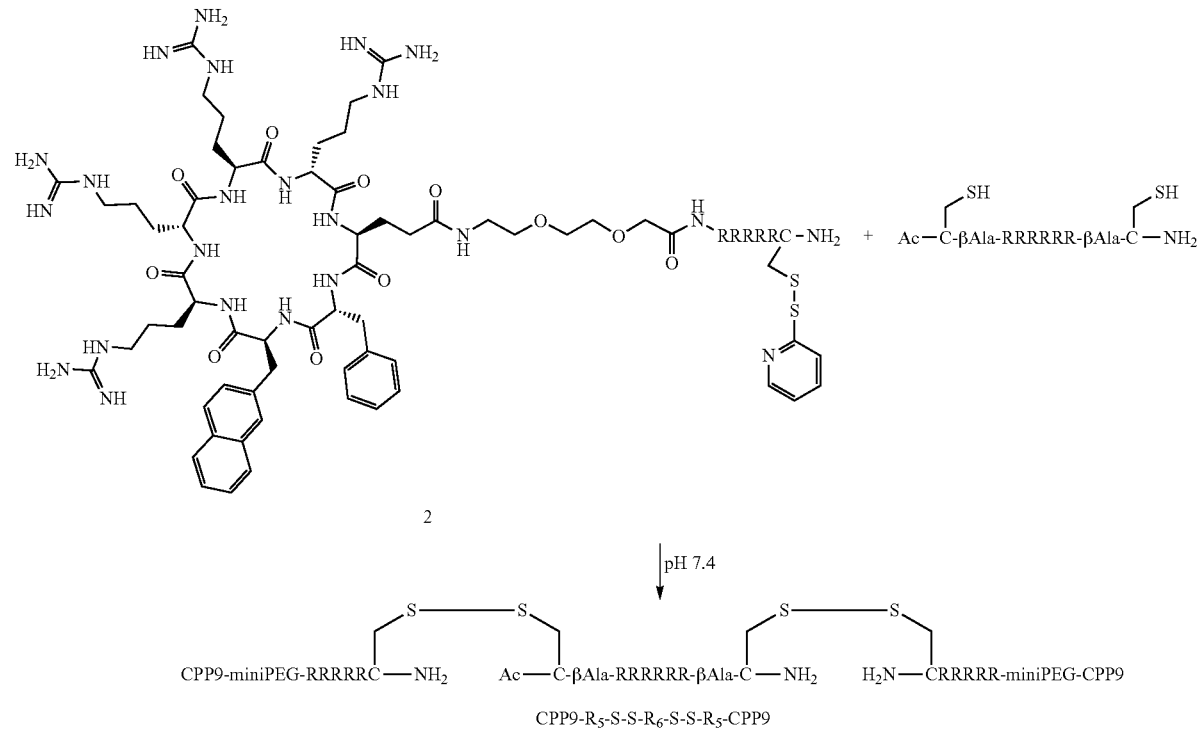

μM siRNA in DMEM with 1% FBS (top) or 3 μM siRNA in OptiMEM (bottom). Center, GFP channel; Right, DIC; and left, overlap of the above.

Figure 17:
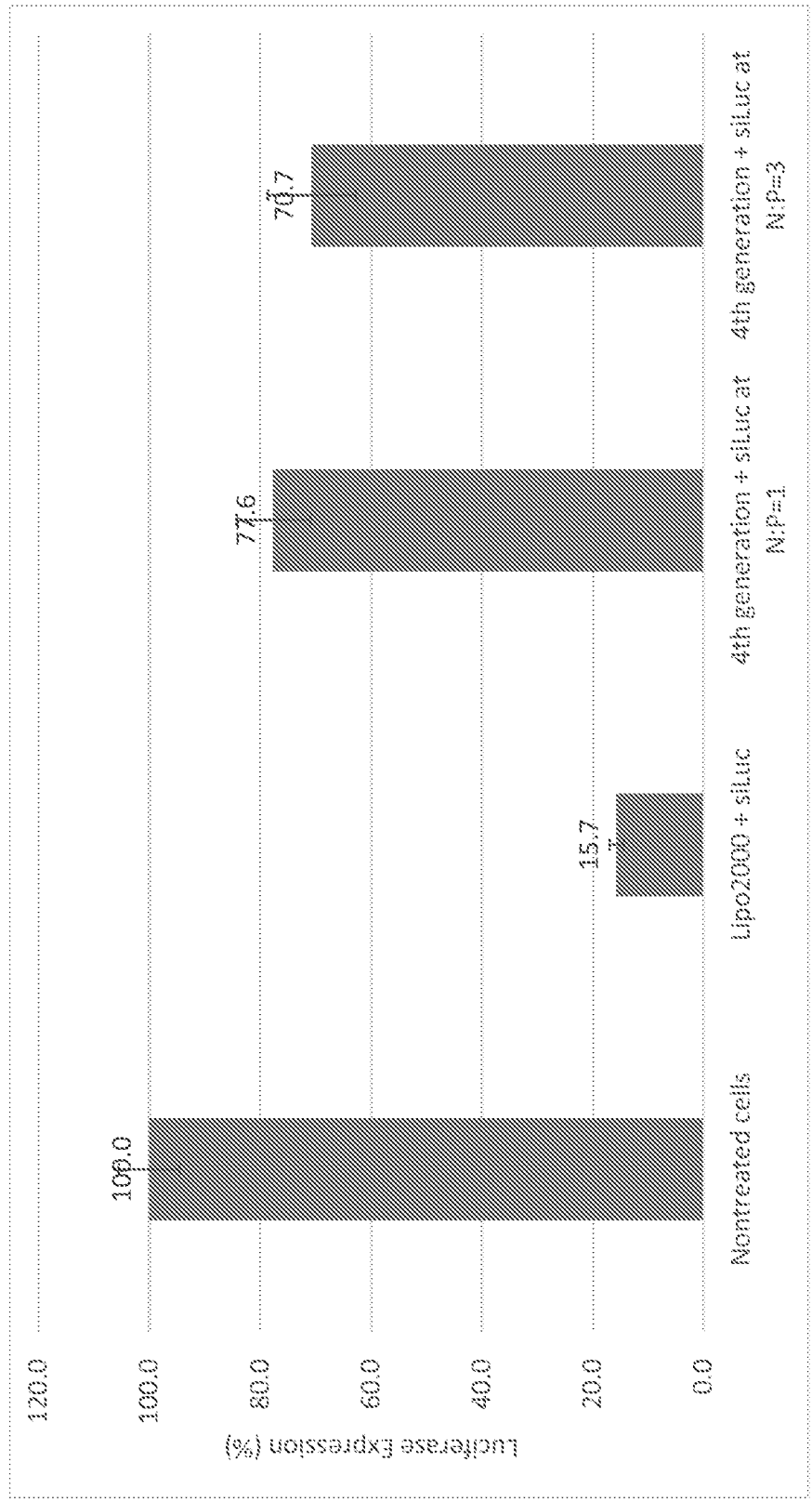
FIG. 17 shows knockdown of luciferase expression in HeLa-Luc cells by the polypeptide conjugate of Example 4/siLuc complexes (Example 4, 75 nM) and lipofectamine/siLuc complex at 48 h after treatment.

Knockdown of Luciferase Expression. Treatment of HeLa-Luc cells with the 3 polypeptide conjugate of this Example/siLuc complexes at N:P ratios of 1:1 and 3:1 (both at 75 nM siLuc RNA) for 48 h at 37° C. reduced the luciferase expression by 22% and 29%, respectively. Under the same conditions, the lipofectamine2000/siLuc complex reduced the luciferase expression by 84% (FIG. 17).

Figure 15:
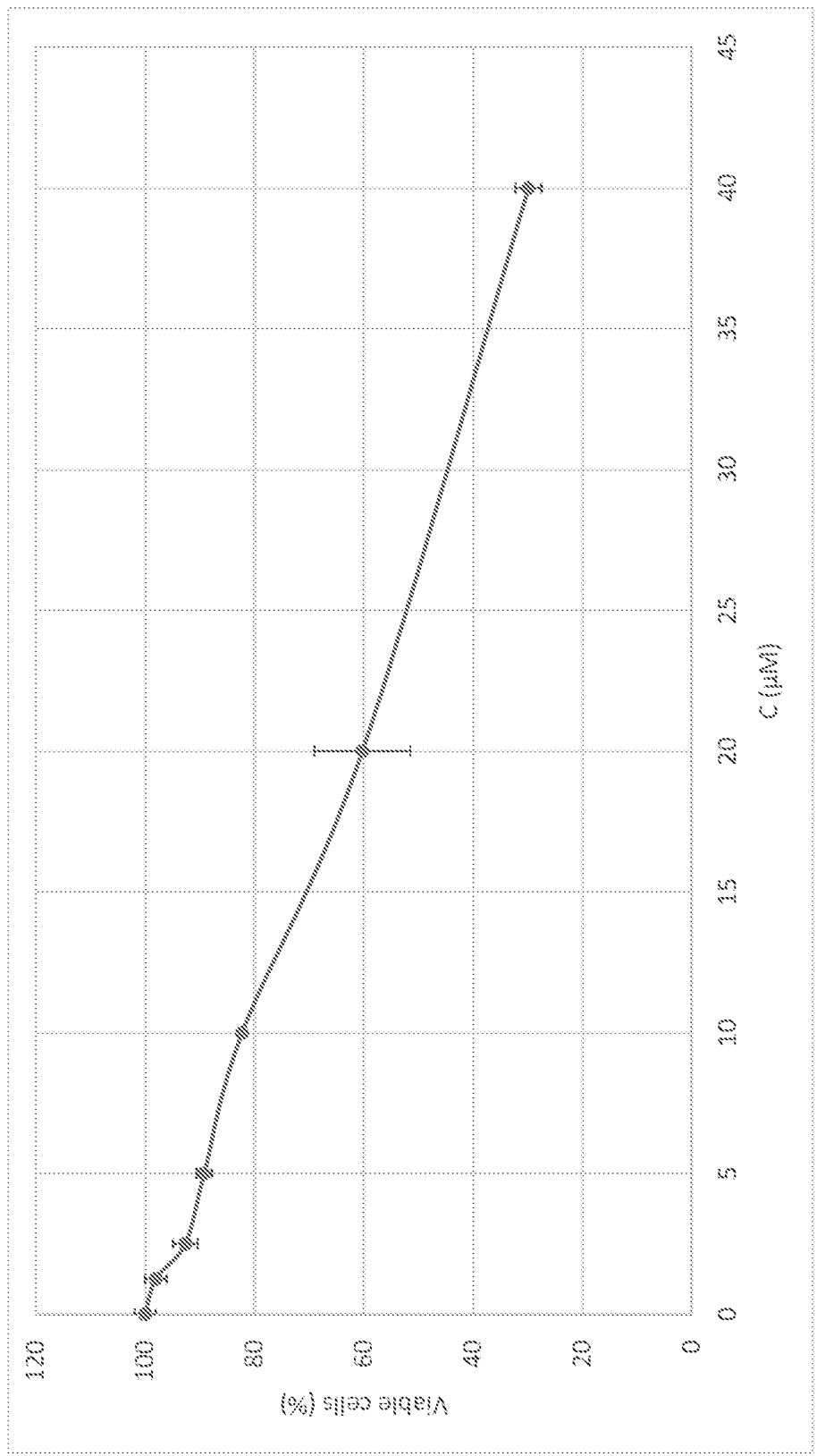
FIG. 15 shows the effect of the polypeptide conjugate synthesized according to Example 4 on HeLa cells as assayed by the MTT test.

Knockdown of Firefly Luciferase Expression Normalized by Renilla luciferase Expression. The ability of CRC polymers to deliver siRNA intracellularly was tested on a HeLa cell line stably transfected with Firefly and Renilla luciferase genes (Dual-HeLa). Firefly luciferase serves as an experimental reporter, while Renilla luciferase serves as a control reporter allowing to normalize the specific gene silencing of an experimental reporter. The siLuc sequences used were: sense 5'-AAmCGmCmUGGGmCGmUmUAA-mUmCAAdTdT-3' (SEQ ID NO: 139) and antisense 5'-UUGAUmUAACGCCmCAGCGUUdTdT-3' (SEQ ID NO: 140). Dual-HeLa cells were seeded onto white 96-well plates at a density of 1.0×104 cells/well in 100 μL of DMEM containing 10% FBS and cultured overnight. CRC5/siLuc complexes were formed by mixing CRC5 with siLuc in 20 mM HEPES, pH 7.4 followed by 15 min incubation. Com- Cytotoxicity. The polypeptide conjugate of this Example was tested for cytotoxicity against HeLa cells using the MTT assay. HeLa cells were treated with varying concentrations (0-40 μM) of the 3rd-generation vector and incubated at 37° C. with 5% $CO_2$ for 72 h. Cells were treated with MTT stock solution and SDS-HCl solubilizing buffer as described above. The absorbance of the formazan product was measured at 570 nm on a Tecan M1000 plate reader. In contrast to the copolymers, which caused ≤20% reduction in viability up to 40 M concentration (FIG. 5A), the polypeptide conjugate of this Example reduced the viability of HeLa cells in a dose-dependent manner, by 70% at 40 M (FIG. 15).

siRNA Binding. The polypeptide conjugate of this Example was able to bind siLuc. Complete conversion of free siRNA into the siRNA/vector complex was observed at an N/P ratio of 2. Treatment of the preformed siLuc/vector complex with 10 mM DTT did not regenerate the free siRNA band; instead, a broad, smeared siRNA band was observed, indicating that siRNA remained bound to the polyarginine species even after reduction of the disulfide bonds.

Cellular Uptake by Confocal Microscopy. 5'-FAM-labelled siLuc (1 or 3 M) was mixed with the 3rd-generation vector at an N/P ratio of 2 in OptiMEM or DMEM with 1% plexes were then mixed with OptiMEM, added to cells and incubated at 37° C. for 48 h. Lipofectamine 2000/siLuc was used as a positive control. Lipofectamine 2000 was complexed with siRNA according to the manufacturer's protocol. Dual-Glo Luciferase Assay System (Promega, USA) was used to quantitate the luciferase gene silencing level according to manufacturer's protocol. Luminescence was measured on a Tecan Infinite M1000 plate reader.

Figure 18:
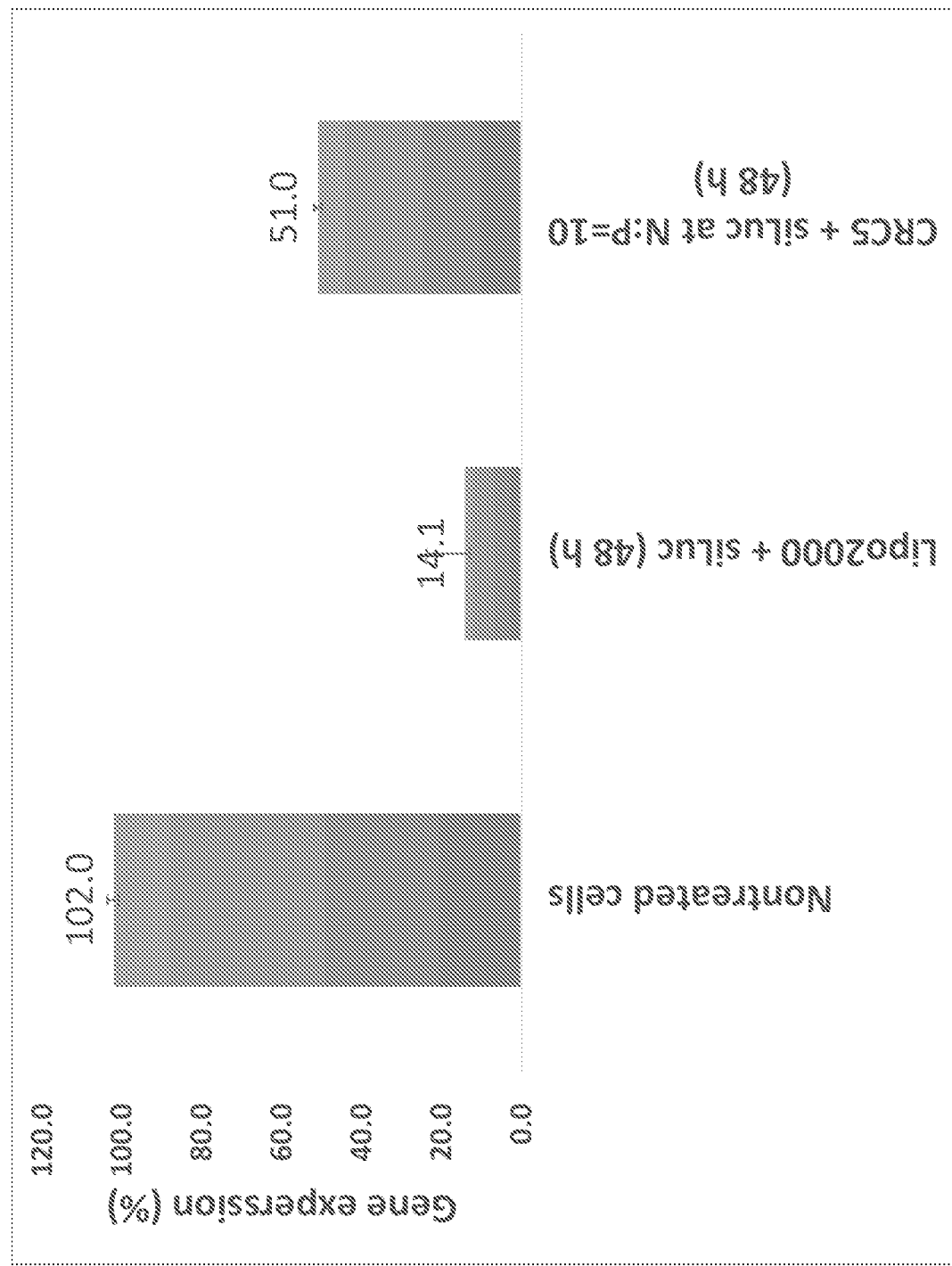
FIG. 18 is a graph of gene expression (%) with cells treated with SiLuc and either Lipo2000 or CRC5.

Treatment of HeLa-Luc cells with the CRC5/siLuc complex decreased the Firefly luciferase activity by 49% at an N:P ratio=10 ([siLuc]=75 nM and 6.6 µg/mL CRC5) after 48 h of incubation after normalization by Renilla luciferase expression (FIG. 18). Under similar conditions, Lipofactamine 2000 resulted in 86% reduction.

Knockdown of GFP Expression. The ability of CRC polymers to deliver siRNA intracellularly was also tested on a HeLa cell line stably transfected with GFP gene (HeLa-GFP). The siGFP used in this experiment was Silencer™ GFP (eGFP) siRNA (#AM4626, Thermo Fisher, USA). HeLa-GFP cells were seeded onto 96-well plate at a density of $1.0 \times 10^4$ cells/well in 100 µL of DMEM containing 10% FBS and cultured overnight. CRC5/siLuc complexes were formed by mixing CRC5 with siLuc in 20 mM HEPES, pH 7.4 at N:P=10 followed by 15 min incubation. Complexes were then mixed with OptiMEM, added to cells and incubated at 37° C. for 48 h. Lipofectamine 2000/siLuc was used as a positive control. After incubation cells were lysed on ice for 30 min in IP lysis buffer supplemented with protease and phosphatase inhibitors. Cell lysates were centrifuged and 15000 rpm for 10 min, and the extracted proteins were collected. Protein concentration was measured using a BCA Protein Assay Kit (Thermo Fisher, USA) and equal amount of total proteins (~200 ng) were added to a black 384-well plate. Fluorescence intensity was measured at 510 nm on a Tecan Infinite M1000 plate reader.

Figure 19:
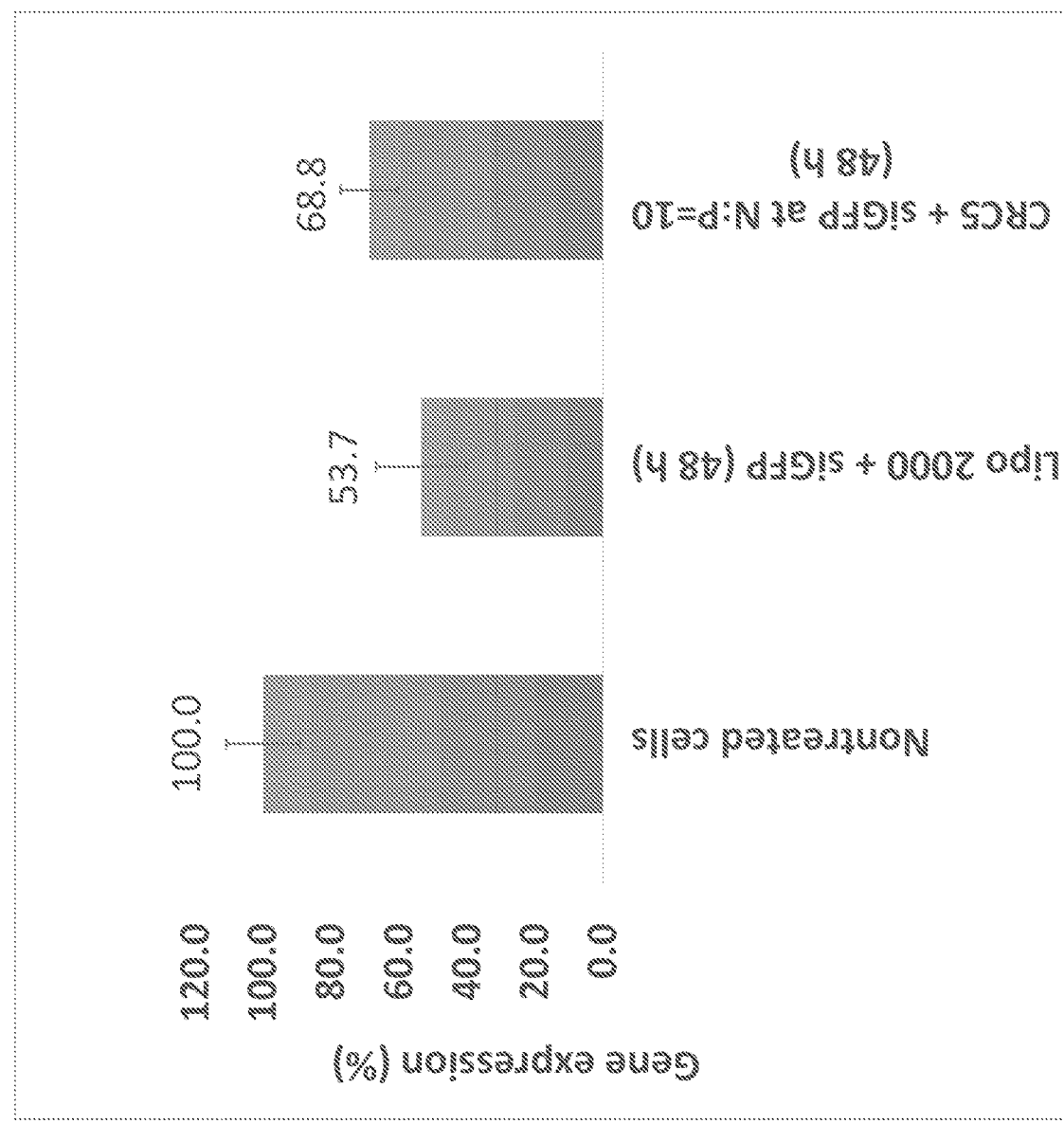
FIG. 19 is a graph of gene expression (%) with cells treated with SiGFP and either Lipo2000 or CRC5.

Treatment of HeLa-GFP cells with the CRC5/siGFP complex at N:P ratio=10 ([siLuc]=75 nM and 6.6 g/mL CRC5) decreased the GFP expression by 31% after 48 h of incubation, which was comparable to the efficiency of Lipofectamine 2000 (46%; FIG. 19).

Discussion (Examples 1-4)

Without bound to any theory, the ideal siRNA delivery vector (polypeptide conjugates) should bind to siRNA with high affinity and interact with the entire siRNA molecule to prevent the latter from nuclease action. Once inside the cell, however, the vector should be readily broken down into small fragments that readily dissociate from the siRNA. In addition, because liposome- and nanoparticle-based siRNA delivery systems often resulted in accumulation of siRNA in well-vascularized tissues such as the liver, spleen, and kidney, soluble, oligomeric vector/siRNA complexes (ideally 1:1 vector/siRNA complex) which should have better tissue penetration and potentially broader distribution in vivo are desirable. All four siRNA delivery vectors described in the Examples are capable of delivering siRNA into mammalian cells and knocking down the expression of luciferase gene, but meet the above design criteria to different extents. Overall, the polypeptide of Example 1 demonstrated better performance than Examples 2-3. It very effectively delivers siRNA into the cytosol of mammalian cells (as evidenced by confocal microscopy) and most efficiently knocks down luciferase expression. It exhibited minimal cytotoxicity to HeLa cells at up to 40 M concentration. It did not form any insoluble species (i.e., nanoparticles). It is also operationally very simple to prepare. The challenge with Example 1's polypeptide conjugate may be its structural heterogeneity (i.e., different number of $R_5$ units in the copolymer), which may requires extra attention during their preparation in order to produce copolymers of consistent compositions.

The three vectors as prepared according to Examples 2-4, on the other hand, have well-defined structures (single species) and are readily prepared in pure forms. However, the challenge was the formation of insoluble aggregates and generally having lower siRNA delivery efficiencies and higher cytotoxicities. Presumably, without bound to any theory, their smaller sizes (compared to the conjugate of Example 1) result in weaker binding to siRNA when outside the cell and during endocytic uptake. Because their polyarginine sections may be too short to cover the entire siRNA surface, the cCPPs at the termini may bind to the siRNA as well, potentially interfering with their membrane binding and CPP function. At the same time, binding of multiple polyarginine peptides to one siRNA molecule (and/or multiple siRNA molecules to the same polyarginine peptide) could condense nucleic acids into large, insoluble nanoparticles, as was commonly observed for other arginine-rich CPPs such as Tat (see Arthanari, Y. et al., *J. Controlled Release* 2010, 145, 272-280) and R9 (see Law, M. et al., *Biotechnol Prog.*, 2008, 24, 957-963). After cytosolic entry and reduction of the disulfide bonds, the fragments derived from the vectors in Examples 2-4 contain 9 or more arginine residues [except for CPP9-$(R_5)_2$]. As demonstrated by gel electrophoresis in Examples 2 and 4, these fragments remain tightly associated with the siRNA and reduce the knockdown efficiency of the siRNA. Additionally, the polyarginine fragments may bind to endogenous nucleic acids inside the cell, causing cytotoxicity. In comparison, reduction of the copolymer of Example 1 produces fragments with 5 or less arginine residues, which without bound to any theory do not bind to siRNA or other nucleic acids with high affinity as demonstrated by gel electrophoresis in Examples 1.

The Examples demonstrate that the copolymerization of cCPPs and pentaarginine peptides through disulfide bonding generated a family of cationic copolymers that bind siRNA with high affinity, effectively deliver them into the cytosol of mammalian cells, and then release them for functional knockdown of specific mRNA levels. This novel delivery method would be useful in delivering nucleic acids to target cells.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

SEQUENCE LISTING

<160> NUMBER OF SEQ ID NOS: 145

<210> SEQ ID NO 1
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 1

Phe Xaa Arg Arg Arg Gln
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 2

Phe Xaa Arg Arg Arg Cys
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (6)..(6)
<223> OTHER INFORMATION: Xaa is selenocysteine

<400> SEQUENCE: 3

Phe Xaa Arg Arg Arg Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is L-2-naphthylalanine

<400> SEQUENCE: 4

Arg Arg Arg Xaa Phe Gln
1               5

<210> SEQ ID NO 5
<211> LENGTH: 6
<212> TYPE: PRT
<213> ORGANISM: Artificial Sequence -continued

```
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is L-2-naphthylalanine

<400> SEQUENCE: 5

Arg Arg Arg Arg Xaa Phe
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 6

Phe Xaa Arg Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-2-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamine

<400> SEQUENCE: 7

Phe Xaa Xaa Arg Xaa Arg Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-2-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine
```

```
<400> SEQUENCE: 8

Phe Xaa Xaa Arg Xaa Arg Gln
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 9

Phe Xaa Arg Arg Arg Arg Gln
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 10

Xaa Xaa Arg Xaa Arg Xaa Gln
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is L-2-naphthylalanine

<400> SEQUENCE: 11

Arg Arg Phe Arg Xaa Arg Gln
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
```

```
<223> OTHER INFORMATION: Xaa is L-2-naphthylalanine

<400> SEQUENCE: 12

Phe Arg Arg Arg Arg Xaa Gln
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is L-2-naphthylalanine

<400> SEQUENCE: 13

Xaa Arg Phe Arg Xaa Arg Gln
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa is L-2-naphthylalanine

<400> SEQUENCE: 14

Arg Arg Xaa Phe Arg Arg Gln
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic construct

<400> SEQUENCE: 15

Cys Arg Arg Arg Arg Phe Trp Gln
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is L-2-naphthylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
```

```
<222> LOCATION: (7)..(7)
<223> OTHER INFORMATION: Xaa is D-arginine

<400> SEQUENCE: 16

Phe Xaa Xaa Arg Xaa Arg Xaa Gln
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa is L-2-naphthylalanine

<400> SEQUENCE: 17

Phe Phe Xaa Arg Arg Arg Arg Gln
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa is L-2-naphthylalanine

<400> SEQUENCE: 18

Arg Phe Arg Phe Arg Xaa Arg Gln
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is selenocysteine

<400> SEQUENCE: 19

Xaa Arg Arg Arg Arg Phe Trp Gln
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic construct

<400> SEQUENCE: 20

Cys Arg Arg Arg Arg Phe Trp Gln
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic construct
```

```
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 21

Phe Xaa Arg Arg Arg Arg Gln Lys
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 22

Phe Xaa Arg Arg Arg Arg Gln Cys
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 23

Xaa Xaa Arg Xaa Arg Xaa Arg Gln
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 24

Phe Xaa Arg Arg Arg Arg Arg Gln
1               5

<210> SEQ ID NO 25
<211> LENGTH: 9
<212> TYPE: PRT
<213> ORGANISM: Artificial Sequence
<220> FEATURE:
```

```
<223> OTHER INFORMATION: synthetic construct
<220> FEATURE:
<221> NAME/KEY: MISC_FEATURE
<222> LOCATION: (5)..(5)
<223> OTHER INFORM

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 30

Phe Xaa Arg Arg Arg Arg Gln
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic construct

<400> SEQUENCE: 31

Phe Phe Arg Arg Arg Gln
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 32

Phe Phe Xaa Arg Xaa Gln
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is D-arginine

<400> SEQUENCE: 33

Phe Phe Arg Xaa Arg Gln
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic construct

<400> SEQUENCE: 34

Phe Arg Phe Arg Arg Gln
1               5

<210> SEQ ID NO 35
```

```
<211> LENGTH: 6
<212> TYPE: PRT
<213> ORGANISM: Artificial Sequence
<220> FEATURE:
<223> OTHER INFORMATION: synthetic construct

<400> SEQUENCE: 35

Phe Arg Arg Phe Arg Gln
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic construct

<400> SEQUENCE: 36

Phe Arg Arg Arg Phe Gln
1               5

<210> SEQ ID NO 37
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 37

Gly Xaa Arg Arg Arg Gln
1               5

<210> SEQ ID NO 38
<211> LENGTH: 6
<212> TYPE: PRT
<213> ORGANISM: Artificial Sequence
<220> FEATURE:
<223> OTHER INFORMATION: synthetic construct

<400> SEQUENCE: 38

Phe Phe Phe Arg Ala Gln
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic construct

<400> SEQUENCE: 39

Phe Phe Phe Arg Arg Gln
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic construct

<400> SEQUENCE: 40

Phe Phe Arg Arg Arg Arg Gln
1               5
```

```
<210> SEQ ID NO 41
<211> LENGTH: 7
<212> TYPE: PRT
<213> ORGANISM: Artificial Sequence
<220> FEATURE:
<223> OTHER INFORMATION: synthetic construct

<400> SEQUENCE: 41

Phe Arg Arg Phe Arg Arg Gln
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic construct

<400> SEQUENCE: 42

Phe Arg Arg Arg Phe Arg Gln
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic construct

<400> SEQUENCE: 43

Arg Phe Phe Arg Arg Arg Gln
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic construct

<400> SEQUENCE: 44

Arg Phe Arg Arg Phe Arg Gln
1               5

<210> SEQ ID NO 45
<211> LENGTH: 7
<212> TYPE: PRT
<213> ORGANISM: Artificial Sequence
<220> FEATURE:
<223> OTHER INFORMATION: synthetic construct

<400> SEQUENCE: 45

Phe Arg Phe Arg Arg Arg Gln
1               5

<210> SEQ ID NO 46
<211> LENGTH: 7
<212> TYPE: PRT
<213> ORGANISM: Artificial Sequence
<220> FEATURE:
<223> OTHER INFORMATION: synthetic construct

<400> SEQUENCE: 46

Phe Phe Phe Arg Arg Arg Gln
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: synthetic construct

<400> SEQUENCE: 47

Phe Phe Arg Arg Arg Phe
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic construct

<400> SEQUENCE: 48

Phe Arg Phe Phe Arg Arg Gln
1               5

<210> SEQ ID NO 49
<211> LENGTH: 7
<212> TYPE: PRT
<213> ORGANISM: Artificial Sequence
<220> FEATURE:
<223> OTHER INFORMATION: synthetic construct

<400> SEQUENCE: 49

Arg Arg Phe Phe Phe Arg Gln
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic construct

<400> SEQUENCE: 50

Phe Phe Arg Phe Arg Arg Gln
1               5

<210> SEQ ID NO 51
<211> LENGTH: 7
<212> TYPE: PRT
<213> ORGANISM: Artificial Sequence
<220> FEATURE:
<223> OTHER INFORMATION: synthetic construct

<400> SEQUENCE: 51

Phe Phe Arg Arg Phe Arg Gln
1               5

<210> SEQ ID NO 52
<211> LENGTH: 7
<212> TYPE: PRT
<213> ORGANISM: Artificial Sequence
<220> FEATURE:
<223> OTHER INFORMATION: synthetic construct

<400> SEQUENCE: 52

Phe Arg Arg Phe Phe Arg Gln
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: synthetic construct

<400> SEQUENCE: 53

Phe Arg Arg Phe Arg Phe Gln
1               5

<210> SEQ ID NO 54
<211> LENGTH: 7
<212> TYPE: PRT
<213> ORGANISM: Artificial Sequence
<220> FEATURE:
<223> OTHER INFORMATION: synthetic construct

<400> SEQUENCE: 54

Phe Arg Phe Arg Phe Arg Gln
1               5

<210> SEQ ID NO 55
<211> LENGTH: 7
<212> TYPE: PRT
<213> ORGANISM: Artificial Sequence
<220> FEATURE:
<223> OTHER INFORMATION: synthetic construct

<400> SEQUENCE: 55

Arg Phe Phe Arg Phe Arg Gln
1               5

<210> SEQ ID NO 56
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 56

Gly Xaa Arg Arg Arg Arg Gln
1               5

<210> SEQ ID NO 57
<211> LENGTH: 8
<212> TYPE: PRT
<213> ORGANISM: Artificial Sequence
<220> FEATURE:
<223> OTHER INFORMATION: synthetic construct

<400> SEQUENCE: 57

Phe Phe Phe Arg Arg Arg Arg Gln
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 58

Arg Phe Phe Arg Arg Arg Gln
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic construct

<400> SEQUENCE: 59

Arg Arg Phe Phe Arg Arg Arg
1               5

<210> SEQ ID NO 60
<211> LENGTH: 8
<212> TYPE: PRT
<213> ORGANISM: Artificial Sequence
<220> FEATURE:
<223> OTHER INFORMATION: synthetic construct

<400> SEQUENCE: 60

Arg Phe Phe Phe Arg Arg Arg Gln
1               5

<210> SEQ ID NO 61
<211> LENGTH: 8
<212> TYPE: PRT
<213> ORGANISM: Artificial Sequence
<220> FEATURE:
<223> OTHER INFORMATION: synthetic construct

<400> SEQUENCE: 61

Arg Arg Phe Phe Phe Arg Arg Gln
1               5

<210> SEQ ID NO 62
<211> LENGTH: 8
<212> TYPE: PRT
<213> ORGANISM: Artificial Sequence
<220> FEATURE:
<223> OTHER INFORMATION: synthetic construct

<400> SEQUENCE: 62

Phe Phe Arg Arg Phe Arg Arg Gln
1               5

<210> SEQ ID NO 63
<211> LENGTH: 8
<212> TYPE: PRT
<213> ORGANISM: Artificial Sequence
<220> FEATURE:
<223> OTHER INFORMATION: synthetic construct

<400> SEQUENCE: 63

Phe Phe Arg Arg Arg Arg Phe Gln
1               5

<210> SEQ ID NO 64
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 64

Phe Arg Arg Phe Phe Arg Arg Gln
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic construct

<400> SEQUENCE: 65

Phe Phe Phe Arg Arg Arg Arg Arg Gln
1               5

<210> SEQ ID NO 66
<211> LENGTH: 10
<212> TYPE: PRT
<213> ORGANISM: Artificial Sequence
<220> FEATURE:
<223> OTHER INFORMATION: synthetic construct

<400> SEQUENCE: 66

Phe Phe Phe Arg Arg Arg Arg Arg Arg Gln
1               5                   10

<210> SEQ ID NO 67
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 67

Phe Xaa Arg Xaa Arg Xaa Gln
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(2)
<223> OTHER INFORMATION: Xaa can be any naturally occurring amino acid

<400> SEQUENCE: 68

Xaa Xaa Arg Arg Arg Arg Gln
1               5

<210> SEQ ID NO 69
<211> LENGTH: 7
<212> TYPE: PRT
<213> ORGANISM: Artificial Sequence
<220> FEATURE:
```

```
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine

<400> SEQUENCE: 69

Phe Xaa Phe Arg Xaa Arg Gln
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 70

Xaa Phe Xaa Xaa Arg Xaa Gln
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine

<400> SEQUENCE: 71

Xaa Phe Xaa Arg Xaa Arg Gln
1               5

<210> SEQ ID NO 72
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
```

```
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 72

Phe Xaa Phe Xaa Arg Xaa Gln
1               5

<210> SEQ ID NO 73
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 73

Xaa Phe Xaa Xaa Arg Xaa Gln
1               5

<210> SEQ ID NO 74
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 74

Xaa Xaa Xaa Xaa Arg Xaa Gln
1               5

<210> SEQ ID NO 75
```

```
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-2-naphthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 75

Xaa Phe Xaa Xaa Arg Xaa Gln
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 76

Phe Xaa Xaa Arg Xaa Gln
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine
```

```
<400> SEQUENCE: 77

Xaa Xaa Xaa Arg Xaa Gln
1               5

<210> SEQ ID NO 78
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-arginine

<400> SEQUENCE: 78

Lys Xaa Phe Arg Xaa Arg Xaa Asp
1               5

<210> SEQ ID NO 79
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa is L-2,3-diaminopropionic acid
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-arginine

<400> SEQUENCE: 79

Xaa Xaa Phe Arg Xaa Arg Xaa Asp
1               5

<210> SEQ ID NO 80
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond
```

```
<400> SEQUENCE: 80

Cys Trp Trp Arg Arg Arg Arg Cys
1               5

<210> SEQ ID NO 81
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(9)
<223> OTHER INFORMATION: Cys residues jopined by disulfide bond

<400> SEQUENCE: 81

Cys Trp Trp Val Arg Arg Arg Arg Cys
1               5

<210> SEQ ID NO 82
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 82

Cys Phe Trp Arg Arg Arg Arg Cys
1               5

<210> SEQ ID NO 83
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 83

Cys Trp Trp Trp Arg Arg Arg Cys
1               5

<210> SEQ ID NO 84
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
```

```
<223> OTHER INFORMATION: Xaa is D-glutamate

<400> SEQUENCE: 84

Xaa Xaa Arg Glu Xaa Xaa Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 85

Xaa Xaa Arg Arg Xaa Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(3)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 86

Xaa Xaa Xaa Arg Xaa Xaa Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(3)
```

```
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 87

Xaa Xaa Xaa Arg Xaa Xaa Glu
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 88

Xaa Xaa Phe Arg Xaa Xaa Xaa
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 89

Xaa Xaa Phe Arg Xaa Xaa Glu
1               5

<210> SEQ ID NO 90
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
```

```
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 90

Xaa Xaa Xaa Arg Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 91

Xaa Xaa Xaa Arg Xaa Xaa Glu
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 92

Xaa Xaa Xaa Arg Xaa Xaa Glu
1               5

<210> SEQ ID NO 93
```

```
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 93

Xaa Xaa Xaa Arg Xaa Xaa Xaa
1               5

<210> SEQ ID NO 94
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Arg is modified with pimelic acid
<220> FEATURE:
<221> NAME/KEY: MISC_FEATURE
<222> LOCATION: (1)..(4)
<223> OTHER INFORMATION: Cyclization between Arg is modified with
      pimelic acid and Arg is modified with lysine peptoid residue
<220> FEATURE:
<221> NAME/KEY: MISC_FEATURE
<222> LOCATION: (4)..(4)
<223> OTHER INFORMATION: Arg is modified with lysine peptoid residue

<400> SEQUENCE: 94

Arg Gln Arg Arg Gly Arg Arg Arg
1               5

<210> SEQ ID NO 95
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 95

Lys Cys Phe Gln Trp Gln Arg Asn Met Arg Lys Val Arg Gly Pro Pro
1               5                   10                  15

Val Ser Cys

<210> SEQ ID NO 96
<211> LENGTH: 11
```

```
-continued

<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(11)
<223> OTHER INFORMATION: Cyclization between Lys and Glu
<220> FEATURE:
<221> NAME/KEY: MISC_FEATURE
<222> LOCATION: (2)..(2)
<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is D-lysine
<220> FEATURE:
<221> NAME/KEY: MISC_FEATURE
<222> LOCATION: (10)..(10)
<223> OTHER INFORMATION: Xaa is D-arginine

<400> SEQUENCE: 96

Lys Xaa Arg Xaa Gly Xaa Lys Xaa Arg Xaa Glu
1               5                   10

<210> SEQ ID NO 97
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(12)
<223> OTHER INFORMATION: Cyclization between Lys and Glu
<220> FEATURE:
<221> NAME/KEY: MISC_FEATURE
<222> LOCATION: (2)..(2)
<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is D-arginine
<220> FEATURE:
<221> NAME/KEY: MISC_FEATURE
<222> LOCATION: (10)..(10)
<223> OTHER INFORMATION: Xaa is D-arginine

<400> SEQUENCE: 97

Lys Xaa Arg Xaa Arg Xaa Arg Xaa Arg Xaa Arg Glu
1               5                   10

<210> SEQ ID NO 98
<211> LENGTH: 14
<212> TYPE: PRT
<213> ORGANISM: Artificial Sequence
<220> FEATURE:
<223> OTHER INFORMATION: synthetic construct
<220> FEATURE:
```

```
<221> NAME/KEY: MISC_FEATURE
<222> LOCATION: (13)..(13)
<223> OTHER INFORMATION: Xaa is D-proline

<400> SEQUENCE: 98

Arg Val Arg Thr Arg Gly Lys Arg Arg Ile Arg Arg Xaa Pro
1               5                   10

<210> SEQ ID NO 99
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: Xaa is D-proline

<400> SEQUENCE: 99

Arg Thr Arg Thr Arg Gly Lys Arg Arg Ile Arg Val Xaa Pro
1               5                   10

<210> SEQ ID NO 100
<211> LENGTH: 8
<212> TYPE: PRT
<213> ORGANISM: Artificial Sequence
<220> FEATURE:
<223> OTHER INFORMATION: synthetic construct

<400> SEQUENCE: 100

Trp Arg Trp Arg Trp Arg Trp Arg
1               5

<210> SEQ ID NO 101
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 101

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 102
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
```

```
<223> OTHER INFORMATION: Macrocyclization by multicomponent reaction
      with aziridine aldehyde and isocyanide
<220> FEATURE:
<221> NAME/KEY: MISC_FEATURE
<222> LOCATION: (2)..(2)
<223> OTHER INFORMATION: Xaa is L-3-cyclohexyl-alanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is L-3-cyclohexyl-alanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is L-3-cyclohexyl-alanine
<220> FEATURE:
<221> NAME/KEY: MISC_FEATURE
<222> LOCATION: (7)..(7)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is L-3-cyclohexyl-alanine
<220> FEATURE:
<221> NAME/KEY: MISC_FEATURE
<222> LOCATION: (9)..(9)
<223> OTHER INFORMATION: Xaa is D-arginine

<400> SEQUENCE: 102

Pro Xaa Xaa Xaa Xaa Xaa Xaa Xaa Xaa Gly
1               5                   10

<210> SEQ ID NO 103
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Ser is modified with trimesic acid
<220> FEATURE:
<221> NAME/KEY: MISC_FEATURE
<222> LOCATION: (1)..(13)
<223> OTHER INFORMATION: N-terminal amine and side chains of two L-2,3-
      diaminopropionic acid residues bicyclized with trimesic acid
<220> FEATURE:
<221> NAME/KEY: MISC_FEATURE
<222> LOCATION: (2)..(2)
<223> OTHER INFORMATION: Xaa is D-valine
<220> FEATURE:
<221> NAME/KEY: MISC_FEATURE
<222> LOCATION: (4)..(4)
<223> OTHER INFORMATION: Xaa is L-difluorophosphonomethyl phenylalanine
<220> FEATURE:
<221> NAME/KEY: MISC_FEATURE
<222> LOCATION: (6)..(6)
<223> OTHER INFORMATION: Xaa is L-2,3-diaminopropionic acid
<220> FEATURE:
<221> NAME/KEY: MISC_FEATURE
<222> LOCATION: (8)..(8)
<223> OTHER INFORMATION: Xaa is L-2-naphthylalanine
<220> FEATURE:
<221> NAME/KEY: MISC_FEATURE
<222> LOCATION: (13)..(13)
<223> OTHER INFORMATION: Xaa is L-2,3-diaminopropionic acid
```

<400> SEQUENCE: 103

Ser Xaa Pro Xaa His Xaa Phe Xaa Arg Arg Arg Xaa
1               5                   10

<210> SEQ ID NO 104
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-alanine is modified with trimesic acid
<220> FEATURE:
<221> NAME/KEY: MISC_FEATURE
<222> LOCATION: (1)..(1)
<223> OTHER INFORMATION: Xaa is D-alanine
<220> FEATURE:
<221> NAME/KEY: MISC_FEATURE
<222> LOCATION: (1)..(16)
<223> OTHER INFORMATION: N-terminal amine and side chains of two L-2,3-
      diaminopropionic acid residues bicyclized with trimesic acid
<220> FEATURE:
<221> NAME/KEY: MISC_FEATURE
<222> LOCATION: (2)..(2)
<223> OTHER INFORMATION: Xaa is sarcosine
<220> FEATURE:
<221> NAME/KEY: MISC_FEATURE
<222> LOCATION: (3)..(3)
<223> OTHER INFORMATION: Xaa is D-phosphothreonine
<220> FEATURE:
<221> NAME/KEY: MISC_FEATURE
<222> LOCATION: (4)..(4)
<223> OTHER INFORMATION: Xaa is L-piperidine-2-carboxylic acid
<220> FEATURE:
<221> NAME/KEY: MISC_FEATURE
<222> LOCATION: (5)..(5)
<223> OTHER INFORMATION: Xaa is L-2-naphthylalanine
<220> FEATURE:
<221> NAME/KEY: MISC_FEATURE
<222> LOCATION: (8)..(8)
<223> OTHER INFORMATION: Xaa is D-alanine
<220> FEATURE:
<221> NAME/KEY: MISC_FEATURE
<222> LOCATION: (9)..(9)
<223> OTHER INFORMATION: Xaa is L-2,3-diaminopropionic acid
<220> FEATURE:
<221> NAME/KEY: MISC_FEATURE
<222> LOCATION: (11)..(11)
<223> OTHER INFORMATION: Xaa is L-2-naphthylalanine
<220> FEATURE:
<221> NAME/KEY: MISC_FEATURE
<222> LOCATION: (16)..(16)
<223> OTHER INFORMATION: Xaa is L-2,3-diaminopropionic acid

<400> SEQUENCE: 104

Xaa Xaa Xaa Xaa Xaa Arg Ala Xaa Xaa Phe Xaa Arg Arg Arg Arg Xaa
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(15)
<223> OTHER INFORMATION: Three Cys side chains bicyclized with
      tris(bromomethyl)benzene

<400> SEQUENCE: 105

Cys Arg Arg Ser Arg Arg Gly Cys Gly Arg Arg Ser Arg Arg Cys Gly
1               5                   10                  15

<210> SEQ ID NO 106
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(2)
<223> OTHER INFORMATION: linked by dodecanoyl moiety

<400> SEQUENCE: 106

Lys Arg Arg Arg Arg
1               5

<210> SEQ ID NO 107
<211> LENGTH: 16
<212> TYPE: PRT
<213> ORGANISM: Artificial Sequence
<220> FEATURE:
<223> OTHER INFORMATION: synthetic construct

<400> SEQUENCE: 107

Leu Lys Lys Leu Cys Lys Leu Leu Lys Leu Cys Lys Leu Ala Gly
1               5                   10                  15

<210> SEQ ID NO 108
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(9)
<223> OTHER INFORMATION: Cyclization between Lys and Glu

<400> SEQUENCE: 108

Arg Arg Arg Arg Lys Arg Arg Arg Glu
1               5

<210> SEQ ID NO 109
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(9)
<223> OTHER INFORMATION: Cyclization between Lys and Glu

<400> SEQUENCE: 109

Arg Arg Arg Lys Arg Arg Arg Arg Glu
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE

```
<222> LOCATION: (3)..(9)
<223> OTHER INFORMATION: Cyclization between Lys and Glu

<400> SEQUENCE: 110

Arg Arg Lys Arg Arg Arg Arg Glu
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: Cyclization between Lys and Glu

<400> SEQUENCE: 111

Arg Lys Arg Arg Arg Arg Arg Arg Glu
1               5

<210> SEQ ID NO 112
<211> LENGTH: 8
<212> TYPE: PRT
<213> ORGANISM: Artificial Sequence
<220> FEATURE:
<223> OTHER INFORMATION: synthetic construct

<400> SEQUENCE: 112

Cys Arg Cys Arg Cys Arg Cys Arg
1               5

<210> SEQ ID NO 113
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-propargylglycine
<220> FEATURE:
<221> NAME/KEY: MISC_FEATURE
<222> LOCATION: (1)..(12)
<223> OTHER INFORMATION: Cyclization by the click reaction between
      L-propargylglycine and L-6-Azido-2-amino-hexanoic
<220> FEATURE:
<221> NAME/KEY: MISC_FEATURE
<222> LOCATION: (12)..(12)
<223> OTHER INFORMATION: Xaa is L-6-Azido-2-amino-hexanoic

<400> SEQUENCE: 113

Xaa Leu Arg Lys Arg Leu Arg Lys Phe Arg Asn Xaa
1               5                   10

<210> SEQ ID NO 114
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(4)
<223> OTHER INFORMATION: Xaa is L-2,3-diaminopropionic acid
<220> FEATURE:
<221> NAME/KEY: MISC_FEATURE
<222> LOCATION: (5)..(5)
<223> OTHER INFORMATION: Xaa is D-phenylalanine
```

```
<220> FEATURE:
<221> NAME/KEY: MISC_FEATURE
<222> LOCATION: (7)..(8)
<223> OTHER INFORMATION: Xaa is L-2,3-diaminopropionic acid

<400> SEQUENCE: 114

Thr Xaa Xaa Xaa Xaa Leu Xaa Xaa Thr
1               5

<210> SEQ ID NO 115
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-amino-3-guanidinylpropionic acid
<220> FEATURE:
<221> NAME/KEY: MISC_FEATURE
<222> LOCATION: (3)..(3)
<223> OTHER INFORMATION: Xaa is L-2,3-diaminopropionic acid
<220> FEATURE:
<221> NAME/KEY: MISC_FEATURE
<222> LOCATION: (4)..(4)
<223> OTHER INFORMATION: Xaa is L-2-amino-3-guanidinylpropionic acid
<220> FEATURE:
<221> NAME/KEY: MISC_FEATURE
<222> LOCATION: (5)..(5)
<223> OTHER INFORMATION: Xaa is D-phenylalanine
<220> FEATURE:
<221> NAME/KEY: MISC_FEATURE
<222> LOCATION: (7)..(8)
<223> OTHER INFORMATION: Xaa is L-2-amino-3-guanidinylpropionic acid

<400> SEQUENCE: 115

Thr Xaa Xaa Xaa Xaa Leu Xaa Xaa Thr
1               5

<210> SEQ ID NO 116
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 116

Phe Xaa Arg Arg Arg Arg Gln
1               5

<210> SEQ ID NO 117
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is L-2-naphthylalanine
<220> FEATURE:
<221> NAME/KEY: MISC_FEATURE
<222> LOCATION: (5)..(5)
<223> OTHER INFORMATION: Xaa is D-arginine
```

```
<220> FEATURE:
<221> NAME/KEY: MISC_FEATURE
<222> LOCATION: (7)..(7)
<223> OTHER INFORMATION: Xaa is D-arginine

<400> SEQUENCE: 117

Phe Xaa Xaa Arg Xaa Arg Xaa Gln
1               5

<210> SEQ ID NO 118
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 118

Xaa Xaa Arg Xaa Arg Xaa Gln
1               5

<210> SEQ ID NO 119
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 119

Xaa Xaa Arg Xaa Arg Xaa Arg Gln
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-2-naphthylalanine
```

```
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamine

<400> SEQUENCE: 120

Phe Xaa Xaa Arg Xaa Arg Xaa
1               5

<210> SEQ ID NO 121
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is D-2-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 121

Phe Xaa Xaa Arg Xaa Arg Gln
1               5

<210> SEQ ID NO 122
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 122

Phe Xaa Arg Arg Arg Arg Arg Gln
1               5

<210> SEQ ID NO 123
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is L-2-naphthylalanine

<400> SEQUENCE: 123

Arg Arg Phe Arg Xaa Arg Gln
1               5

<210> SEQ ID NO 124
```

```
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa is L-2-naphthylalanine

<400> SEQUENCE: 124

Phe Phe Xaa Arg Arg Arg Arg Gln
1               5

<210> SEQ ID NO 125
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa is L-2-naphthylalanine

<400> SEQUENCE: 125

Arg Phe Arg Phe Arg Xaa Arg Gln
1               5

<210> SEQ ID NO 126
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-naphthylalanine

<400> SEQUENCE: 126

Phe Xaa Arg Arg Arg Gln
1               5

<210> SEQ ID NO 127
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa is L-2-naphthylalanine

<400> SEQUENCE: 127

Phe Arg Arg Arg Arg Xaa Gln
1               5

<210> SEQ ID NO 128
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
```

```
<222> LOCATION: (5)..(5)
<223> OTHER INFORMATION: Xaa is L-2-naphthylalanine

<400> SEQUENCE: 128

Xaa Arg Phe Arg Xaa Arg Gln
1               5

<210> SEQ ID NO 129
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa is L-2-naphthylalanine

<400> SEQUENCE: 129

Arg Arg Xaa Phe Arg Arg Gln
1               5

<210> SEQ ID NO 130
<211> LENGTH: 200
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(200)
<223> OTHER INFORMATION: up to 195 residues may be absent in groups of 5

<400> SEQUENCE: 130

Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg
                20                  25                  30

Arg Arg Arg Arg Arg Arg Arg Arg Arg Arg Arg Arg Arg Arg Arg
            35                  40                  45

Arg Arg Arg Arg Arg Arg Arg Arg Arg Arg Arg Arg Arg Arg Arg
        50                  55                  60

Arg Arg Arg Arg Arg Arg Arg Arg Arg Arg Arg Arg Arg Arg Arg
65                  70                  75                  80

Arg Arg Arg Arg Arg Arg Arg Arg Arg Arg Arg Arg Arg Arg Arg
                85                  90                  95

Arg Arg Arg Arg Arg Arg Arg Arg Arg Arg Arg Arg Arg Arg Arg
            100                 105                 110

Arg Arg Arg Arg Arg Arg Arg Arg Arg Arg Arg Arg Arg Arg Arg
        115                 120                 125

Arg Arg Arg Arg Arg Arg Arg Arg Arg Arg Arg Arg Arg Arg Arg
    130                 135                 140

Arg Arg Arg Arg Arg Arg Arg Arg Arg Arg Arg Arg Arg Arg Arg
145                 150                 155                 160
```

Arg Arg Arg Arg Arg Arg Arg Arg Arg Arg Arg Arg Arg
                165                 170                 175

Arg Arg Arg Arg Arg Arg Arg Arg Arg Arg Arg Arg Arg
            180                 185                 190

Arg Arg Arg Arg Arg Arg Arg Arg
        195                 200

<210> SEQ ID NO 131
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: up to 5 may be absent

<400> SEQUENCE: 131

Cys Arg Arg Arg Arg Arg Arg Arg Arg Cys
1               5                   10

<210> SEQ ID NO 132
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is beta-alanine
<220> FEATURE:
<221> NAME/KEY: MISC_FEATURE
<222> LOCATION: (3)..(10)
<223> OTHER INFORMATION: up to 5 may be absent

<400> SEQUENCE: 132

Cys Xaa Arg Arg Arg Arg Arg Arg Arg Cys
1               5                   10

<210> SEQ ID NO 133
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: up to 5 may be absent
<220> FEATURE:
<221> NAME/KEY: MISC_FEATURE
<222> LOCATION: (10)..(10)
<223> OTHER INFORMATION: Xaa is beta-alanine

<400> SEQUENCE: 133

Cys Arg Arg Arg Arg Arg Arg Arg Xaa Cys
1               5                   10

```
<210> SEQ ID NO 134
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 134

Cys Xaa Arg Arg Arg Arg Arg Arg Arg Arg Xaa Cys
1               5                   10

<210> SEQ ID NO 135
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(3)
<223> OTHER INFORMATION: Xaa is beta-alanine
<220> FEATURE:
<221> NAME/KEY: MISC_FEATURE
<222> LOCATION: (2)..(3)
<223> OTHER INFORMATION: beta-alanine residues are joined by a polyamine
      of 3 to 8 subunits of which up to 5 may be absent

<400> SEQUENCE: 135

Cys Xaa Xaa Cys
1

<210> SEQ ID NO 136
<211> LENGTH: 7
<212> TYPE: PRT
<213> ORGANISM: Artificial Sequence
<220> FEATURE:
<223> OTHER INFORMATION: synthetic construct

<400> SEQUENCE: 136

Cys Arg Arg Arg Arg Arg Cys
1               5

<210> SEQ ID NO 137
<211> LENGTH: 21
<212> TYPE: DNA
<213> ORGANISM: Artificial Sequence
<220> FEATURE:
<223> OTHER INFORMATION: siLuc siRNA sequence

<400> SEQUENCE: 137
cuuacgcuga guacuucgat t                                              21

<210> SEQ ID NO 138
<211> LENGTH: 21
<212> TYPE: DNA
<213> ORGANISM: Artificial Sequence
<220> FEATURE:
<223> OTHER INFORMATION: siLuc siRNA sequence
```

-continued

<400> SEQUENCE: 138
ucgaaguacu cagcguaagt t     21

<210> SEQ ID NO 139
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (17)..(17)
<223> OTHER INFORMATION: cm

<400> SEQUENCE: 139
aangnngggn gnnaannaat t     21

<210> SEQ ID NO 140
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (13)..(13)
<223> OTHER INFORMATION: cm

<400> SEQUENCE: 140
uugaunaacg ccnagcguut t     21

<210> SEQ ID NO 141
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)

-continued

```
<223> OTHER INFORMATION: Xaa is L-2-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (7)..(8)
<223> OTHER INFORMATION: Gln and Cys are joined by a miniPEG (diethylene
      glycol) moiety

<400> SEQUENCE: 141

Xaa Xaa Arg Xaa Arg Xaa Gln Cys
1               5

<210> SEQ ID NO 142
<211> LENGTH: 5
<212> TYPE: PRT
<213> ORGANISM: Artificial Sequence
<220> FEATURE:
<223> OTHER INFORMATION: synthetic construct

<400> SEQUENCE: 142

Arg Arg Arg Arg Arg
1               5

<210> SEQ ID NO 143
<211> LENGTH: 6
<212> TYPE: PRT
<213> ORGANISM: Artificial Sequence
<220> FEATURE:
<223> OTHER INFORMATION: synthetic construct

<400> SEQUENCE: 143

Arg Arg Arg Arg Arg Arg
1               5

<210> SEQ ID NO 144
<211> LENGTH: 20
<212> TYPE: PRT
<213> ORGANISM: Artificial Sequence
<220> FEATURE:
<223> OTHER INFORMATION: synthetic construct

<400> SEQUENCE: 144

Arg Arg Arg Arg Arg Ser Ser Arg Arg Arg Arg Arg Arg Ser Ser Arg
1               5                   10                  15

Arg Arg Arg Arg
            20

<210> SEQ ID NO 145
<211> LENGTH: 6
<212> TYPE: PRT
<213> ORGANISM: Artificial Sequence
<220> FEATURE:
<223> OTHER INFORMATION: synthetic construct

<400> SEQUENCE: 145

Arg Arg Arg Arg Arg Cys
1               5
```

What is claimed is:

1. A polypeptide conjugate of the formula (I):

CPP-L-[P]$_n$-L-CPP  (I)

wherein:
P comprises a polyarginine peptide (pArg) comprising at least three monomers selected from arginine or arginine-analog or a polyamine selected from a spermidine polymer or a spermine polymer;
each L independently comprises an optionally substituted —(O—CH$_2$CH$_2$)$_z$- or an optionally substituted —(CH$_2$CH$_2$—O)$_z$-, wherein z is an integer from 1 to 20;
each CPP is, independently, a cyclic CPP (cCPP) comprising from 4 to 14 amino acid monomers; and
n is an integer from 1 to 50.

2. The polypeptide conjugate of claim 1, wherein P further comprises at least one group of the formula:

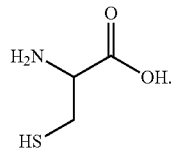

3. The polypeptide conjugate of claim 1, wherein n is 1-40.
4. The polypeptide conjugate of claim 1, wherein n is 2-40.
5. The polypeptide conjugate of claim 1, wherein n is 2-30.
6. The polypeptide conjugate of claim 1, wherein n is 2-20.
7. The polypeptide conjugate of claim 1, wherein n is 2-10.
8. The polypeptide conjugate of claim 1, wherein each cCPP independently comprises three arginines.
9. The polypeptide conjugate of claim 8, wherein each cCPP independently comprises at least three amino acids having a hydrophobic side chain.

10. The polypeptide conjugate of claim 1, wherein each cCPP independently comprises the sequence:
AA$_{H2}$-AA$_{H1}$-R-r-R;
AA$_{H2}$-AA$_{H1}$-R-r-r;
AA$_{H2}$-AA$_{H1}$-r-R-R,
AA$_{H2}$-AA$_{H1}$-r-R-r;
R-R-r-AA$_{H1}$-AA$_{H2}$;
r-R-r-AA$_{H1}$-AA$_{H2}$;
r-r-R-AA$_{H1}$-AA$_{H2}$; or
R-r-R-AA$_{H1}$-AA$_{H2}$;
wherein each of AA$_{H1}$ and AA$_{H2}$ is independently an amino acid having a hydrophobic side chain.

11. The polypeptide conjugate of claim 1, wherein each cCPP independently comprises the sequence:
AA$_{H3}$-AA$_{H2}$-AA$_{H1}$-R-r;
AA$_{H3}$-AA$_{H2}$-AA$_{H1}$-R-r;
AA$_{H3}$-AA$_{H2}$-AA$_{H1}$-r-R;
AA$_{H3}$-AA$_{H2}$-AA$_{H1}$-r-R;
R-r-AA$_{H1}$-AA$_{H2}$-AA$_{H3}$;
R-r-AA$_{H1}$-AA$_{H2}$-AA$_{H3}$;
r-R-AA$_{H1}$-AA$_{H2}$-AA$_{H3}$; or
r-R-AA$_{H1}$-AA$_{H2}$-AA$_{H3}$;
wherein each of AA$_{H1}$, AA$_{H2}$, and AA$_{H3}$ is independently an amino acid having a hydrophobic side chain.

12. The polypeptide conjugate of claim 1, wherein each cCPP independently comprises the sequence:
cyclo(fΦRrRrQ) or
cyclo(FfΦRrRrQ).

13. The polypeptide conjugate of claim 1, wherein each pArg is independently:
-Cys-(Arg)$_x$-Cys-;
-Cys-βAla(Arg)$_x$-Cys-;
-Cys-(Arg)$_x$-βAla-Cys-; or
-Cys-βAla(Arg)$_x$-βAla-Cys-;
wherein x is 3, 4, 5, 6, 7, or 8.

14. The polypeptide conjugate of claim 1, wherein each P is independently:
Cys-(polyamine)$_x$-Cys-;
-Cys-βAla(polyamine)$_x$-Cys-;
-Cys-(polyamine)$_x$-βAla-Cys-;
-Cys-βAla(polyamine)$_x$-βAla-Cys-; or
-S-(polyamine)$_x$-S-
wherein x is 3, 4, 5, 6, 7, or 8.

15. The polypeptide conjugate of claim 1, wherein [pArg]$_n$ is:

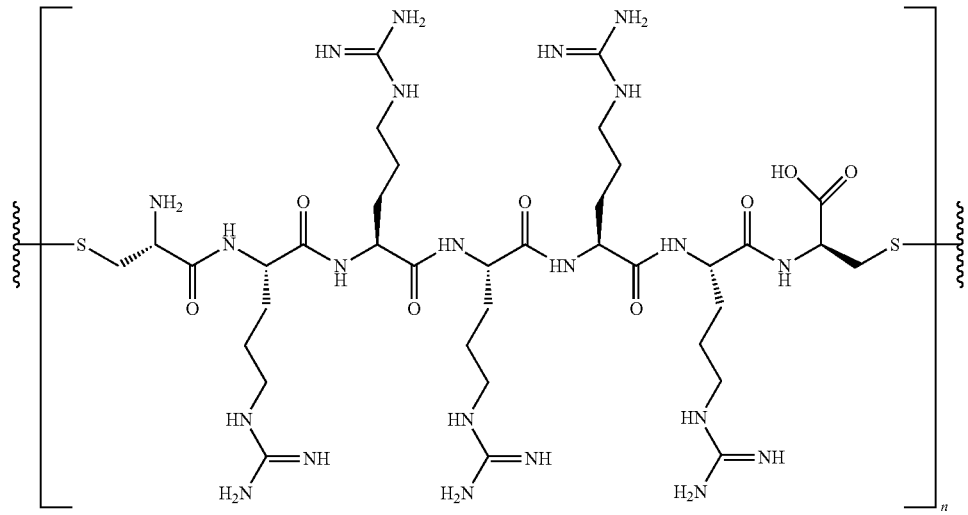

or a charged species thereof.

16. The polypeptide conjugate of claim 1, wherein the polypeptide has the structure:

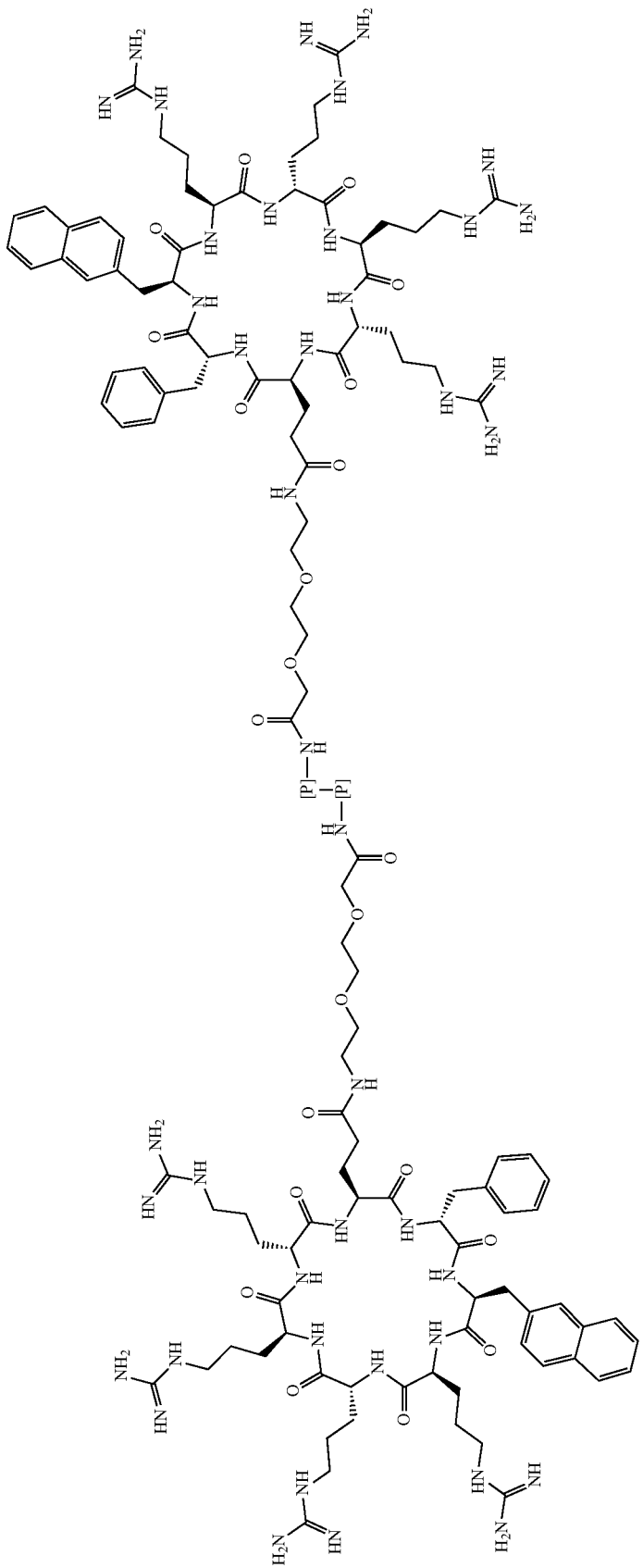

or a charged species thereof, or

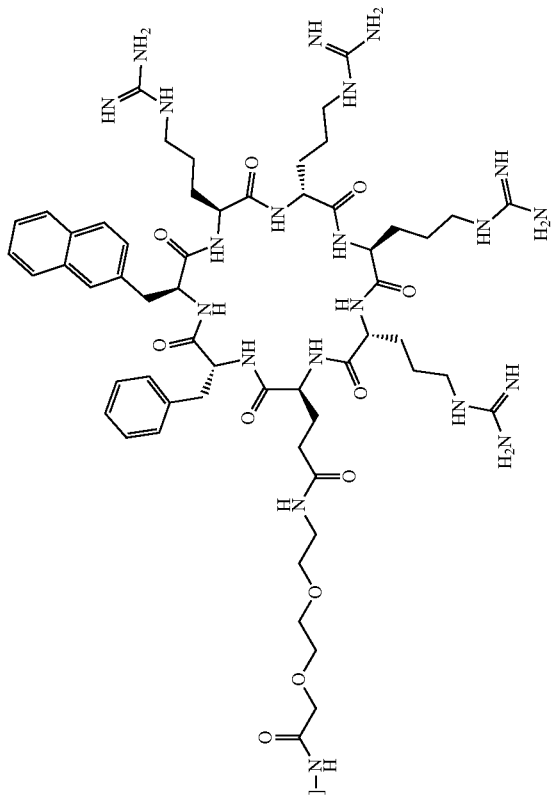
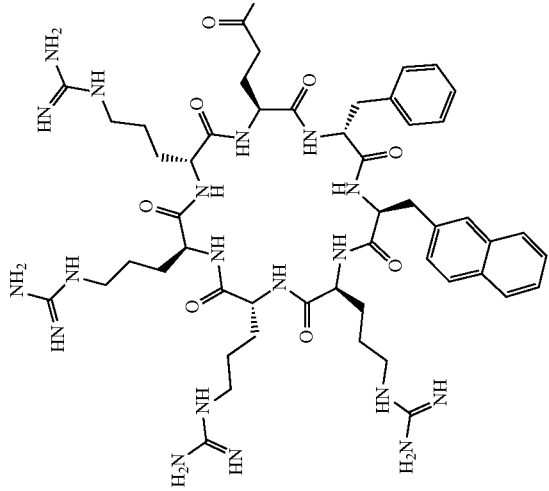

or a charged species thereof.
17. The polypeptide conjugate of claim 1, wherein the polypeptide has the structure:
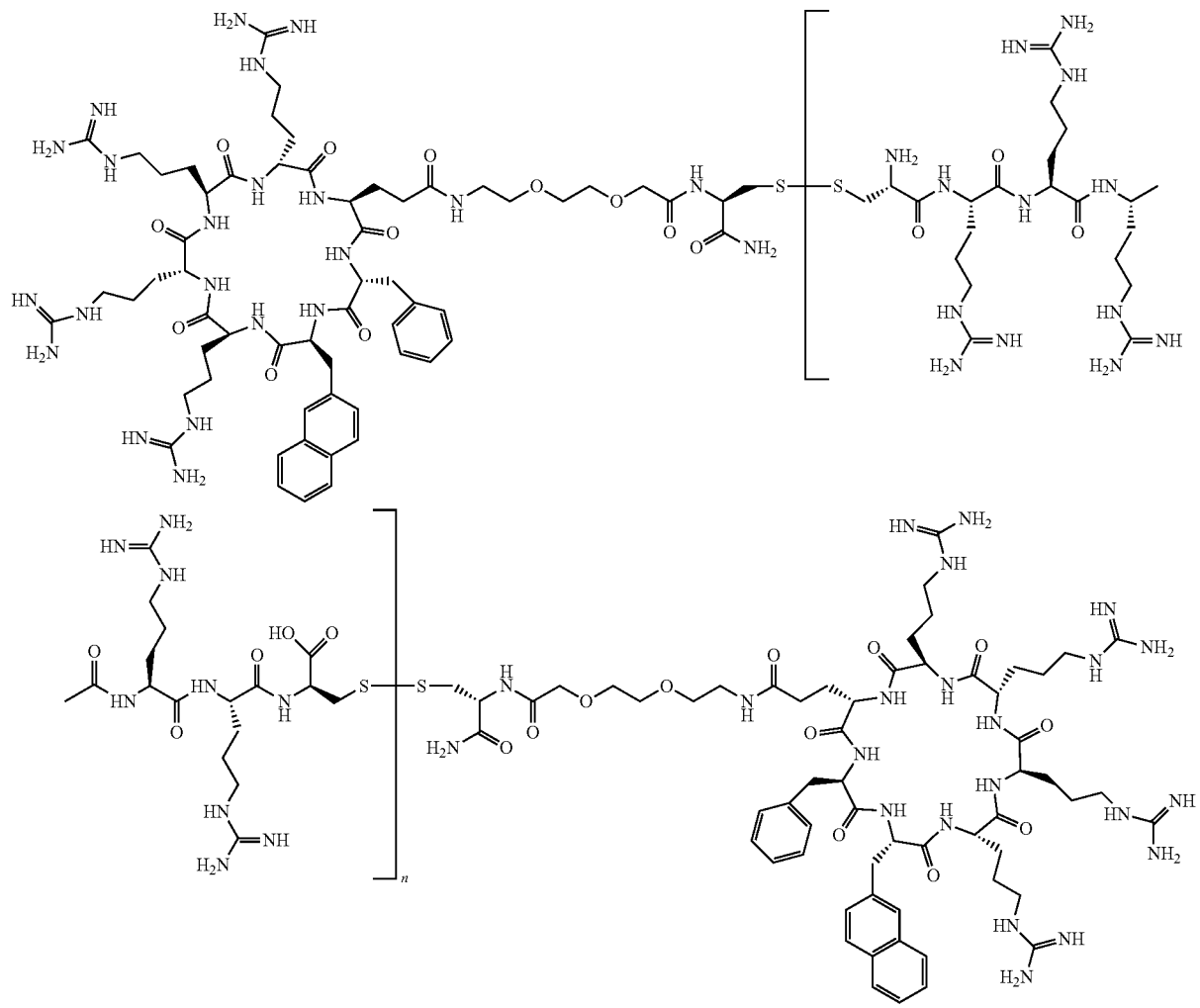
or a charged species thereof, or

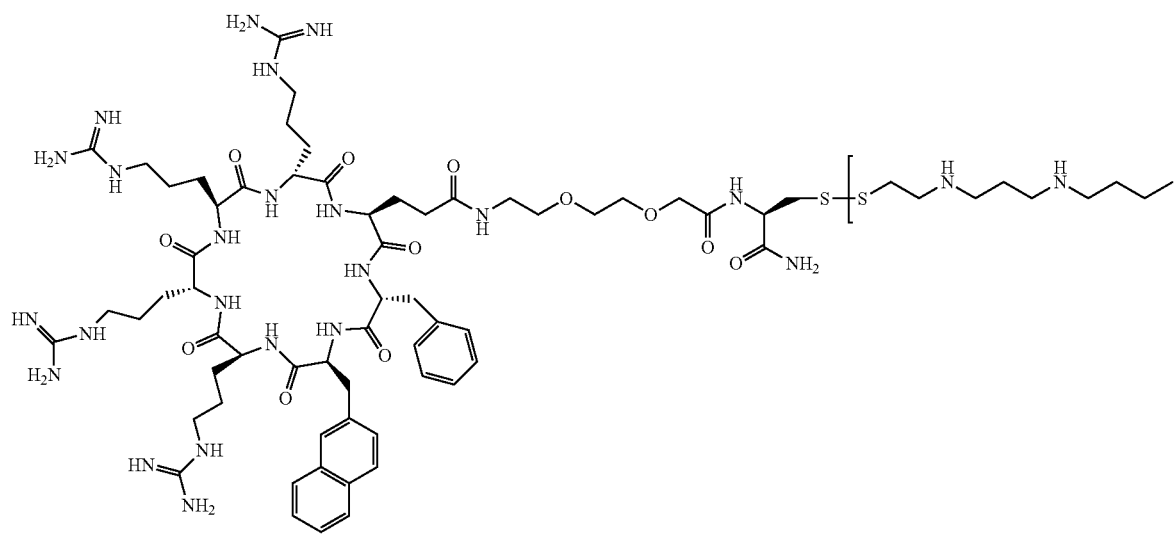

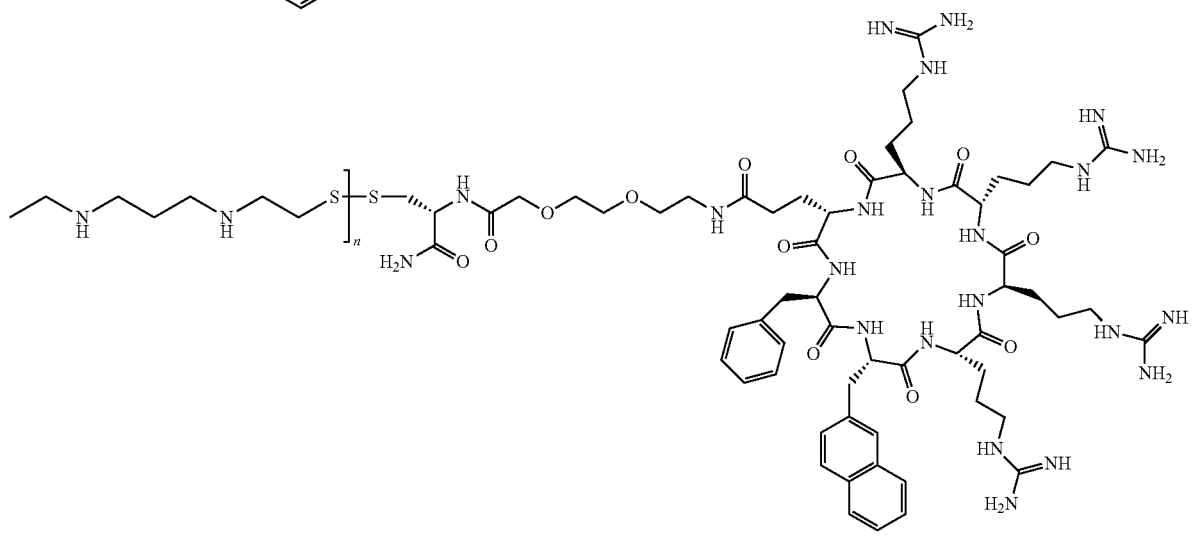

or a charge species thereof.

18. A complex comprising the polypeptide conjugate of claim 1 and at least one nucleic acid sequence.

19. A method of delivering a nucleic acid sequence to a cell of a subject in need thereof, comprising administering the complex of claim 18.

20. A method of treating a disease or condition in a patient in need thereof, comprising administering the complex of claim 18 to the patient.

* * * * *